United States Patent
Wormser

(10) Patent No.: US 7,528,227 B2
(45) Date of Patent: May 5, 2009

(54) HISTONE H2A PEPTIDE DERIVATIVES AND USES THEREOF

(75) Inventor: Uri Wormser, Jerusalem (IL)

(73) Assignee: Yissum Research Development Company of the Hebrew University of Jerusalem, Jerusalem (IL)

(*) Notice: Subject to any disclaimer, the term of this patent is extended or adjusted under 35 U.S.C. 154(b) by 0 days.

(21) Appl. No.: 11/527,162

(22) Filed: Sep. 25, 2006

(65) Prior Publication Data

US 2007/0093426 A1 Apr. 26, 2007

Related U.S. Application Data

(63) Continuation-in-part of application No. PCT/IL2005/000328, filed on Mar. 23, 2005.

(60) Provisional application No. 60/555,334, filed on Mar. 23, 2004, provisional application No. 60/831,216, filed on Jul. 17, 2006.

(51) Int. Cl.
A61K 38/04 (2006.01)
A61K 38/08 (2006.01)
A61K 38/10 (2006.01)
C07K 7/06 (2006.01)
C07K 7/08 (2006.01)

(52) U.S. Cl. ............... 530/328; 530/300; 530/326; 530/327; 530/329; 530/330; 514/2; 514/13; 514/14; 514/15; 514/16; 514/17

(58) Field of Classification Search ............... None
See application file for complete search history.

(56) References Cited

U.S. PATENT DOCUMENTS

| | | | |
|---|---|---|---|
| 4,215,109 A | 7/1980 | Ruhenstroth-Bauer et al. | 424/177 |
| 4,966,848 A * | 10/1990 | Smith et al. | 435/193 |
| 5,223,421 A * | 6/1993 | Smith et al. | 435/193 |
| 5,300,501 A | 4/1994 | Porter et al. | 514/238.2 |
| 5,776,892 A * | 7/1998 | Counts et al. | 514/11 |
| 5,837,218 A * | 11/1998 | Peers et al. | 424/1.69 |
| 6,468,537 B1 | 10/2002 | Datta et al. | 424/185.1 |
| 6,673,623 B1 * | 1/2004 | Huberman | 436/86 |
| 7,238,656 B2 * | 7/2007 | Wormser | 514/2 |
| 2003/0007964 A1 | 1/2003 | Bae et al. | 424/94.61 |
| 2004/0039157 A1 | 2/2004 | Staton et al. | 530/324 |
| 2004/0224077 A1 | 11/2004 | Kochhar et al. | 426/650 |

FOREIGN PATENT DOCUMENTS

| | | |
|---|---|---|
| DE | 27 50 920 B2 | 5/1979 |
| EP | 0 489 577 A | 6/1992 |
| EP | 1297 753 A | 4/2003 |
| WO | WO 98/09985 | 3/1998 |
| WO | WO 2001/38522 | 5/2001 |
| WO | WO 02/33089 A2 * | 4/2002 |
| WO | WO 03/017920 A2 | 3/2003 |

OTHER PUBLICATIONS

Martin Citron, "Alzheimer's Disease: Treatments In Discovery And Development" Nature Neuroscience, vol. 5, pp. 1055-1057 (2002).
F. Rizzello, et al. "The Management Of Refractory Crohn's Disease" Ailment Pharmacol. Ther., vol. 16, pp. 40-47 (2002).
Korczyn & Nussbaum, "Emerging Therapies In The Pharmacological Treatment Of Parkinson's Disease" Drugs, vol. 62, No. 5, pp. 775-786 (2002).
Skuk et al. "Experimental And Therapeutic Approaches To Muscular Dystrophies" Current Opinion in Neurology, vol. 15, pp. 563-569 (2002).
I Coussens & Werb, "Inflammation And Cancer", Nature, vol. 420, pp. 860-867 (2002).
Wiendl & Hohifeld et al., "Therapeutic Approaches In Multiple Sclerosis" Biodrugs, vol. 16, 3, pp. 183-200 (2002).
D. M. Ashcroft et al. "Therapeutic Strategies For Psoriasis." Journal of Clinical. Pharmacy and Therapeutics, vol. 25, pp. 1-10. (2000).
Y. Masuda et al., "Human Fibrinopeptide A Mediates Allergic Reaction In Mice In The Acute Phase.", Peptides, vol. 22, pp. 1511-1513 (2001).
Scherer et al. "The Effect Of Fibrinopeptides A And B On Experimental Allergic Encephalomyelitis" Clin. exp. Immunol., vol. 40, pp. 49-59 (1980).
Elgjo, K., et al., "Proliferation-Dependent Effect Of Skin Extracts (Chalone) On Mouse Epidermal Cell Flux At The $G_1$-S, S-$G_2$ and $G_2$-M Transitions", Virchows Archiv.[Cell Pathol], vol. 42, No. 2, pp. 143-151 (1983).

* cited by examiner

*Primary Examiner*—Cecilia Tsang
*Assistant Examiner*—Julie Ha
(74) *Attorney, Agent, or Firm*—Winston & Strawn LLP

(57) ABSTRACT

Peptides derived from a segment of human histone H2A, the segment corresponding to amino acid residues 36-44 of human histone H2A, are capable of reducing or ameliorating the extent of injury induced by noxious stimuli when administered to animals. Pharmaceutical compositions and methods of using these peptides are also disclosed. The pharmaceutical compositions according to the invention are useful for treating and protecting against inflammatory diseases, autoimmune diseases, for treating and protecting against tissue damage, for inhibiting metalloproteinase activity, and for treating and protecting against diseases associated with the breakdown of extracellular matrix or connective tissues.

10 Claims, 27 Drawing Sheets

Hydroxyl radical scavenging by IIIM1

Hydroxyl radical scavenging by MeAla IIIU3

Dose-response relationship of orally administered peptide in EAE model

Days after MOG immunization

Structure acitivity relationship of orally administered peptide in EAE model

Days after MOG immunization

Effect of IIIM1 on LPS-induced mortality

The effect of different IIIM1 doses on LPS-induced mortality (sepsis) in mice

US 7,528,227 B2

HISTONE H2A PEPTIDE DERIVATIVES AND USES THEREOF

CROSS-REFERENCE TO RELATED APPLICATIONS

This application is a continuation-in-part of International application PCT/IL2005/000328 filed Mar. 23, 2005, which claims the benefit of U.S. application Ser. No. 60/555,334 filed Mar. 23, 2004. This application also claims the benefit of U.S. application Ser. No. 60/831,216 filed Jul. 17, 2006. The entire content of each application is expressly incorporated herein by reference thereto.

FIELD OF INVENTION

The present invention relates to peptide derivatives and analogs comprising the amino acid sequence of a fragment of mammalian histone H2A and to pharmaceutical compositions comprising same. The compositions of the invention are useful for treating inflammatory, autoimmune and degenerative diseases.

BACKGROUND OF THE INVENTION

The complete reduction of oxygen by the univalent pathway results in the formation of superoxide anion radical, hydrogen peroxide, and hydroxyl radical (OH) as intermediates. These intermediates are too reactive to be tolerated in living tissue, and a variety of enzymatic mechanisms, which can bypass the electron spin restriction of oxygen and accomplish the divalent and tetravalent reduction of oxygen to water have evolved. Thus, most of the oxygen consumed by respiring cells is utilized by cytochrome oxidase, which reduces oxygen to water without releasing either superoxide or hydrogen peroxide. Despite this, in respiring cells at least some reduction of oxygen occurs via the univalent pathway.

The presence of superoxide radicals, hydrogen peroxide, and hydroxyl radicals has been demonstrated in phagocytic cells including neutrophils and monocytes. It has been shown that the oxygen free radicals not only cause direct damage to membranes and DNA, but also exert indirect effects such as de-regulation of cell proliferation and apoptosis, stimulation of angiogenesis, and modification of gene/protein expression. The cellular enzymatic defense mechanism against superoxide and hydrogen peroxide includes superoxide dismutase (SOD), catalase, and glutathione peroxidase.

At present, the pathologies and diseases which may be attributable to oxygen free radicals are numerous and include neuronal diseases such as brain infarction, brain edema, Parkinson's disease, and Alzheimer's disease; multiple sclerosis; lung diseases such as lung oxygen intoxication, chronic bronchitis, and adult respiratory distress syndrome; circulatory system diseases such as ischemic heart diseases (e.g., myocardial infarction and arrhythmia), and arteriosclerosis; and digestive organ diseases such as peptic ulcer, ulcerative colitis, and Crohn's disease.

Attempts have been made to apply scavengers of oxygen free radicals to treat the above-mentioned diseases. For example, recombinant SOD has become available and has been administered to patients. Acute myocardial infarction is one of its target diseases.

The specific interactions of cells with the extracellular matrix also play a critical role in the normal function of organisms. Alterations of the extracellular matrix are carried out by a family of zinc-dependent endopeptidases called matrix metalloproteinases (MMPs). The alterations are carried out in various cellular processes such as organ development, ovulation, fetus implantation in the uterus, embryogenesis, wound healing, and angiogenesis.

MMPs consist of five major groups of enzymes: gelatinases, collagenases, stromelysins, membrane-type MMPs, and matrilysins. The activity of MMPs in normal tissue functions is strictly regulated by a series of complicated zymogen activation processes and inhibition by protein tissue inhibitors for matrix metalloproteinases ("TIMPs"). Over-expression and activation of MMPs or an imbalance between MMPs and TIMPs have been suggested as factors in the pathogenesis of diseases characterized by the breakdown of extracellular matrix or connective tissues, including diseases such as rheumatoid arthritis, osteoarthritis, osteoporosis, periodontitis, multiple sclerosis, gingivitis, corneal epidermal and gastric ulceration, atherosclerosis, neointimal proliferation which leads to restenosis and ischemic heart failure, and tumor metastasis (see, for example, Massova, I. et al. FASEB J. 1998, 12, 1075-1095). It has been suggested that these and other diseases may be treated by inhibiting metalloproteinase enzymes, thereby curtailing and/or eliminating the breakdown of connective tissues that results in the disease states.

The catalytic zinc in matrix metalloproteinases has been the focal point for inhibitor design. The modification of substrates by introducing zinc-chelating groups has generated potent inhibitors such as peptide and non-peptide hydroxamates and thiol-containing peptides. Peptide hydroxamates and the natural endogenous inhibitors of MMPs (TIMPs) have been used successfully to treat animal models of cancer and inflammation (see, for example, U.S. Pat. Nos. 5,300,501; 5,530,128; 5,455,258; and 5,552,419).

U.S. Pat. No. 6,468,537 and U.S. Patent Application Publication No. 2003/0021797 disclose peptides derived from nucleosomal histone proteins H1, H2A, H2B, H3, and H4, which are useful for delaying the onset and progression of systemic lupus erythematosus (SLE). U.S. Pat. No. 6,468,537 claims methods of treating an animal having systemic lupus erythematosus (SLE) and SLE-associated manifestations comprising administering to the animal one of the disclosed peptides, wherein the peptide is capable of promoting immunological tolerance, thereby treating SLE and the SLE-associated manifestations. While U.S. Pat. No. 6,468,537 discloses various peptides derived from different histones, among them a 15-mer peptide derived from H2A (amino acid residues 34 to 48), the peptides are disclosed solely as useful for promoting immunological tolerance in an animal having systemic lupus erythematosus.

International Patent Application Publication No. WO 03/017920 assigned to the applicant of the present invention discloses peptides for protection against inflammatory processes. The peptides were first isolated from the skin of a guinea pig exposed to a chemical or thermal burn and further exposed to iodine. One of the peptides is identified as a fragment of guinea pig histone H2A having the amino acid sequence corresponding to residues 36-44 of histone H2A, and designated peptide III. WO 03/017920 further discloses human homologues of peptide III including peptide 3 m1, analogs and derivatives thereof, mainly the methylated analogs. WO 03/017920 further discloses other peptides isolated from burned skin, the peptides correspond to fibrinopeptide A and derivatives thereof. The pharmaceutical compositions disclosed in WO 03/017920 are shown to protect against noxious insults and are suggested to be useful for treating inflammatory processes including autoimmune diseases.

None of the peptides disclosed in U.S. Pat. No. 6,468,537 and WO 03/017920 was known to be effective as a scavenger of free radicals or as a metal chelator.

There is still an unmet need for improved medicaments to treat inflammatory and autoimmune diseases, diseases attributable to oxygen free radicals, and diseases characterized by breakdown of the extracellular matrix or connective tissues.

SUMMARY OF THE INVENTION

The present invention provides peptides capable of reducing or ameliorating damage due to inflammatory processes including those due to thermal burns, chemical burns or other noxious stimuli. The present invention provides peptides capable of treating diseases attributable to inflammatory processes including autoimmune diseases such as arthritis and multiple sclerosis.

The present invention further provides peptides that scavenge free radicals and chelate metals. The peptides are effective for treating diseases attributable to the release of free radicals. The peptides are also effective for treating diseases or disorders attributable to the breakdown of extracellular matrix.

It is now disclosed for the first time that IIIM1 peptide having the amino acid sequence Lys-Gly-His-Tyr-Ala-Glu-Arg-Val-Gly (SEQ ID NO: 1) corresponding to the amino acid residues 36-44 of human histone H2A and homologous to the amino acid residues 36-44 of guinea pig histone H2A (SEQ ID NO: 2) is highly effective as a hydroxyl radical scavenger.

It is further disclosed that the protective effect of the IIIM1 peptide against a chemical insult is achieved regardless of whether the peptide is administered before or after the chemical insult occurs.

It is further disclosed that peptide IIIM1 is capable of treating arthritis and multiple sclerosis (MS) in animal models. The peptide is shown to be highly effective in reducing joint swelling in arthritic animals and in eliminating the neurological damages in multiple sclerotic animals. Peptide IIIM1 is also shown to effectively inhibit the manifestations of Parkinson's disease and to abrogate mortality due to sepsis.

Transfecting cells with a cDNA encoding a IIIM1 peptide derivative designated MIIIM1 peptide having the amino acid sequence Met-Lys-Gly-His-Tyr-Ala-Glu-Arg-Val-Gly as set forth in SEQ ID NO: 82, unexpectedly endows the cells with superior resistance against a chemical insult or other cytotoxic conditions. MIIIM1 peptide-transfected cells are shown herein below to be more viable and unexpectedly even more proliferative than non-transfected cells under the same chemical insults or cytotoxic conditions.

The present invention further provides fragments, extensions, substitutions, and chemical modifications of the IIIM1 peptide. The fragments, extensions, substitutions, and chemical modifications of the IIIM1 peptide are effective as anti-inflammatory agents. It is further disclosed that the IIIM1 peptide, fragments, extensions, substitutions, and chemical modifications thereof are effective as free radical scavengers. It should be understood that the fragments, extensions, substitutions, and chemical modifications of the IIIM1 peptide according to the principles of the present invention do not include the intact H2A protein or any known fragment thereof.

While the principles of the present invention are exemplified herein below in animal models, the invention is particularly useful for humans.

According to one aspect, the present invention provides a peptide of general formula I:

$$X_1-X_2-X_3-X_4-X_5-X_6-X_7-X_8-X_9 \qquad \text{SEQ ID NO: 3}$$
$$\text{I}$$

wherein $X_1$ is selected from the group consisting of Lys, carbobenzoxy-Lys, acetyl-Lys, Gln, and Arg; $X_2$ is selected from the group consisting of Gly, Ala, Sar, and Thr; $X_3$ is selected from the group consisting of His, MeHis, Benzyl-His, Asn, and Thr; $X_4$ is selected from the group consisting of Tyr, MeTyr, Tyr-O-Benzyl, and Ser; $X_5$ is selected from the group consisting of Ala, MeAla, Gly, Ser, and His; $X_6$ is selected from the group consisting of Glu, Glu-O-Benzyl, MeGlu, Gly and Gln; $X_7$ is selected from the group consisting of Arg, Arg-Tosyl, MeArg, and Lys; $X_8$ is selected from the group consisting of Val, MeVal, Leu, and Ile; and $X_9$ is selected from the group consisting of Gly, Gly-amide, Ala, and Sar; with the proviso that SEQ ID NOs: 1, 2 and 85 are excluded.

or a chemical derivative thereof;

wherein the peptide or chemical derivative has at least one activity selected from the group consisting of anti-inflammatory activity, free radical scavenging activity, metal chelating activity, metalloproteinase inhibitory activity, and T cell inhibitory activity.

According to some embodiments, the peptide has an amino acid sequence as set forth in any one of SEQ ID NO: 4 to SEQ ID NO: 42.

According to additional embodiments, the present invention provides a fragment of the peptide of general formula I:

$$X_1-X_2-X_3-X_4-X_5-X_6-X_7-X_8-X_9 \qquad \text{SEQ ID NO: 3}$$
$$\text{I}$$

wherein $X_1$ is absent or is selected from the group consisting of Lys, carbobenzoxy-Lys, acetyl-Lys, Gln, and Arg; $X_2$ is absent or is selected from the group consisting of Gly, Ala, Sar, and Thr; $X_3$ is absent or is selected from the group consisting of His, MeHis, Benzyl-His, Asn, and Thr; $X_4$ is absent or is selected from the group consisting of Tyr, MeTyr, Tyr-O-Benzyl, and Ser; $X_5$ is absent or is selected from the group consisting of Ala, MeAla, Gly, Ser, and His; $X_6$ is absent or is selected from the group consisting of Glu, Glu-O-Benzyl, MeGlu, Gly and Gln; $X_7$ is absent or is selected from the group consisting of Arg, Arg-Tosyl, MeArg, and Lys; $X_8$ is absent or is selected from the group consisting of Val, MeVal, Leu, and Ile; and $X_9$ is absent or is selected from the group consisting of Gly, Gly-amide, Ala, and Sar;

or a chemical derivative thereof;

wherein the fragment comprises at least four contiguous amino acid residues, and wherein said fragment has at least one activity selected from the group consisting of anti-inflammatory activity, free radical scavenging activity, metal chelating activity, metalloproteinase inhibitory activity, and T cell inhibitory activity.

According to some embodiments, the fragment comprises at least five contiguous amino acid residues. According to yet other embodiments, the fragment comprises at least six contiguous amino acid residues. According to further embodiments, the fragment comprises at least seven contiguous amino acid residues. According to additional embodiments, the fragment comprises at least eight contiguous amino acid residues.

According to some embodiments, the fragment has an amino acid sequence as set forth in any one of SEQ ID NO: 43-50, 52-55, 60-62, 64, and 65.

According to another aspect, the present invention provides a peptide of general formula II:

$$R_1-X_1-X_2-X_3-X_4-X_5-X_6-X_7-X_8-X_9-R_2 \quad \text{(SEQ ID NO: 66)}$$
II wherein $X_1$ is selected from the group consisting of Lys, carbobenzoxy-Lys, acetyl-Lys, Gln, and Arg; $X_2$ is selected from the group consisting of Gly, Ala, Sar, and Thr; $X_3$ is selected from the group consisting of His, MeHis, Benzyl-His, Asn, and Thr; $X_4$ is selected from the group consisting of Tyr, MeTyr, Tyr-O-Benzyl, and Ser; $X_5$ is selected from the group consisting of Ala, MeAla, Gly, Ser, and His; $X_6$ is selected from the group consisting of Glu, Glu-O-Benzyl, MeGlu, Gly and Gln; $X_7$ is selected from the group consisting of Arg, Arg-Tosyl, MeArg, and Lys; $X_8$ is selected from the group consisting of Val, MeVal, Ile, and Leu; $X_9$ is selected from the group consisting of Gly, Gly-amide, Ala, and Sar; $R_1$ is absent or is selected from the group consisting of Met, Arg, Leu-Arg, Leu-Leu-Arg, and Arg-Leu-Leu-Arg; and $R_2$ is absent or is selected from the group consisting of Ala, Ala-Gly, and Ala-Gly-Ala, wherein $R_1$ and $R_2$ cannot both be absent;

or a chemical derivative thereof;

wherein the peptide or chemical derivative has at least one activity selected from the group consisting of anti-inflammatory activity, free radical scavenging activity, metal chelating activity, metalloproteinase inhibitory activity, and T cell inhibitory activity.

According to some embodiments, the peptide of general formula II has an amino acid sequence as set forth in any one of SEQ ID NO: 67 to SEQ ID NO: 83.

According to another aspect, the present invention provides a peptide having the amino acid sequence KGHYAERVGC set forth in SEQ ID NO:90, or an analog, derivative, or fragment thereof, wherein the analog, derivative or fragment comprises at least four contiguous amino acid residues including the cysteine residue, said peptide, analog, derivative or fragment having at least one activity selected from the group consisting of anti-inflammatory activity, free radical scavenging activity, metal chelating activity, metalloproteinase inhibitory activity, and T-cell inhibitory activity. According to some embodiments, the analog, derivative or fragment comprises at least four amino acid residues, alternatively at least five, six, seven, eight, or nine amino acid residues, including the cysteine residue. According to a preferred embodiment, the isolated peptide has an amino acid sequence set forth in SEQ ID NO:90.

According to another aspect, the present invention provides an isolated polynucleotide sequence encoding a peptide derived from amino acid residues 36-44 of histone H2A having the amino acid sequence as set forth in any one of SEQ ID NOs: 1, 2 and 85, or a derivative or analog thereof, the peptide, derivative, or analog having at least one activity selected from the group consisting of anti-inflammatory activity, free radical scavenging activity, metal chelating activity, metalloprotease inhibitory activity, and T cell mediated activity. Preferably, the isolated polynucleotide encodes a peptide set forth in any one of SEQ ID NO: 1, 2, or 85. More preferably, the isolated polynucleotide encodes the peptide of SEQ ID NO: 1.

According to another aspect the present invention provides an isolated polynucleotide sequence encoding a peptide of general formula I or II according to the principles of the present invention, the peptide having at least one activity selected from the group consisting of anti-inflammatory activity, free radical scavenging activity, metal chelating activity, metalloproteinase inhibitory activity, and T cell inhibitory activity.

According to additional embodiments, the polynucleotide sequence encodes a peptide as set forth in any one of SEQ ID NO: 3 to SEQ ID NO: 83. In an exemplary embodiment, the isolated polynucleotide sequence has a nucleotide sequence as set forth in SEQ ID NO: 84. It should be understood that an isolated polynucleotide encodes only natural amino acid residues without any chemical modification. Chemical modifications of a peptide of the invention can occur only subsequent to peptide formation.

According to another aspect, the present invention provides an isolated polynucleotide sequence encoding a peptide having the amino acid sequence KGHYAERVGC set forth in SEQ ID NO:90, or an analog, derivative, or fragment thereof, wherein the analog, derivative or fragment comprises at least four contiguous amino acid residues including the cysteine residue, said peptide, analog, derivative or fragment having at least one activity selected from the group consisting of anti-inflammatory activity, free radical scavenging activity, metal chelating activity, metalloproteinase inhibitory activity, and T-cell inhibitory activity. According to a preferred embodiment, the isolated polynucleotide sequence encodes the peptide set forth in SEQ ID NO:90.

According to a further aspect, the present invention provides an expression vector comprising an isolated polynucleotide sequence encoding a peptide derived from amino acid residues 36-44 of histone H2A having the amino acid sequence as set forth in any one of SEQ ID NOs: 1, 2 and 85, or a derivative or analog thereof, the peptide, derivative, or analog having at least one activity selected from the group consisting of anti-inflammatory activity, free radical scavenging activity, metal chelating activity, metalloprotease inhibitory activity, and T cell inhibitory activity.

According to another aspect, the present invention provides an expression vector comprising an isolated polynucleotide sequence encoding a peptide of general formula I or II according to the principles of the present invention, the peptide having at least one activity selected from the group consisting of anti-inflammatory activity, free radical scavenging activity, metal chelating activity, metalloproteinase inhibitory activity, and T cell inhibitory activity.

According to some embodiments, the isolated polynucleotide within the expression vector encodes a peptide as set forth in any one of SEQ ID NO: 3 to SEQ ID NO: 83. In an exemplary embodiment, the isolated polynucleotide sequence having a nucleotide sequence as set forth in SEQ ID NO: 84.

According to another aspect, the present invention provides an expression vector comprising an isolated polynucleotide sequence encoding the peptide set forth in SEQ ID NO:90, or an analog, derivative, or fragment thereof, wherein the analog, derivative or fragment comprises at least four contiguous amino acid residues including the cysteine residue, said peptide, analog, derivative or fragment having at least one activity selected from the group consisting of anti-inflammatory activity, free radical scavenging activity, metal chelating activity, metalloproteinase inhibitory activity, and T-cell inhibitory activity. According to a preferred embodiment, the expression vector comprises an isolated polynucleotide sequence encoding the peptide set forth in SEQ ID NO:90.

According to yet another aspect, the present invention provides a host cell transfected with an expression vector comprising an isolated polynucleotide sequence encoding a peptide derived from amino acid residues 36-44 of histone H2A having the amino acid sequence as set forth in any one of SEQ ID NOs: 1, 2 and 85, or a derivative or analog thereof, the peptide, derivative, or analog having at least one activity selected from the group consisting of anti-inflammatory activity, free radical scavenging activity, metal chelating activity, metalloprotease inhibitory activity, and T cell inhibitory activity.

According to a further aspect, the present invention provides a host cell transfected with an expression vector comprising an isolated polynucleotide sequence encoding peptide of general formula I or II according to the principles of the present invention, the peptide having at least one activity selected from the group consisting of anti-inflammatory activity, free radical scavenging activity, metal chelating activity, metalloproteinase inhibitory activity, and T cell inhibitory activity.

According to another aspect, the present invention provides a host cell comprising an expression vector comprising an isolated polynucleotide sequence encoding the peptide set forth in SEQ ID NO:90, or an analog, derivative, or fragment thereof, wherein the analog, derivative or fragment comprises at least four contiguous amino acid residues including the cysteine residue, said peptide, analog, derivative or fragment having at least one activity selected from the group consisting of anti-inflammatory activity, free radical scavenging activity, metal chelating activity, metalloproteinase inhibitory activity, and T-cell inhibitory activity. According to a preferred embodiment, the host cell comprises an expression vector comprising an isolated polynucleotide sequence encoding the peptide set forth in SEQ ID NO:90.

According to additional embodiments, the host cell is selected from the group consisting of a prokaryotic cell, a eukaryotic cell, and a plant cell.

According to another aspect, the present invention provides a pharmaceutical composition comprising as an active ingredient a peptide or a chemical derivative thereof having an amino acid sequence of general formula I or II according to the principles of the present invention; and a pharmaceutically acceptable carrier.

According to a further aspect, the present invention provides a pharmaceutical composition comprising as an active ingredient an isolated peptide having the amino acid sequence KGHYAERVGC set forth in SEQ ID NO:90, or an analog, derivative, or fragment thereof, wherein the analog, derivative or fragment comprises at least four contiguous amino acid residues including the cysteine residue, said peptide, analog, derivative or fragment having at least one activity selected from the group consisting of anti-inflammatory activity, free radical scavenging activity, metal chelating activity, metalloproteinase inhibitory activity, and T-cell inhibitory activity; and a pharmaceutically acceptable carrier. According to a preferred embodiment, the pharmaceutical composition comprises as an active ingredient the peptide set forth in SEQ ID NO:90 and a pharmaceutically acceptable carrier. According to some embodiments, the pharmaceutical composition comprising a peptide of the invention is formulated for parenteral administration. According to additional embodiments, the pharmaceutical composition comprising a peptide of the invention is formulated for oral administration.

According to yet further aspect, the present invention provides a pharmaceutical composition comprising as an active ingredient an isolated polynucleotide sequence encoding a peptide as set forth in any one of SEQ ID NO: 1, 2, and 85, or a derivative or analog thereof, the peptide, derivative or analog having at least one activity selected from the group consisting of anti-inflammatory activity, free radical scavenging activity, metal chelating activity, metalloproteinase inhibitory activity, and T cell inhibitory activity.

According to another aspect, the present invention provides a pharmaceutical composition comprising as an active ingredient an isolated polynucleotide sequence encoding a peptide of general formula I or II according to the principles of the invention and a pharmaceutically acceptable carrier.

According to yet further aspect, the present invention provides a pharmaceutical composition comprising as an active ingredient an isolated polynucleotide sequence encoding the peptide set forth in SEQ ID NO:90, or an analog, fragment or derivative thereof; and a pharmaceutically acceptable carrier. Preferably the pharmaceutical composition comprises an isolated polynucleotide sequence encoding the peptide set forth in SEQ ID NO:90 and a pharmaceutically acceptable carrier.

According to a further aspect, the present invention provides a pharmaceutical composition comprising as an active ingredient an expression vector according to the principles of the invention and a pharmaceutically acceptable carrier.

According to another aspect the present invention provides a pharmaceutical composition comprising as an active ingredient an expression vector comprising an isolated polynucleotide sequence encoding the peptide set forth in SEQ ID NO:90, or an analog, fragment or derivative thereof, and a pharmaceutically acceptable carrier. Preferably, the pharmaceutical composition comprises as an active ingredient an expression vector comprising an isolated polynucleotide sequence encoding the peptide set forth in SEQ ID NO:90 and a pharmaceutically acceptable carrier.

According to yet another aspect, the present invention provides a pharmaceutical composition comprising as an active ingredient a host cell transfected with an expression vector according to the principles of the invention and a pharmaceutically acceptable carrier.

According to a further aspect, the present invention provides a pharmaceutical composition comprising as an active ingredient a host cell comprising an expression vector comprising an isolated polynucleotide sequence encoding the peptide set forth in SEQ ID NO:90, or an analog, fragment or derivative thereof, and a pharmaceutically acceptable carrier. Preferably, the pharmaceutical composition comprises a host cell comprising an expression vector comprising an isolated polynucleotide sequence encoding the peptide set forth in SEQ ID NO:90 and a pharmaceutically acceptable carrier.

According to another aspect, the present invention provides a method for protecting against or treating tissue damage consequent to a noxious insult in a subject comprising administering to the subject in need thereof a therapeutically effective amount of a pharmaceutical composition according to the principles of the present invention. Preferably, the subject is a human. According to exemplary embodiments, the pharmaceutical composition comprises a peptide having an amino acid sequence as set forth in SEQ ID NO:1 or SEQ ID NO:90. According to some embodiments, the route of administering the pharmaceutical composition comprising a peptide of the invention is by parenteral administration. According to additional embodiments, the route of administering the pharmaceutical composition comprising a peptide of the invention is by oral administration.

According to some embodiments, the noxious insults include, but are not limited to, heat stimuli, cold stimuli, chemical stimuli, electric stimuli, ultraviolet irradiation, ionizing radiation, non-ionizing irradiation, and ultrasound.

According to another aspect, the present invention provides a method for treating a disease or condition attributable to inflammation comprising administering to the subject in need thereof a therapeutically effective amount of a pharmaceutical composition according to the principles of the present invention. Preferably, the subject is a human. According to exemplary embodiments, the pharmaceutical composition comprises a peptide having an amino acid sequence as is set forth in SEQ ID NO:1 or SEQ ID NO:90. Preferably, the route of administering the pharmaceutical composition is by parenteral administration. More preferably, the route of administering the pharmaceutical composition is by oral administration.

Due to their anti-inflammatory properties, the pharmaceutical compositions of the present invention are useful for treating a diverse group of indications having an inflammatory or autoimmune mechanism involved in their etiology or pathogenesis. According to some embodiments, the disease or condition is selected from the group consisting of wounds, hypersensitivity, autoimmune diseases, degenerative neurological diseases, degenerative muscle diseases, infectious diseases, diseases associated with graft transplantation, allergic diseases, musculo-skeletal inflammations, and sepsis.

According to additional embodiments, the disease is selected from the group consisting of psoriasis, systemic lupus erythematosus (SLE), multiple sclerosis, inflammatory bowel disease (Crohn's disease), arthritis including rheumatoid arthritis, asthma, chronic bronchitis, amyotrophic lateral sclerosis, Parkinson's disease, Alzheimer's disease, muscular dystrophy, and sepsis. According to a currently exemplary embodiment, the disease to be treated is multiple sclerosis. According to another currently exemplary embodiment, the disease to be treated is Parkinson's disease. According to a further exemplary embodiment, the condition to be treated is sepsis.

According to a further aspect, the present invention provides a method for scavenging free radicals in a subject comprising administering to a subject in need thereof a therapeutically effective amount of a pharmaceutical composition comprising as an active ingredient a peptide having an amino acid sequence as set forth in any one of SEQ ID NOs: 1, 2 and 85, or a peptide derivative or analog thereof, and a pharmaceutically acceptable carrier.

According to yet further aspect, the present invention provides a method for scavenging free radicals in a subject comprising administering to a subject in need thereof a therapeutically effective amount of a pharmaceutical composition according to the principles of the present invention, and a pharmaceutically acceptable carrier. According to some embodiments, the pharmaceutical composition to be administered for scavenging free radicals in a subject comprises a peptide having an amino acid sequence as set forth in SEQ ID NO:1 or SEQ ID NO:90. Preferably, the subject is human, though plants are encompassed within the present application.

According to some embodiments, the free radicals are reactive oxygen species (ROS) selected from the group consisting of superoxide radicals, hydrogen peroxide, and hydroxyl radicals. According to additional embodiments, the free radicals are carbon tetra chloride radicals. It will be appreciated that the peptides of the present invention are capable of scavenging other toxic radicals as are known in the art.

According to another aspect, the present invention provides a method for protecting against or treating a disease or condition attributable to free radicals in a subject comprising administering to the subject in need thereof a therapeutically effective amount of a pharmaceutical composition comprising as an active ingredient a peptide having an amino acid sequence as set forth in any one of SEQ ID NOs: 1, 2 and 85, or a peptide derivative or peptide analog thereof, and a pharmaceutically acceptable carrier.

According to another aspect, the present invention provides a method for protecting against or treating a disease or condition attributable to free radicals in a subject comprising administering to the subject in need thereof a therapeutically effective amount of a pharmaceutical composition according to the principles of the present invention, and a pharmaceutically acceptable carrier. According to some embodiments, the pharmaceutical composition to be administered for protecting against or treating a disease or condition attributable to free radicals in a subject comprises a peptide having an amino acid sequence as set forth in SEQ ID NO:1 or SEQ ID NO:90. Preferably, the subject is human.

According to some embodiments, the free radicals are reactive oxygen species selected from the group consisting of superoxide radicals, hydrogen peroxide, and hydroxyl radicals. Preferably, the subject to be treated is a human.

According to other embodiments, the disease or condition attributable to reactive oxygen species to be treated by the pharmaceutical compositions of the invention are selected from the group consisting of neuronal diseases, lung diseases, cardiovascular diseases, and digestive organ diseases.

According to additional embodiments, the disease or condition attributable to free radicals is selected from the group consisting of brain infarction, brain edema, Parkinson's disease, Alzheimer's disease, multiple sclerosis, lung oxygen intoxication, chronic bronchitis, adult respiratory distress syndrome, ischemic diseases (e.g., myocardial infarction and arrhythmia), arteriosclerosis, peptic ulcer, ulcerative colitis, and Crohn's disease. It will be appreciated that biological damages caused by infections can also be treated with the pharmaceutical compositions of the invention.

According to a further aspect, the present invention provides a method for protecting against or treating a disease or pathological condition attributable to altered metalloproteinase (MMP) activity in a subject comprising administering to the subject in need thereof a therapeutically effective amount of a pharmaceutical composition comprising as an active ingredient a peptide having an amino acid sequence as set forth in any one of SEQ ID NOs: 1, 2 and 85, or a peptide derivative, or peptide analog thereof, and a pharmaceutically acceptable carrier.

According to a further aspect, the present invention provides a method for protecting against or treating a disease or pathological condition attributable to altered MMP activity in a subject comprising administering to the subject in need thereof a therapeutically effective amount of a pharmaceutical composition according to the principles of the present invention, and a pharmaceutically acceptable carrier. According to some embodiments, the pharmaceutical composition to be administered for protecting against or treating a disease or pathological condition attributable to altered MMP activity in a subject comprises a peptide as set forth in SEQ ID NO:1 or SEQ ID NO:90. Preferably, the subject is human.

According to some embodiments, the disease or pathological condition which are attributable to MMP activity are selected from the group consisting of multiple sclerosis, atherosclerosis, restenosis, aortic aneurysm, cardiovascular disease, periodontal disease, corneal ulceration, burns, decubital ulcers, chronic ulcers or wounds including gastric ulcers, osteoporosis, rheumatoid arthritis, osteoarthritis, renal disease, neurological disorders, or any other connective tissue disease.

According to another aspect, the present invention provides a method for protecting against or treating a condition attributed to metal poisoning in a subject comprising administering to a subject in need thereof a therapeutically effective amount of a pharmaceutical composition comprising as an active ingredient a peptide as set forth in any one of SEQ ID NOs: 1, 2 and 85, or a peptide derivative or peptide analog thereof, and a pharmaceutically acceptable carrier.

According to another aspect, the present invention provides a method for protecting against or treating a condition attributed to metal poisoning in a subject comprising administering to a subject in need thereof a therapeutically effective amount of a pharmaceutical composition according to the principles of the present invention. According to some embodiments, the pharmaceutical composition to be administered for protecting against or treating a condition attributed to metal poisoning in a subject comprises a peptide as set forth in SEQ ID NO:1 or SEQ ID NO:90. Preferably, the subject is human.

According to another aspect, the present invention provides a method for protecting against or treating a T cell mediated disease comprising administering to the subject in need thereof a therapeutically effective amount of a pharmaceutical composition comprising as an active ingredient a peptide as set forth in any one of SEQ ID NOs: 1, 2 and 85, or a peptide derivative, or analog thereof, and a pharmaceutically acceptable carrier.

According to a further aspect, the present invention provides a method for protecting against or treating a T cell mediated disease comprising administering to the subject in need thereof a therapeutically effective amount of a pharmaceutical composition according to the principles of the present invention, and a pharmaceutically acceptable carrier. According to some embodiments, the pharmaceutical composition to be administered for protecting against or treating a T cell mediated disease in a subject comprises a peptide as set forth in SEQ ID NO:1 or SEQ ID NO:90. Preferably, the subject is human.

According to some embodiments, T cell mediated disease that can be treated by a pharmaceutical composition of the invention is selected from the group consisting of psoriasis; allergy; T cell lymphomas and other malignancies; graft versus host disease; prevention of transplant rejection; bronchitis; asthma; autoimmunity; sarcoidosis; bone marrow depression; bone marrow stimulation; depression or other mood or psychotic disorders; sepsis; Parkinson's disease; skin disorders and irritation; arthritis; multiple sclerosis; neurodegenerative disorders (amyotrophic lateral sclerosis, chorea, Alzheimer disease); atherosclerosis; fibrosis; pain; chronic or acute inflammation. The peptides and pharmaceutical compositions of the present invention can be used in combination therapy with standard medicaments for the diseases listed herein above.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

FIG. 11A shows the protective effect of a single peptide treatment against SM-induced skin lesions. FIGS. 11B-C show the protective effect of multiple peptide treatments against SM-induced skin lesions.

DETAILED DESCRIPTION OF THE PREFERRED EMBODIMENTS

Figure 1:
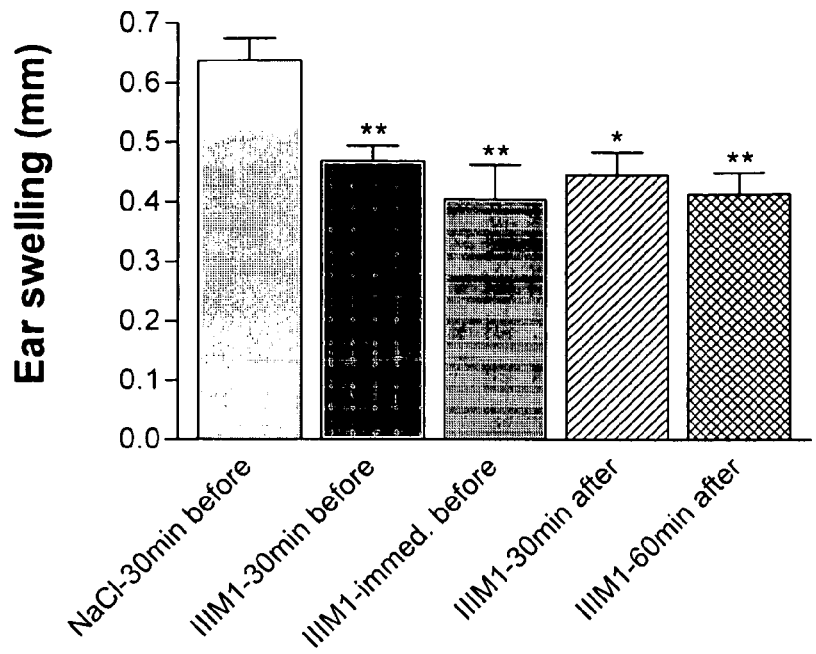
FIG. 1 shows the protective effect of peptide IIIM1 against sulphur mustard (SM)-induced chemical burns by pre- or post-exposure treatments.

The present invention relates to a peptide designated IIIM1 having the sequence of amino acid residues 36 to 44 of human histone H2A. The present invention further relates to analogs, derivatives and fragments of peptide IIIM1 having at least one activity selected from the group consisting of anti-inflammatory activity, free radical scavenging activity, metal chelating activity, and metalloprotease inhibitory activity. Thus, the peptides of the invention are useful for treating or protecting a subject against noxious stimuli, inflammatory conditions and diseases, diseases associated with free radicals, and diseases associated with altered metalloproteinase activity.

As contemplated herein, the present invention demonstrates that administration of peptide IIIM1, analogs, derivatives or fragments thereof as described herein reduce the degree of inflammatory processes induced by noxious stimuli. The peptides of the present invention are also capable of scavenging oxygen free radicals and hence can prevent or reduce biological damage caused by free oxygen radicals, particularly hydroxyl radicals. Additionally, the peptides of the present invention are capable of chelating metals, and hence can inhibit the activity of metalloproteinases. The peptides of the present invention are, therefore, useful for treating diseases such as inflammatory, autoimmune, neurological, cardiovascular, and connective tissue diseases.

The inventor of the present application has previously disclosed in WO 03/017920 a series of peptides derived from human and guinea pig histone H2A corresponding to amino acid residues 36-44 of histone H2A. WO 03/017920 further discloses Fibrinopeptide A and peptide derivatives thereof. The H2A and fibrinopeptide A peptides were shown to be produced in skin upon heat or chemical stimuli followed by topical treatment with iodine preparation. Administration of the peptides disclosed in WO 03/017920 to naïve animals and subsequent exposure of the animals to noxious stimuli was shown in WO 03/017920 to significantly reduce skin damage in the treated animals.

U.S. Pat. No. 6,468,537 and WO 03/017920 disclose the following peptides derived from histone H2A:

| Synthetic Peptide | Amino acid Sequence | Designation | SEQ ID | Reference |
|---|---|---|---|---|
| H2A 34-48 | LRKGNYAERVGAGAP | | 89 | U.S. Pat. No. 6,468,537 |
| H2A 36-44 (gp)* | KGNYAERIA | Peptide III | 2 | WO 03/017920 |
| H2A 36-44 (h)** | KGNYAERVG | | 86 | " |
| H2A 36-44 (h) | KGNYSERVG | Peptide 3m | 85 | " |
| H2A 36-44 (h) | KAHYSERVG | | 87 | " |
| H2A 36-44 (h) | KGHYAERVG | Peptide IIIM1 | 1 | " |
| H2A 36-44 (h) | KSRTTSHGRVG | | 88 | " |

*gp- guinea pig;
**h- human.

The present invention discloses new peptide derivatives or analogs of a peptide comprising amino acid residues 36-44 of human histone H2A or fragments thereof, the peptide designated IIIM1 has the amino acid sequence Lys-Gly-His-Tyr-Ala-Glu-Arg-Val-Gly as set forth in SEQ ID NO: 1.

The term "peptide" as used herein refers to a linear series of natural, non-natural and/or chemically modified amino acid residues connected one to the other by peptide bonds. The amino acid residues are represented throughout the specification and claims by either one or three-letter codes, as is commonly known in the art.

The terms "analog" and "derivative" refer to a peptide comprising at least one altered amino acid residue by an amino acid substitution, addition, deletion, or chemical modification, as compared with the native peptide. Peptide derivatives particularly include amino acid substitutions and/or additions with naturally occurring amino acid residues, and chemical modifications such as, for example, enzymatic modifications, typically present in nature. Peptide analogs particularly include amino acid substitutions and/or additions with non-natural amino acid residues, and chemical modifications, which do not occur in nature. Thus, the present invention encompasses both peptide derivatives and analogs of the IIIM1 peptide as set forth in SEQ ID NO: 1. According to the principles of the present invention the peptide derivatives or analogs of IIIM1 peptide do not include the intact H2A protein or any known fragments thereto.

By using "amino acid substitutions", it is meant that functionally equivalent amino acid residues are substituted for residues within the sequence resulting in a silent change. The term "functionally equivalent" means, for example, a group of amino acids having similar polarity, similar charge, or similar hydrophobicity. For example, one or more amino acid residues within the sequence can be substituted by another amino acid of a similar polarity, which acts as a functional equivalent, resulting in a silent alteration. Substitutes for an amino acid within the sequence can be selected from other members of the class to which the amino acid belongs. For example, the non-polar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such substitutions are known as conservative substitutions. Additionally, a non-conservative substitution can be made in an amino acid that does not contribute to the biological activity of the peptide. Such non-conservative substitutions are also encompassed within the term "amino acid substitution", as used herein. It will be appreciated that the present invention further encompasses peptide IIIM1 derivatives or analogs, wherein at least one amino acid is substituted by another amino acid to produce a peptide derivative or analog having increased stability or higher half life as compared to the native peptide IIIM1.

The present invention encompasses peptides of which at least one amino acid has been chemically modified. Chemical modifications of amino acid residues include, but are not limited to, amidation, methylation, acetylation, glycosylation, oxidation, reduction, myristylation, sulfation, acylation, ADP-ribosylation, cyclization, hydroxylation, iodination, derivatization by protecting/blocking groups, or any other derivatization method known in the art. Such alterations, which do not destroy, but may improve the peptide IIIM1 biological activity can occur anywhere along the sequence of the peptide IIIM1, including at the peptide backbone, the amino acid side-chains, and at the amino or carboxyl termini.

The term "fragment" as used herein refers to a portion of a peptide, peptide derivative or peptide analog having at least one biological activity selected from the group consisting of anti-inflammatory activity, free radical scavenging activity, metal chelating activity, and metalloproteinase inhibitory activity.

The present invention encompasses peptide hydrates. The term "hydrate" includes, but is not limited to, hemihydrate, monohydrate, dihydrate, trihydrate, and the like.

Peptide IIIM1 and analogs, derivatives and fragments thereof can be produced by various methods known in the art, including recombinant production or synthetic production. Recombinant production can be achieved by the use of an isolated polynucleotide encoding peptide IIIM1, or a fragment, derivative or analog thereof, the isolated polynucleotide operably linked to a promoter for the expression of the polynucleotide. Optionally, a signal peptide and a regulator of the promoter are added. The construct comprising the polynucleotide encoding the peptide IIIM1, or a fragment, derivative or analog thereof, the promoter, and optionally the regulator can be placed in a vector, such as a plasmid, virus or phage vector. The vector can be used to transfect or transform a host cell, e.g., a bacterial, yeast, insect, or mammalian cell. The vector can also be introduced into a transgenic animal such as, for example, a transgenic mouse.

Alternatively, the peptide can by produced synthetically. Synthetic production of peptides is well known in the art. The IIIM1 peptide, derivatives, analogs and/or fragments thereof can be synthesized using standard direct peptide synthesis (see, for example, Bodanszky, 1984, Principles of Peptide Synthesis, Springer-Verlag, Heidelberg), such as via solid-phase synthesis (see, for example, Merrifield, 1963, J. Am. Chem. Soc. 85:2149-2154, the contents of which are hereby incorporated by reference in their entirety). Examples of solid phase peptide synthesis methods include, but are not limited to, the BOC method, which utilizes tert-butyloxcarbonyl as the α-amino protecting group, and the FMOC method, which utilizes 9-fluorenylmethyloxcarbonyl to protect the α-amino of the amino acid residues, both methods are well-known by those of skill in the art.

Alternatively, the peptide derivatives, analogs, and fragments of the present invention can be synthesized using standard solution methods (see, for example, Bodanszky, M., Principles of Peptide Synthesis, Springer-Verlag, 1984, the content of which is hereby incorporated by reference in its entirety).

The peptide derivatives, analogs, and fragments according to the principles of the present invention can also include side chain bond modifications, including but not limited to —$CH_2$—NH—, —$CH_2$—S—, —$CH_2$—S=O, O=C—NH—, —$CH_2$—O—, —$CH_2$—$CH_2$—, S=C—NH—, and —CH=CH—, and backbone modifications such as modified peptide bonds. Peptide bonds (—CO—NH—) within the peptide can be substituted, for example, by N-methylated bonds (—N(CH3)-CO—); ester bonds (—C(R)H—C—O—O—C(R)H—N); ketomethylene bonds (—CO—CH2-); α-aza bonds (—NH—N(R)—CO—), wherein R is any alkyl group, e.g., methyl; carba bonds (—CH2-NH—); hydroxyethylene bonds (—CH(OH)—CH2-); thioamide bonds (—CS—NH); olefinic double bonds (—CH=CH—); and peptide derivatives (—N(R)—CH2-CO—), wherein R is the "normal" side chain, naturally presented on the carbon atom. These modifications can occur at one or more of the bonds along the peptide chain and even at several (e.g., 2-3) at the same time.

The present invention also encompasses peptide derivatives and analogs in which free amino groups have been derivatized to form amine hydrochlorides, p-toluene sulfonylamino groups, carbobenzoxyamino groups, t-butyloxycarbonylamino groups, chloroacetylamino groups or formylamino groups. Free carboxyl groups may be derivatized to form, for example, salts, methyl and ethyl esters or other types of esters or hydrazides. The imidazole nitrogen of histidine can be derivatized to form N-im-benzylhistidine.

Also included are those peptide derivatives, which contain one or more naturally occurring amino acid derivatives of the twenty standard amino acid residues. For example: 4-hydroxyproline can be substituted for proline; 5-hydroxylysine can be substituted for lysine; 3-methylhistidine can be substituted for histidine; homoserine can be substituted or serine; and ornithine can be substituted for lysine. The peptide analogs can also contain non-natural amino acids. Examples of non-natural amino acids include, but are not limited to, sarcosine (Sar), norleucine, ornithine, citrulline, diaminobutyric acid, homoserine, isopropyl Lys, 3-(2'-naphtyl)-Ala, nicotinyl Lys, amino isobutyric acid, and 3-(3'-pyridyl-Ala).

Furthermore, the peptide analogs can contain other derivatized amino acid residues including, but not limited to, methylated amino acids, N-benzylated amino acids, O-benzylated amino acids, N-acetylated amino acids, O-acetylated amino acids, carbobenzoxy-substituted amino acids and the like. Specific examples include, but are not limited to, methyl-Ala (MeAla), MeTyr, MeArg, MeGlu, MeVal, MeHis, N-acetyl-Lys, O-acetyl-Lys, carbobenzoxy-Lys, Tyr-O-Benzyl, Glu-O-Benzyl, Benzyl-His, Arg-Tosyl, t-butylglycine, t-butylalanine, phenylglycine, cyclohexylalanine, and the like.

The invention further includes peptide IIIM1 analogs, which can contain one or more D-isomer forms of the amino acids. Production of retro-inverso D-amino acid peptides where at least one amino acid, and perhaps all amino acids, is D-amino acids is well known in the art. When all of the amino acids in the peptide are D-amino acids, and the N- and C-terminals of the molecule are reversed, the result is a molecule having the same structural groups being at the same positions as in the L-amino acid form of the molecule. However, the molecule is more stable to proteolytic degradation and is therefore useful in many of the applications recited herein.

Included within the scope of the invention are peptide conjugates comprising a IIIM1 peptide derivative, analog, or fragment thereof joined at its amino or carboxy-terminus or at one of the side chains via a peptide bond to an amino acid sequence of a different protein. Additionally or alternatively, a IIIM1 peptide derivative, analog, or fragment thereof can be joined to another moiety such as, for example, a fatty acid, a sugar moiety, arginine residues, and any known moiety that facilitate membrane or cell penetration. Conjugates comprising peptides of the invention and a protein can be made by protein synthesis, e.g., by use of a peptide synthesizer, or by ligating the appropriate nucleic acid sequences encoding the desired amino acid sequences to each other by methods known in the art, in the proper coding frame, and expressing the conjugate by methods commonly known in the art.

Thus, in one aspect, the present invention provides a peptide of general formula I:

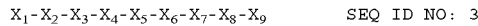
$X_1 - X_2 - X_3 - X_4 - X_5 - X_6 - X_7 - X_8 - X_9$         SEQ ID NO: 3 wherein $X_1$ is selected from the group consisting of Lys, carbobenzoxy-Lys, acetyl-Lys, Gln, and Arg; $X_2$ is selected from the group consisting of Gly, Ala, Sar, and Thr; $X_3$ is selected from the group consisting of His, MeHis, Benzyl-His, Asn, and Thr; $X_4$ is selected from the group consisting of Tyr, MeTyr, Tyr-O-Benzyl, and Ser; $X_5$ is selected from the group consisting of Ala, MeAla, Gly, Ser, and His; $X_6$ is selected from the group consisting of Glu, Glu-O-Benzyl, MeGlu, Gly and Gln; $X_7$ is selected from the group consisting of Arg, Arg-Tosyl, MeArg, and Lys; $X_8$ is selected from the group consisting of Val, MeVal, Leu, and Ile; and $X_9$ is selected from the group consisting of Gly, Gly-amide, Ala, and Sar; with the proviso that the peptide set forth in SEQ ID NOs: 1, 2 and 85 are excluded.

or a chemical derivative thereof;

wherein the peptide or chemical derivative has at least one activity selected from the group consisting of anti-inflammatory activity, free radical scavenging activity, metal chelating activity, metalloproteinase inhibitory activity, and T cell inhibitory activity.

According to some non-limiting exemplary embodiments, the peptide has the amino acid sequence as set forth in any one of SEQ ID NO:4 to SEQ ID NO:42 as follows (the designation of the peptides is indicated in parentheses):

```
                                            SEQ ID NO: 4
H-Lys-Gly-His-Tyr-Ala-Glu-Arg-Val-Gly-NH2 (IIIM1-
amide);

SEQ ID NO: 5
H-Ac-Lys-Gly-His-Tyr-Ala-Glu-Arg-Val-Gly-OH (IIIM1
Acetyl-Lys);

SEQ ID NO: 6
Ac-Lys-Gly-His-Tyr-Ala-Glu-Arg-Val-Gly-NH2
(Acetyl-Lys IIIM1-amide);

SEQ ID NO: 7
Z-Lys-Gly-His-Tyr-Ala-Glu-Arg-Val-Gly-OH (IIIM1
carbobenzoxy-Lys);

SEQ ID NO: 8
H-Lys-Gly-MeHis-MeTyr-Ala-Glu-Arg-Val-Gly-OH (P4);

SEQ ID NO: 9
H-Lys-Gly-His-Tyr-MeAla-Glu-Arg-Val-Gly-OH (MeAla
IIIM1);

SEQ ID NO: 10
H-Lys-Gly-His-MeTyr-Ala-Glu-Arg-Val-Gly-OH (IIIM1-
MeTyr);

SEQ ID NO: 11
H-Lys-Gly-His-Tyr-Ala-Glu-MeArg-Val-Gly-OH (IIIM1
N-MeArg);

SEQ ID NO: 12
H-Lys-Gly-His-Tyr-Ala-MeGlu-Arg-Val-Gly-OH (IIIM1
N-MeGlu);

SEQ ID NO: 13
H-Lys-Gly-His-Tyr-Ala-Glu-Arg-MeVal-Gly-OH (IIIM1-
N-Methyl-Val8);

SEQ ID NO: 14
H-Lys-Sar-His-Tyr-Ala-Glu-Arg-Val-Gly-OH (IIIM1-
Sar2);

SEQ ID NO: 15
H-Lys-Gly-His-Tyr-Ala-Glu-Arg-Val-Sar-OH (IIIM1-
Sar9);

SEQ ID NO: 16
H-Lys-Sar-His-Tyr-Ala-Glu-Arg-Val-Sar-OH (IIIM1-
Sar2 Sar9);

SEQ ID NO: 17
H-Lys-Gly-His-MeTyr-Ala-Glu-Arg-Val-Gly-NH2
(IIIM1-MeTyr-amide);

SEQ ID NO: 18
H-Lys-Gly-MeHis-Tyr-Ala-Glu-Arg-Val-Gly-NH2
(IIIM1-MeHis-amide);

SEQ ID NO: 19
H-Lys-Sar-His-Tyr-Ala-Glu-Arg-Val-Gly-NH2 (IIIM1-
Sar2-amide);

SEQ ID NO: 20
H-Lys-Sar-MeHis-MeTyr-Ala-Glu-Arg-Val-Gly-OH
(IIIM1-Sar2-MeHis-MeTyr);

SEQ ID NO: 21
H-Lys-Sar-MeHis-Tyr-Ala-Glu-Arg-Val-Gly-OH (IIIM1-
Sar2-MeHis);

SEQ ID NO: 22
H-Lys-Sar-His-MeTyr-Ala-Glu-Arg-Val-Gly-OH (IIIM1-
Sar2-MeTyr);

SEQ ID NO: 23
H-Lys-Sar-His-Tyr-Ala-Glu-Arg-MeVal-Gly-OH (IIIM1-
Sar2, N-Methyl-Val8);

SEQ ID NO: 24
H-Lys-Gly-His-Tyr-Ala-Glu-Arg-MeVal-Sar-OH (IIIM1-
N-Methyl-Val8, Sar9);
```

-continued

```
                                          SEQ ID NO: 25
H-Lys-Sar-His-Tyr-Ala-Glu-Arg-MeVal-Sar-OH (IIIM1,
Sar2, N-Methyl-Val8, Sar9);

SEQ ID NO: 26
H-Lys-Sar-His-Tyr-MeAla-Glu-Arg-Val-Gly-OH (IIIM1-
Sar2, MeAla5);

SEQ ID NO: 27
H-Lys-Sar-His-MeTyr-Ala-Glu-Arg-Val-Gly-NH2
(IIIM1-Sar2-MeTyr-amide);

SEQ ID NO: 28
H-Lys-Ala-His-Tyr-Ala-Glu-Arg-Val-Gly-OH (IIIU2);

SEQ ID NO: 29
H-Lys-Ala-Asn-Tyr-Ala-Glu-Arg-Val-Gly-OH (IIIU3);

SEQ ID NO: 30
H-Lys-Gly-His-Tyr-Ser-Glu-Arg-Val-Gly-OH (IIIU1);

SEQ ID NO: 31
H-Lys-Gly-Asn-Tyr-Ala-Glu-Arg-Val-Gly-OH (IIIH);

SEQ ID NO: 32
H-Lys-Ala-Asn-Tyr-MeAla-Glu-Arg-Val-Gly-OH (MeAla
IIIU3);

SEQ ID NO: 33
H-Lys-Ala-His-Tyr-MeAla-Glu-Arg-Val-Gly-OH
(MeAlaIIIU2);

SEQ ID NO: 34
H-Lys-Gly-His-Tyr(O-Bz)-Ala-Glu-Arg-Val-Gly-OH
(IIIM1 Tyr-O-Benzyl);

SEQ ID NO: 35
H-Lys-Gly-His-Tyr-Ala-Glu(O-Bz)-Arg-Val-Gly-OH
(IIIM1 Glu-O-Benzyl);

SEQ ID NO: 36
H-Lys-Gly-(Bz)His-Tyr-Ala-Glu-Arg-Val-Gly-OH
(IIIM1 Benzyl-His);

SEQ ID NO: 37
H-Lys-Gly-His-Tyr-Ala-Glu-Arg(Tos)-Val-Gly-OH
(IIIM1 Arg-Tosyl);

SEQ ID NO: 38
Ac-Lys-Gly-His(Bz)-Tyr(O-Bz)-Ala-Glu(O-Bz)-Arg
(Tos)-Val-Gly-NH2 (IIIM1-plus all
blocking groups);

SEQ ID NO: 39
H-Lys-Gly-His-Tyr-Ala-Glu-Lys-Val-Gly-OH;

SEQ ID NO: 40
H-Lys-Gly-His-Tyr-Ala-Gln-Lys-Val-Gly-OH;

SEQ ID NO: 41
H-Gln-Gly-Asn-Tyr-Ala-Glu-Arg-Ile-Gly-OH;

SEQ ID NO: 42
H-Arg-Thr-Thr-Ser-His-Gly-Arg-Val-Gly-OH.
```

The present invention further provides a fragment of the peptide of general formula I:

$$X_1-X_2-X_3-X_4-X_5-X_6-X_7-X_8-X_9 \quad \text{SEQ ID NO: 3}$$
$$\text{I}$$

wherein $X_1$ is absent or is selected from the group consisting of Lys, carbobenzoxy-Lys, acetyl-Lys, Gln, and Arg; $X_2$ is absent or is selected from the group consisting of Gly, Ala, Sar, and Thr; $X_3$ is absent or is selected from the group consisting of His, MeHis, Benzyl-His, Asn, and Thr; $X_4$ is absent or is selected from the group consisting of Tyr, MeTyr, Tyr-O-Benzyl, and Ser; $X_5$ is absent or is selected from the group consisting of Ala, MeAla, Gly, Ser, and His; $X_6$ is absent or is selected from the group consisting of Glu, Glu-O-Benzyl, MeGlu, Gly and Gln; $X_7$ is absent or is selected from the group consisting of Arg, Arg-Tosyl, MeArg, and Lys; $X_8$ is absent or is selected from the group consisting of Val, MeVal, Leu, and Ile; and $X_9$ is absent or is selected from the group consisting of Gly, Gly-amide, Ala, and Sar;

or a chemical derivative thereof;

wherein the fragment comprises at least four contiguous amino acid residues, and wherein said fragment has at least one activity selected from the group consisting of anti-inflammatory activity, free radical scavenging activity, metal chelating activity, metalloproteinase inhibitory activity, and T cell inhibitory activity.

According to some embodiments, at least one amino acid residues is absent from either the amino terminus, carboxy terminus, or both.

According to some additional embodiments, the fragment comprises at least five contiguous amino acid residues. According to yet other embodiments, the fragment comprises at least six contiguous amino acid residues. According to further embodiments, the fragment comprises at least seven contiguous amino acid residues. According to additional embodiments, the fragment comprises at least eight contiguous amino acid residues.

According to some non-limiting examples, the present invention provides a fragment as set forth in any one of SEQ ID NO: 43 to SEQ ID NO: 65 as follows (the designation of the peptides is indicated in parentheses):

```
H-Tyr-Ala-Glu-Arg-OH                     SEQ ID NO: 43
(Fragment 1);

H-His-Tyr-Ala-Glu-Arg-Val-Gly-OH         SEQ ID NO: 44
(Fragment 2);

H-Tyr-Ala-Glu-Arg-Val-Gly-OH             SEQ ID NO: 45
(Fragment 3);

H-Gly-His-Tyr-Ala-Glu-OH                 SEQ ID NO: 46
(Fragment 4);

H-Gly-His-Tyr-Ala-Glu-Arg-Val-Gly-OH     SEQ ID NO: 47
(Fragment 5);

H-Ala-Glu-Arg-Val-OH                     SEQ ID NO: 48
(Fragment 6);

H-Lys-Gly-His-Tyr-Ala-Glu-Arg-OH         SEQ ID NO: 49
(PFr7);

H-Lys-Gly-His-Tyr-Ala-Glu-Arg-Val-OH     SEQ ID NO: 50
(Fragment 8);

H-Glu-Arg-Val-OH                         SEQ ID NO: 51
(Fragment 9);

H-Lys-Gly-His-Tyr-Ala-OH                 SEQ ID NO: 52
(Fragment 10);

H-Ala-Glu-Arg-Val-Gly-OH                 SEQ ID NO: 53
(Fragment 11);

H-Tyr-Ala-Glu-Arg-Val-OH                 SEQ ID NO: 54
(Fragment 12);

H-Glu-Arg-Val-Gly-OH                     SEQ ID NO: 55
(Fragment 13);

H-Arg-Val-Gly-OH                         SEQ ID NO: 56
(Fragment 14);
```

```
H-Gly-His-OH;                        SEQ ID NO: 57

H-Val-Gly-OH;                        SEQ ID NO: 58

H-Tyr-Ala-OH;                        SEQ ID NO: 59

H-Lys-Gly-His-Tyr-OH;                SEQ ID NO: 60

H-Lys-Gly-His-Tyr-Ala-OH;            SEQ ID NO: 61

H-Gly-His-Tyr-Ala-Glu-Arg-Val-OH;    SEQ ID NO: 62

H-Lys-Gly-OH;                        SEQ ID NO: 63

H-Lys-Ala-Asn-Tyr-Ala-Glu-Arg-OH;    SEQ ID NO: 64

H-Lys-Gly-His-Tyr-Ala-Glu-Val-Gly-OH. SEQ ID NO: 65
```

The present invention further provides a peptide comprising at least ten amino acid residues of general formula II:

$$R_1-X_1-X_2-X_3-X_4-X_5-X_6-X_7-X_8-X_9-R_2 \qquad \text{SEQ ID NO: 66}$$

wherein $X_1$ is selected from the group consisting of Lys, carbobenzoxy-Lys, acetyl-Lys, Gln, and Arg; $X_2$ is selected from the group consisting of Gly, Ala, Sar, and Thr; $X_3$ is selected from the group consisting of His, MeHis, Benzyl-His, Asn, and Thr; $X_4$ is selected from the group consisting of Tyr, MeTyr, Tyr-O-Benzyl, and Ser; $X_5$ is selected from the group consisting of Ala, MeAla, Gly, Ser, and His; $X_6$ is selected from the group consisting of Glu, Glu-O-Benzyl, MeGlu, Gly and Gln; $X_7$ is selected from the group consisting of Arg, Arg-Tosyl, MeArg, and Lys; $X_8$ is selected from the group consisting of Val, MeVal, Ile, and Leu; $X_9$ is selected from the group consisting of Gly, Gly-amide, Ala, and Sar; $R_1$ is absent or is selected from the group consisting of Met, Arg, Leu-Arg, Leu-Leu-Arg, and Arg-Leu-Leu-Arg; and $R_2$ is absent or is selected from the group consisting of Ala, Ala-Gly, and Ala-Gly-Ala, wherein $R_1$ and $R_2$ cannot both be absent;

or a chemical derivative thereof;

wherein the peptide or chemical derivative has at least one activity selected from the group consisting of anti-inflammatory activity, free radical scavenging activity, metal chelating activity, metalloproteinase inhibitory activity, and T cell inhibitory activity.

According to some embodiments, the peptide comprises at least one amino acid extension at either the amino terminus, carboxy terminus, or both, and has an amino acid sequence as set forth in any one of SEQ ID NO: 67 to SEQ ID NO: 83 as follows (the designation of the peptides is indicated in parenthesis):

```
                                     SEQ ID NO: 67
H-Arg-Lys-Gly-His-Tyr-Ala-Glu-Arg-Val-Gly-OH
(AD1);

SEQ ID NO: 68
H-Lys-Gly-His-Tyr-Ala-Glu-Arg-Val-Gly-Ala-OH
(AD2);

SEQ ID NO: 69
H-Arg-Lys-Gly-His-Tyr-Ala-Glu-Arg-Val-Gly-Ala-OH
(AD3);

SEQ ID NO: 70
H-Leu-Arg-Lys-Gly-His-Tyr-Ala-Glu-Arg-Val-Gly-OH
(AD4);

SEQ ID NO: 71
H-Lys-Gly-His-Tyr-Ala-Glu-Arg-Val-Gly-Ala-Gly-OH
(AD5);

SEQ ID NO: 72
H-Leu-Arg-Lys-Gly-His-Tyr-Ala-Glu-Arg-Val-Gly-Ala-
OH (AD6);

SEQ ID NO: 73
H-Leu-Arg-Lys-Gly-His-Tyr-Ala-Glu-Arg-Val-Gly-Ala-
Gly-OH (AD7);

SEQ ID NO: 74
H-Leu-Leu-Arg-Lys-Gly-His-Tyr-Ala-Glu-Arg-Val-Gly-
OH (AD8);

SEQ ID NO: 75
H-Leu-Leu-Arg-Lys-Gly-His-Tyr-Ala-Glu-Arg-Val-Gly-
Ala-OH (AD9);

SEQ ID NO: 76
H-Leu-Leu-Arg-Lys-Gly-His-Tyr-Ala-Glu-Arg-Val-Gly-
Ala-Gly-OH (AD10);

SEQ ID NO: 77
H-Leu-Leu-Arg-Lys-Gly-His-Tyr-Ala-Glu-Arg-Val-Gly-
Ala-Gly-Ala-OH (AD11);

SEQ ID NO: 78
H-Lys-Gly-His-Tyr-Ala-Glu-Arg-Val-Gly-Ala-Gly-Ala-
OH (AD12);

SEQ ID NO: 79
H-Arg-Leu-Leu-Arg-Lys-Gly-His-Tyr-Ala-Glu-Arg-Val-
Gly-OH (AD13);

SEQ ID NO: 80
H-Arg-Leu-Leu-Arg-Lys-Gly-His-Tyr-Ala-Glu-Arg-Val-
Gly-Ala-OH (AD14);

SEQ ID NO: 81
H-Arg-Leu-Leu-Arg-Lys-Gly-His-Tyr-Ala-Glu-Arg-Val-
Gly-Ala-Gly-OH (AD15);

SEQ ID NO: 82
H-Met-Lys-Gly-His-Tyr-Ala-Glu-Arg-Val-Gly-OH
(MIIIM1);

SEQ ID NO: 83
H-Arg-Lys-Ala-Asn-Tyr-Ala-Glu-Arg-Val-Gly-OH.
```

The present invention further provides a peptide having the amino acid sequence:

```
                                     SEQ ID NO: 90
H-Lys-Gly-His-Tyr-Ala-Glu-Arg-Val-Gly-Cys-OH
(IIIM1C), or an analog or derivative thereof.
```

The person skilled in the art would have no problem in determining which of the peptide derivatives or analogs falls under the scope of the invention. A peptide derivative or analog can be prepared and tested in one of the assays disclosed herein below: assays for anti-inflammatory activity (see, for example, the assay of ear edema in Example 1, 13, and 14), assays for free radical scavenging (see, for example, Examples 7 to 9), and assays for metal chelating (see Example 11). A peptide derivative or analog, which is active in at least one of the assays, falls under the scope of the invention.

According to another aspect, the present invention provides an isolated polynucleotide sequence encoding the IIIM1 peptide, or a fragment, derivative, analog, or a conjugate thereof, the IIIM1 peptide, fragment, derivative, analog, or conjugate thereof having at least one activity selected from the group consisting of anti-inflammatory activity, free radical scavenging activity, metal chelating activity, metalloproteinase inhibiting activity, and T cell inhibitory activity.

The term "polynucleotide" means a polymer of deoxyribonucleic acid (DNA), ribonucleic acid (RNA) or a combination thereof, which can be derived from any source, can be single- or double-stranded, and can optionally contain synthetic, non-natural, or altered nucleotides, which are capable of being incorporated into DNA or RNA polymers.

An "isolated polynucleotide" refers to a polynucleotide segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to polynucleotides, which have been substantially purified from other components, which naturally accompany the polynucleotide in the cell, e.g., RNA or DNA or proteins. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA, which is part of a hybrid gene encoding additional polypeptide sequence, and RNA such as mRNA.

The term "encoding" refers to the inherent property of specific sequences of nucleotides in an isolated polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a peptide or protein if transcription and translation of mRNA corresponding to that gene produces the peptide or protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the peptide or protein or other product of that gene or cDNA.

One who is skilled in the art will appreciate that more than one polynucleotide may encode any given peptide or protein in view of the degeneracy of the genetic code and the allowance of exceptions to classical base pairing in the third position of the codon, as given by the so-called "Wobble rules." It is intended that the present invention encompass polynucleotides that encode peptide IIIM1 as set forth in SEQ ID NO: 1 as well as any derivative, analog, and fragment thereof.

According to an exemplary embodiment, the present invention provides a polynucleotide sequence as set forth in SEQ ID NO: 84 encoding a IIIM1 analog designated MIIIM1 as set forth in SEQ ID NO: 82.

A polynucleotide of the present invention can be expressed as a secreted peptide where the peptide IIIM1, or a derivative, analog or fragment thereof is isolated from the medium in which the host cell containing the polynucleotide is grown, or the polynucleotide can be expressed as an intracellular peptide by deleting the leader or other peptides, in which case the peptide IIIM1, derivative, analog or fragment thereof is isolated from the host cells. The peptide IIIM1, derivative, analog or fragment thereof so isolated is then purified by standard protein purification methods known in the art.

The IIIM1 peptide, analogs and fragments thereof can also be provided to the tissue of interest by transferring an expression vector comprising an isolated polynucleotide encoding the IIIM1 peptide, an analog or fragment thereof to cells associated with the tissue of interest. The cells produce the peptide such that it is suitably provided to the cells within the tissue to exert a biological activity such as, for example, to reduce or inhibit inflammatory processes within the tissue of interest.

The expression vector according to the principles of the present invention further comprises a promoter. In the context of the present invention, the promoter must be able to drive the expression of the peptide within the cells. Many viral promoters are appropriate for use in such an expression vector (e.g., retroviral ITRs, LTRs, immediate early viral promoters (IEp) (such as herpes virus IEp (e.g., ICP4-IEp and ICP0-IEp) and cytomegalovirus (CMV) IEp), and other viral promoters (e.g., late viral promoters, latency-active promoters (LAPs), Rous Sarcoma Virus (RSV) promoters, and Murine Leukemia Virus (MLV) promoters). Other suitable promoters are eukaryotic promoters, which contain enhancer sequences (e.g., the rabbit β-globin regulatory elements), constitutively active promoters (e.g., the β-actin promoter, etc.), signal and/or tissue specific promoters (e.g., inducible and/or repressible promoters, such as a promoter responsive to TNF or RU486, the metallothionine promoter, etc.), and tumor-specific promoters.

Within the expression vector, the polynucleotide encoding the IIIM1 peptide, an analog, derivative or fragment thereof and the promoter are operably linked such that the promoter is able to drive the expression of the polynucleotide. As long as this operable linkage is maintained, the expression vector can include more than one gene, such as multiple genes separated by internal ribosome entry sites (IRES). Furthermore, the expression vector can optionally include other elements, such as splice sites, polyadenylation sequences, transcriptional regulatory elements (e.g., enhancers, silencers, etc.), or other sequences.

The expression vectors are introduced into the cells in a manner such that they are capable of expressing the isolated polynucleotide encoding the IIIM1 peptide, a fragment, derivative or analog thereof contained therein. Any suitable vector can be so employed, many of which are known in the art. Examples of such vectors include naked DNA vectors (such as oligonucleotides or plasmids), viral vectors such as adeno-associated viral vectors (Berns et al., 1995, Ann. N.Y. Acad. Sci. 772:95-104, the contents of which are hereby incorporated by reference in their entirety), adenoviral vectors, herpes virus vectors (Fink et al., 1996, Ann. Rev. Neurosci. 19:265-287), packaged amplicons (Federoff et al., 1992, Proc. Natl. Acad. Sci. USA 89:1636-1640, the contents of which are hereby incorporated by reference in their entirety), papilloma virus vectors, picornavirus vectors, polyoma virus vectors, retroviral vectors, SV40 viral vectors, vaccinia virus vectors, and other vectors. Additionally, the vector can also include other genetic elements, such as, for example, genes encoding a selectable marker (e.g., β-gal or a marker conferring resistance to a toxin), a pharmacologically active protein, a transcription factor, or other biologically active substance.

Methods for manipulating a vector comprising an isolated polynucleotide are well known in the art (e.g., Sambrook et al., 1989, Molecular Cloning: A Laboratory Manual, 2d edition, Cold Spring Harbor Press, the contents of which are hereby incorporated by reference in their entirety) and include direct cloning, site specific recombination using recombinases, homologous recombination, and other suitable methods of constructing a recombinant vector. In this manner, an expression vector can be constructed such that it can be replicated in any desired cell, expressed in any desired cell, and can even become integrated into the genome of any desired cell.

The expression vector comprising the polynucleotide of interest is introduced into the cells by any means appropriate for the transfer of DNA into cells. Many such methods are well known in the art (e.g., Sambrook et al., supra; see also Watson et al., 1992, Recombinant DNA, Chapter 12, 2d edition, Scientific American Books, the contents of which are hereby incorporated by reference in their entirety). Thus, in the case of prokaryotic cells, vector introduction can be accomplished, for example, by electroporation, transformation, transduction, conjugation, or mobilization. For eukaryotic cells, vectors can be introduced through the use of, for example, electroporation, transfection, infection, DNA coated microprojectiles, or protoplast fusion. Examples of eukaryotic cells into which the expression vector can be introduced include, but are not limited to, ovum, stem cells, blactocytes, and the like.

Cells into which the polynucleotide has been transferred under the control of an inducible promoter if necessary, can be used as transient transformants. Such cells themselves may then be transferred into a subject for therapeutic benefit therein. Thus, the cells can be transferred to a site in the subject such that the peptide of the invention is expressed therein and secreted therefrom and thus reduces or inhibits, for example, inflammatory processes so that the clinical condition of the subject is improved. Alternatively, particularly in the case of cells to which the vector has been added in vitro, the cells can first be subjected to several rounds of clonal selection (facilitated usually by the use of a selectable marker sequence in the vector) to select for stable transformants. Such stable transformants are then transferred to a subject, preferably a human, for therapeutic benefit therein.

Within the cells, the polynucleotide encoding the IIIM1 peptide, an analog, derivative or fragment thereof is expressed, and optionally is secreted. Successful expression of the polynucleotide can be assessed using standard molecular biology techniques (e.g., Northern hybridization, Western blotting, immunoprecipitation, enzyme immunoassay, etc.).

The IIIM1 peptide, an analog, derivative or fragment thereof produced by recombinant techniques can be purified so that the peptides will be substantially pure when administered to a subject. The term "substantially pure" refers to a compound, e.g., a peptide, which has been separated from components, which naturally accompany it. Typically, a peptide is substantially pure when at least 50%, preferably at least 75%, more preferably at least 90%, and most preferably at least 99% of the total material (by volume, by wet or dry weight, or by mole percent or mole fraction) in a sample is the peptide of interest. Purity can be measured by any appropriate method, e.g., in the case of peptides by HPLC analysis.

It will be appreciated that the polynucleotides of the present invention can also be utilized to stably or transiently transform plant cells. In stable transformation, the polynucleotide of the present invention is integrated into the plant genome, and as such it represents a stable and inherited trait. In transient transformation, the polynucleotide is expressed by the cell transformed but not integrated into the genome, and as such represents a transient trait.

Methods of introducing foreign polynucleotides into plants are well known in the art. The principal methods of the stable integration of exogenous DNA into plant genomic DNA include the Agrobacterium-mediated gene transfer (see, for example, Klee, H. J. et al. (1987), Annu Rev Plant Physiol 38, 467-486, the contents of which are hereby incorporated by reference in their entirety) and Direct DNA uptake, which includes electroporation, microinjection, and microparticle bombardment. Transient transformation can be effected by any of the direct DNA transfer methods described above or by viral infection using modified plant viruses. A plant of which cells have been transformed with a polynucleotide of the invention so as to produce a transgenic plant is more resistant to oxidative stress than a non-transformed plant.

Pharmaceutical Compositions and Administration Routes

The present invention provides pharmaceutical compositions comprising as an active ingredient a therapeutically effective amount of a source of IIIM1, and a pharmaceutically acceptable carrier.

The source of IIIM1 refers herein to a IIIM1 peptide derivative, analog or fragment, to an isolated polynucleotide encoding the IIIM1 peptide, a derivative, analog or fragment thereof, to an expression vector comprising an isolated polynucleotide encoding the IIIM1 peptide, a derivative, analog or fragment thereof, or to cells transfected with the expression vector as described herein above.

The pharmaceutical compositions of the invention can be formulated in the form of a pharmaceutically acceptable salt of the peptides of the present invention or their analogs, derivatives or fragments thereof. Pharmaceutically acceptable salts include those salts formed with free amino groups such as salts derived from non-toxic inorganic or organic acids such as hydrochloric, phosphoric, acetic, oxalic, tartaric acids, and the like, and those salts formed with free carboxyl groups such as salts derived from non-toxic inorganic or organic bases such as sodium, potassium, ammonium, calcium, ferric hydroxides, isopropylamine, triethylamine, 2-ethylamino ethanol, histidine, procaine, and the like.

The term "pharmaceutically acceptable" means suitable for administration to a subject, e.g., a human. For example, the term "pharmaceutically acceptable" can mean approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic compound is administered. Such pharmaceutical carriers can be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; and agents for the adjustment of tonicity such as sodium chloride or dextrose are also envisioned.

The compositions can take the form of solutions, suspensions, emulsions, tablets, pills, capsules, powders, gels, creams, ointments, foams, pastes, sustained-release formulations and the like. The compositions can be formulated as a suppository, with traditional binders and carriers such as triglycerides, microcrystalline cellulose, gum tragacanth or gelatin. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in: Remington's Pharmaceutical Sciences" by E. W. Martin, the contents of which are hereby incorporated by reference herein. Such compositions will contain a therapeutically effective amount of a source of IIIM1, preferably in a substantially purified form, together with a suitable amount of carrier so as to provide the form for proper administration to the subject.

The amount of a source of IIIM1, which will be effective in the treatment of a particular disorder or condition will depend on the nature of the disorder or condition and on the particular IIIM1 source, and can be determined by standard clinical techniques known to a person skilled in the art. In addition, in vitro assays may optionally be employed to help identify optimal dosage ranges. The precise dose to be employed in the formulation will also depend on the route of administration, and the nature of the disease or disorder, and should be decided according to the judgment of the practitioner and each patient's circumstances. Effective doses can be extrapolated from dose-response curves derived from in-vitro or in-vivo animal model test bioassays or systems.

Depending on the location of the tissue of interest, a source of IIIM1 can be supplied in any manner suitable for the provision of the peptide to cells within the tissue of interest. Thus, for example, a composition containing a source of IIIM1 (i.e., a IIIM1 peptide derivative, analog or fragment thereof, or an isolated polynucleotide encoding the IIIM1 peptide, a derivative, analog or fragment thereof, or an expression vector comprising an isolated polynucleotide encoding the IIIM1 peptide, a derivative, analog or fragment thereof, or cells transfected with the expression vector as described herein above) can be introduced, for example, into the systemic circulation, which will distribute the source of IIIM1 to the tissue of interest. Alternatively, a composition containing a source of IIIM1 can be applied topically to the tissue of interest (e.g., injected, or pumped as a continuous infusion, or as a bolus within a tissue, applied to all or a portion of the surface of the skin, etc.).

The route of administration of the pharmaceutical composition will depend on the disease or condition to be treated. Suitable routes of administration include, but are not limited to, parenteral injections, e.g., intradermal, intravenous, intramuscular, intralesional, subcutaneous, intrathecal, and any other mode of injection as known in the art. Although the bioavailability of peptides administered by other routes can be lower than when administered via parenteral injection, by using appropriate formulations it is envisaged that it will be possible to administer the compositions of the invention via transdermal, oral, rectal, vaginal, topical, nasal, inhalation and ocular modes of treatment. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir. Pulmonary administration can also be employed, e.g., by use of an inhaler or nebulizer.

It may be desirable to administer the pharmaceutical composition of the invention locally to the area in need of treatment; this can be achieved by, for example, and not by way of limitation, local infusion, topical application, by injection, by means of a catheter, by means of a suppository, or by means of an implant, said implant being of a porous, non-porous, or gelatinous material. According to some preferred embodiments, administration can be by direct injection e.g., via a syringe, at the site of a damaged tissue.

For topical application, a IIIM1 peptide derivative, analog or a fragment thereof can be combined with a pharmaceutically acceptable carrier so that an effective dosage is delivered, based on the desired activity. According to an exemplary embodiment, the peptide of the invention is applied to the skin for treatment of diseases such as psoriasis. The carrier can be in the form of, for example, and not by way of limitation, an ointment, cream, gel, paste, foam, aerosol, suppository, pad or gelled stick.

For oral applications, the pharmaceutical composition may be in the form of tablets or capsules, which can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate; or a glidant such as colloidal silicon dioxide. When the dosage unit form is a capsule, it can contain, in addition to materials of the above type, a liquid carrier such as fatty oil. In addition, dosage unit forms can contain various other materials which modify the physical form of the dosage unit, for example, coatings of sugar, shellac, or other enteric agents. The tablets of the invention can further be film coated.

The IIIM1 peptide derivative, analog or a fragment thereof can be delivered in a controlled release system. Thus, an infusion pump can be used to administer the peptide such as the one that is used, for example, for delivering insulin or chemotherapy to specific organs or tumors. In one embodiment, the peptide of the invention is administered in combination with a biodegradable, biocompatible polymeric implant, which releases the peptide over a controlled period of time at a selected site. Examples of preferred polymeric materials include, but are not limited to, polyanhydrides, polyorthoesters, polyglycolic acid, polylactic acid, polyethylene vinyl acetate, copolymers and blends thereof (See, Medical applications of controlled release, Langer and Wise (eds.), 1974, CRC Pres., Boca Raton, Fla., the contents of which are hereby incorporated by reference in their entirety). In yet another embodiment, a controlled release system can be placed in proximity to a therapeutic target, thus requiring only a fraction of the systemic dose.

In yet another embodiment, the compositions of the present invention can be placed on a stent.

Uses of IIIM1 Peptides

The present invention provides a method for protecting a subject against noxious insults. The present invention further provides a method for preventing or treating diseases or disorders attributable to inflammatory processes in a subject. The present invention also provides a method for treating a disease or condition attributable to free radicals in a subject. The present invention further provides a method for treating T cell mediated disease in a subject.

According to the principles of the present invention, the methods comprise the step of administering to a subject in need thereof a pharmaceutical composition comprising as an active ingredient a therapeutically effective amount of a IIIM1 source and a pharmaceutically acceptable carrier. The IIIM1 source according to the present invention includes a IIIM1 peptide derivative, analog or a fragment according to principles of the present invention; an isolated polynucleotide sequence encoding the IIIM1 peptide, a derivative, analog or fragment thereof; an expression vector comprising the isolated polynucleotide sequence encoding the IIIM1 peptide, a derivative, analog or fragment thereof; and a host cell transfected with the expression vector comprising the isolated polynucleotide sequence of the invention.

A "therapeutically effective amount" of the peptide is that amount of peptide which is sufficient to provide a beneficial effect to the subject to which the peptide is administered. More specifically, a therapeutically effective amount means an amount of the peptide effective to prevent, alleviate or ameliorate tissue damage or symptoms of a disease of the subject being treated.

Noxious stimuli according to the present invention include, but are not limited to, heat stimuli, cold stimuli, chemical stimuli, electric stimuli, ultraviolet irradiation, ionizing or non-ionizing irradiation, irradiation of all kinds including electromagnetic and ultrasound, and oxidation.

According to an exemplary embodiment, the noxious stimulus is exemplified by sulphur mustard (SM). It will be appreciated that SM toxicity results from inflammatory responses and involvement of inflammatory mediators, namely the synthesis and secretion of inflammatory mediators are involved in the evolution and creation of tissue damage caused by SM. As the peptides of the invention have proven to be particularly efficacious against inflammatory processes whether induced by SM or carrageenan, or associated with experimental autoimmune encephalitis or arthritis, the peptides of the invention are therefore very useful as bona fide anti-inflammatory agents.

As anti-inflammatory agents, the peptides of the invention are expected to be efficacious in all diseases, disorders, or conditions that involve inflammation or inflammatory activity. Therefore, this invention relates to the protective effect of the IIIM1 source against all disorders or diseases that are related to or involve inflammation.

These diseases include autoimmune diseases including, but not limited to, cardiovascular disease, rheumatoid disease, glandular disease, gastrointestinal disease, cutaneous disease, hepatic disease, neurological disease, muscular disease, nephric disease, disease related to reproduction, connective tissue disease and systemic disease.

Inflammation is also associated with chronic neurological degenerative diseases and muscle degenerative diseases. The degenerative diseases include, but are not limited to, multiple sclerosis, Alzheimer's disease, Parkinson's disease, and myasthenia gravis, muscle dystrophy, and amyotrophic lateral sclerosis.

Inflammation is also associated with hypersensitivity. Hypersensitivity includes, but is not limited to, immediate hypersensitivity, antibody mediated hypersensitivity, immune complex mediated hypersensitivity, T lymphocyte mediated hypersensitivity and delayed type hypersensitivity.

Inflammation is also associated with an infectious disease. Infections diseases that can be treated with the pharmaceutical compositions of the invention include, but are not limited to, viral diseases, bacterial diseases, protozoan diseases, parasitic diseases, fungal diseases, and mycoplasma diseases. Thus, the compositions comprising the peptides of the invention can be used as cosmetics to eliminate skin infections.

Inflammation can also be associated with transplantation of a graft, such as, for example, in conditions of graft rejection.

Inflammation can also be associated with an allergic disease and with musculo-skeletal inflammation. The musculo-skeletal inflammation is selected from the group consisting of arthritis, muscle inflammation, myositis, a tendon inflammation, tendinitis, a ligament inflammation, a cartilage inflammation, a joint inflammation, a synovial inflammation, carpal tunnel syndrome and a bone inflammation.

The peptides of the invention are useful for protecting against or treating T cell mediated disease. T cell mediated diseases include, but are not limited to, psoriasis; allergy; T cell lymphomas and other malignancies; graft versus host disease; prevention of transplant rejection; bronchitis; asthma; autoimmunity; sarcoidosis; bone marrow depression; bone marrow stimulation; sepsis; Parkinson's disease; skin disorders and irritation; arthritis; multiple sclerosis; neurodegenerative disorders (amyotrophic lateral sclerosis, chorea, Alzheimer disease); atherosclerosis; fibrosis; pain; chronic or acute inflammation.

The protective effect of the peptides of the invention can be achieved by prophylactic treatment. For example treatment with a peptide of the invention prior (5 minutes to 3 days) to the noxious stimulus protects the individual against a biological damage caused by the noxious stimulus. The protective effect can also be achieved by post-exposure treatment with the peptide. Similarly, the protective effect of the peptides is achieved against inflammatory processes as exemplified herein below.

The term "protecting" relate to reduction of degree of lesion or biological damage as measured by gross pathology or histopathological evaluation, subjective burning sensation or other accepted parameters for tissue damage, lesion, discomfort and pain.

The pharmaceutical compositions of the invention can be used for accelerated healing of or prevention of development of wounds including decubitus, ulcers (also induced by drugs), internal and external wounds, abscesses and various bleedings.

The pharmaceutical compositions of the invention are useful for treatment and protection of the central and peripheral nervous systems against noxious stimuli caused by, but not limited to, chemicals, drugs, all kinds of irradiation and mechanical stress. As neuronal-affecting agents, the peptides may also serve in treatment of a variety of mental diseases and mental-related syndromes.

The pharmaceutical compositions of the invention are useful for treatment or protection against tissue damage including, but not limited to, neuronal, neurological, skin, hepatic, nephrologic, urologic, cardiac, pulmonary, gastrointestinal, lower and upper airways, visual, audiologic, spleen, bone, and muscle damage. Treatment or protection against tissue damage can be accomplished in the fetus, newborn, child, adolescent as well as in adults and old persons, whether the condition or disorder to be treated is spontaneous, of traumatic etiology or as a congenital defect.

The pharmaceutical compositions of the invention can be used for treatment or protection against metal poisoning, particularly heavy metal poisoning. The peptides can be used as antidote against toxic metals.

It will be understood that the pharmaceutical compositions of the present invention can comprise a single IIIM1 peptide derivative, analog or fragment thereof or any other source of IIIM1, or all possible combinations of two or more of these peptide derivatives, analogs, or fragments or other sources of IIIM1. Additionally, the pharmaceutical compositions can comprise one or more isolated polynucleotides, one or more expression vectors, or one or more host cells or any combination thereof, according to the principles of the present invention.

According to the invention, the peptides can inhibit or significantly reduce metalloproteinase activity. As such, the peptides will reduce at least 10%, preferably at least 40%, and more preferably at least 80%, of the hydrolytic activity of at least one matrix metalloproteinase that is naturally occurring in a mammal.

Among the matrix metalloproteinases (MMP) Stromelysin-1 and gelatinase A are the more abundant members of the family. Other members include fibroblast collagenase (MMP-1), neutrophil collagenase (MMP-8), gelatinase B (92 kDa gelatinase) (MMP-9), stromelysin-2 (MMP-10), stromelysin-3 (MMP-11), matrilysin (MMP-7), collagenase 3 (MMP-13), TNF-alpha converting enzyme (TACE). The present invention encompasses IIIM1 peptide derivatives, analogs or fragments thereof capable of inhibiting any known membrane-associated matrix metalloproteinases (see, for example, Sato H., Takino T., Okada Y., Cao J., Shinagawa A., Yamamoto E., and Seiki M., Nature, 1994, 370:61-65, the contents of which are hereby incorporated by reference in their entirety).

The peptides, derivatives and analogs of the present invention can also be used in combination with one or more known peptide-based or non-peptide-based MMP inhibitors, such as peptide or non-peptide hydroxamates or thiol-containing peptides.

The term "altered MMP activity" as used herein refers to MMP activity, which is higher than the normal activity of the enzyme at that cell or tissue.

Inflammatory diseases can affect the central nervous system (brain and spinal cord). Some of the best characterized disorders are multiple sclerosis (MS) and various forms of meningitis and encephalitis. A common feature of these diseases is a disruption of the blood-brain barrier (BBB) followed by inflammatory perivascular infiltration and eventual demyelination and astrogliosis. MMPs play a key role in allowing inflammatory cell access to the CNS. Both MMP-2 and MMP-9 are found in the CSF of patients with MS, and MMP-9 immunoreactivity can be detected in active MS lesions.

The most convincing evidence for the involvement of MMPs in contributing to the breakdown of the BBB and the ensuing inflammation is the ability of hydroxamate inhibitors of MMPs to reduce the clinical symptomology of experimental autoimmune encephalomyelitis (EAE). In addition to the role of MMPs in contributing to the disruption of the BBB, there is good evidence that MMPs can also directly degrade myelin basic protein leading to the demyelination characteristic of MS. This indicates that MMPs play a critical role in two key processes in the pathophysiology of MS; namely disruption of the BBB and demyelination. This provides a strong rationale for the development of systemically active inhibitors of metalloproteinases for the treatment of multiple sclerosis.

MMPs also play a role in other neurological disorders, which are not generally considered to be inflammatory in nature. For example, MMPs are probably responsible for the opening of the BBB in focal ischemia and hemorrhagic brain injury leading to secondary injury from vasogenic edema. Thus, the peptides of the present invention are useful in the treatment of brain injury.

Determination of a therapeutically effective amount is well within the capability of those skilled in the art, especially in light of the detailed disclosure provided herein.

Toxicity and therapeutic efficacy of the peptides described herein can be determined by standard pharmaceutical procedures in cell cultures or experimental animals, e.g., by determining the $IC_{50}$ (the concentration which provides 50% inhibition) and the $LD_{50}$ (lethal dose causing death in 50% of the tested animals) for a subject compound. The data obtained from these cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See, for example, Fingl et al., 1975, in The Pharmacological Basis of Therapeutics, Ch. 1 p. 1, the contents of which are hereby incorporated by reference in their entirety).

Depending on the severity and responsiveness of the condition to be treated, dosing can also be a single administration of a slow release composition, with course of treatment lasting from several days to several weeks or until cure is effected or diminution of the disease state is achieved.

The amount of a composition to be administered will, of course, depend on the subject being treated, the severity of the affliction, the manner of administration, the judgment of the prescribing physician, and all other relevant factors. Determination of the exact dose to be administered is conducted by methods known to a person of skill in the art.

It is further understood that the peptides of the invention can be formulated or administered together with additional active ingredients as required to treat the condition of the patient.

EXAMPLES

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

Example 1

Protective Effect of IIIM1 Peptide Against SM-Induced Ear Edema

Male ICR mice (~25 g) were anesthetized by ip injection of sodium pentobarbital (60 mg/kg; 0.1 ml/25 g BW of 1.5% solution) and placed on their abdominal side. Anesthesia was maintained by administration of sodium pentobarbital (0.03 ml/25 g BW) when needed. Each ear was exposed to 0.080 mg sulphur mustard (SM; 5 µl of 1:80 dilution in dichloromethane). Thirty minutes before, immediately before, and 30 and 60 minutes after SM exposure, the IIIM1 peptide having the amino acid sequence: Lys-Gly-His-Tyr-Ala-Glu-Arg-Val-Gly (dissolved in 0.9% NaCl) was injected subcutaneously (sc) into the area of the ear base at a single dose of 50 µg per each site of injection, namely two sites per animal were injected—a single injection per ear (volume of injection per site was 0.02 ml). Control (C) animals received 0.9% NaCl injections. Mouse ear thickness was measured 120 hours after exposure using micrometer (Model PK-0505, Mitutoyo Corporation, Japan). Edema was assessed by the difference between ear thickness measured after and prior to exposure. FIG. 1 shows the protective effect of IIIM1 peptide on SM-induced ear edema, whether administered prior to SM treatment or after that treatment.

Example 2

Degradation Products of IIIM1 Peptide

The IIIM1 peptide (30 µg) was incubated with mouse serum (24 µl) to give a total volume of 25 µl. The reaction was stopped by addition of concentrated perchloric acid (3 µl). After centrifugation, the supernatant was analyzed by HPLC. Peaks of the eluate were collected and analyzed by mass spectrometry of the degradation products. The resulting cleavage sites were as follows:

```
              ↓   ↓   ↓
H-Lys-Gly-His-Tyr-Ala-Glu-Arg-Val-Gly-OH
```

The corresponding degradation products were as follows:

| | |
|---|---|
| H-Gly-His-Tyr-Ala-Glu-Arg-Val-Gly-OH | (GHYAERVG) |
| H-His-Tyr-Ala-Glu-Arg-Val-Gly-OH | (HYAERVG) |
| H-Tyr-Ala-Glu-Arg-Val-Gly-OH | (YAERVG) |

The same degradation products were produced by incubation of the peptide with human serum. The T1/2 of the IIIM1 peptide in mouse and human serum (in vitro) was 7 and 14 minutes, respectively.

Example 3

Protective Effect of a Methylated Analog of IIIM1 Peptide Against SM-Induced Ear Edema Male ICR mice (~25 g) were anesthetized by ip administration of sodium pentobarbital (60 mg/kg; 0.1 ml/25 g BW of 1.5% solution) and placed on their abdominal side. Anesthesia was maintained by administration of sodium pentobarbital (0.03 ml/25 g) when needed. Each ear was exposed to 0.080 mg SM (5 μl of 1:80 dilution in dichloromethane). Thirty minutes after SM exposure, P4 peptide having the amino acid sequence: Lys-Gly-MeHis-MeTyr-Ala-Glu-Arg-Val-Gly (SEQ ID NO: 8; dissolved in 0.9% NaCl) was injected subcutaneously (sc) into the area of the ear base at the indicated dose per each site of injection, namely two sites per animal were injected—a single injection per ear (volume of injection per site was 0.02 ml). Control (C) animals received 0.9% NaCl injections. Mouse ear thickness was measured 120 hours after exposure using micrometer (Model PK-0505, Mitutoyo Corporation, Japan). Edema was assessed by the difference between ear thickness measured after and prior to exposure.

Figure 2:
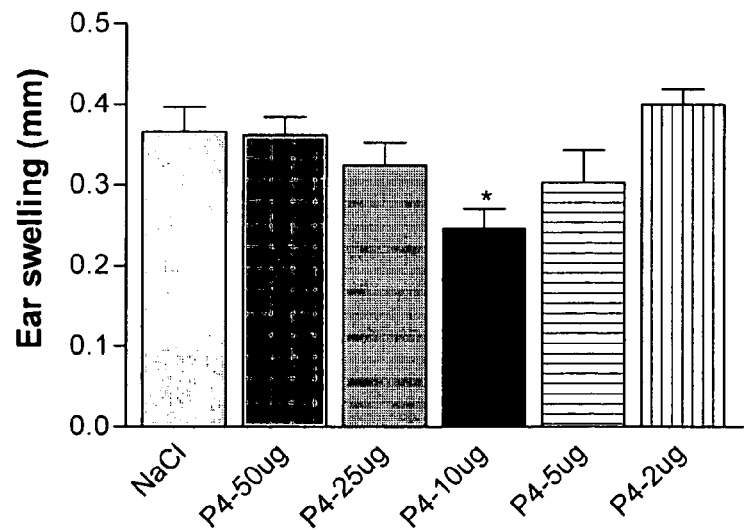
FIG. 2 shows the protective effect of a methylated derivative of IIIM1 designated P4 against SM-induced chemical burns by post exposure treatments.

FIG. 2 shows the protective effect of P4 peptide against SM-induced ear edema as a function of peptide concentration.

Example 4

Protective Effect of a Deletion Peptide Against SM-Induced Ear Edema

Male ICR mice (~25 g) were anesthetized by ip administration of sodium pentobarbital (60 mg/kg; 0.1 ml/25 g BW of 1.5% solution) and placed on their abdominal side. Anesthesia was maintained by sodium pentobarbital administration (0.03 ml/25 g) when needed. Each ear was exposed to 0.080 mg SM (5 μl of 1:80 dilution in dichloromethane). At the indicated time intervals after SM exposure, Pfr7 peptide having the amino acid sequence: Lys-Gly-His-Tyr-Ala-Glu-Arg (SEQ ID NO: 49; dissolved in 0.9% NaCl) was injected subcutaneously (sc) into the area of the ear base at a dose of 50 μg per each site of injection, namely two sites per animal were injected—a single injection per ear (volume of injection per site was 0.02 ml). Control (C) animals received 0.9% NaCl injections. Mouse ear thickness was measured 96 hours after exposure using micrometer (Model PK-0505, Mitutoyo Corporation, Japan). Edema was assessed by the difference between ear thickness measured after and prior to exposure.

Figure 3:
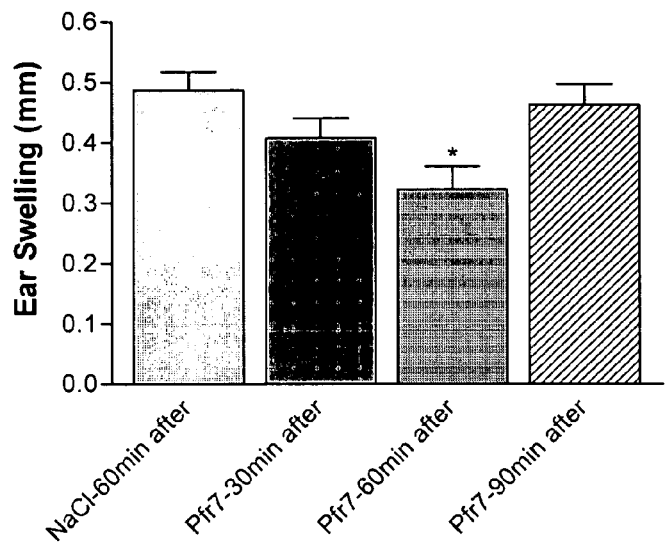
FIG. 3 shows the protective effect of a fragment of peptide IIIM1 designated Pfr7 against SM-induced chemical burns by post exposure treatments.

FIG. 3 shows the protective effect of Pfr7 peptide against SM-induced ear edema as a function of time.

Example 5

Protective Effect of Extension Peptides of IIIM1 Against SM-Induced Ear Edema—Subcutaneous Administration Male ICR mice (~25 g) were anesthetized by ip administration of sodium pentobarbital (60 mg/kg; 0.1 ml/25 g BW of 1.5% solution) and placed on their abdominal side. Anesthesia was maintained by sodium pentobarbital administration (0.03 ml/25 g) when needed. Each ear was exposed to 0.080 mg SM (5 μl of 1:80 dilution in dichloromethane). Thirty minutes after SM exposure, each of the peptides designated AD1-AD15 having the amino acid sequence of the IIIM1 peptide and 1 to 6 additional amino acid residues at either the amino and/or carboxyl terminal of the peptide as set forth in Table 1 (dissolved in 0.9% NaCl; administered to a different group of animals) was injected. The injection was subcutaneous (sc) into the area of the ear base at a dose of 50 μg per each site of injection, namely two sites per animal were injected—a single injection per ear (volume of injection per site was 0.02 ml). Control (C) animals received 0.9% NaCl injections. Mouse ear thickness was measured 96 hours after exposure using micrometer (Model PK-0505, Mitutoyo Corporation, Japan). Edema was assessed by the difference between ear thickness measured after and prior to exposure.

Figure 4:
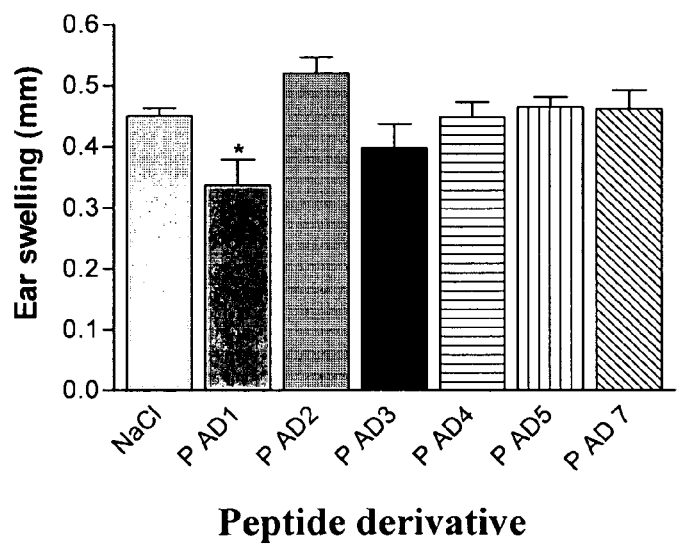
FIG. 4 shows the protective effect of peptide IIIM1 derivatives having extensions at either one or both of the peptide terminals against SM-induced chemical burns by post exposure treatments.

FIG. 4 and Table 1 show the protective effect of AD1 to AD15 peptides on SM-induced ear edema.

TABLE 1

Protective activity of IIIM1 extension peptides against SM-induced ear swelling - subcutaneous administration 30 min after SM exposure.

| peptide | administration | protection (%) |
|---|---|---|
| AD1 (SEQ ID NO: 67) | sc | 25 |
| AD3 (SEQ ID NO: 69) | sc | 11 |
| AD2 (SEQ ID NO: 68) | sc | 0 |
| AD4 (SEQ ID NO: 70) | sc | 0 |
| AD5 (SEQ ID NO: 71) | sc | 0 |
| AD6 (SEQ ID NO: 72) | sc | 0 |
| AD7 (SEQ ID NO: 73) | sc | 0 |
| AD9 (SEQ ID NO: 75) | sc | 0 |
| AD10 (SEQ ID NO: 76) | sc | 6 |
| AD13 (SEQ ID NO: 79) | sc | 0 |
| AD14 (SEQ ID NO: 80) | sc | 0 |
| AD15 (SEQ ID NO: 81) | sc | 0 |

The protection is expressed as percent of reduction in ear swelling of the peptide-treated group as compared to the control group.

Example 6

Protective Activity of Various Peptides Against SM-Induced Ear Swelling—Intravenous (i.v.) Administration Male ICR mice (~25 g) were anesthetized by ip administration of sodium pentobarbital (60 mg/kg; 0.1 ml/25 g BW of 1.5% solution) and placed on their abdominal side. Anesthesia was maintained by administration of sodium pentobarbital (0.03 ml/25 g BW) when needed. Peptides (dissolved in 0.9% NaCl) were injected intravenously (iv) (each peptide injected into different group of animals) at a single dose of 1 mg/kg body weight (volume of injection was 0.2 ml). Control animals received 0.9% NaCl injections. Within 5 min after injection, the outer side of each ear was exposed to 0.317 mg SM (5 μl of 1:20 dilution in dichloromethane). Mouse ear thickness was measured 48 hours after exposure using micrometer (Model PK-0505, Mitutoyo Corporation, Japan). Edema was assessed by the difference between ear thickness measured after and prior to exposure.

TABLE 2

Protective activity of peptides against SM-induced ear swelling - intravenous (iv) administration.

| peptide | | administration | protection (%) |
|---|---|---|---|
| H-Gly-His-OH | (SEQ ID NO: 57) | iv | 27 |
| H-Val-Gly-OH | (SEQ ID NO: 58) | iv | 15 |
| H-Tyr-Ala-OH | (SEQ ID NO: 59) | iv | 18 |
| Fragment 8 | (SEQ ID NO: 50) | iv | 5 |
| Fragment 3 | (SEQ ID NO: 45) | iv | 31 |
| Fragment 2 | (SEQ ID NO: 44) | iv | 8 |
| IIIM1-Sar2MeHisMeTyr | (SEQ ID NO: 20) | iv | 0 |
| IIIM1-Sar2MeHis | (SEQ ID NO: 21) | iv | 32 |

The protection is expressed as percent of reduction in ear swelling of the peptide-treated group as compared to the control group.

As shown in Table 2, fragments derived from IIIM1 peptide as well as the analog designated IIIM1-Sar2MeHis were found to effectively protect SM-induced ear edema when injected intravenously.

Example 7

Scavenging of Hydroxyl Radicals by MeAla IIIM1 Peptide

Horseradish peroxidase (HRP; 5 μl of 100 μg/ml) was incubated with 2 μl of 10 μM luminol and 2 μl of MeAla IIIM1 in Hank's balanced salt solution (HBSS; 200 μl) (final concentrations of the peptide in the reaction mixture are indicated in the figure). The reaction started by the addition of 5 μl of 7.5 mg/ml Glucose Oxidase. The reaction was performed in 96 well plate. Luminescence was measured by Tecan SpecrtoFluoroPlus (Tecan GmbH, Austria).

Figure 5:
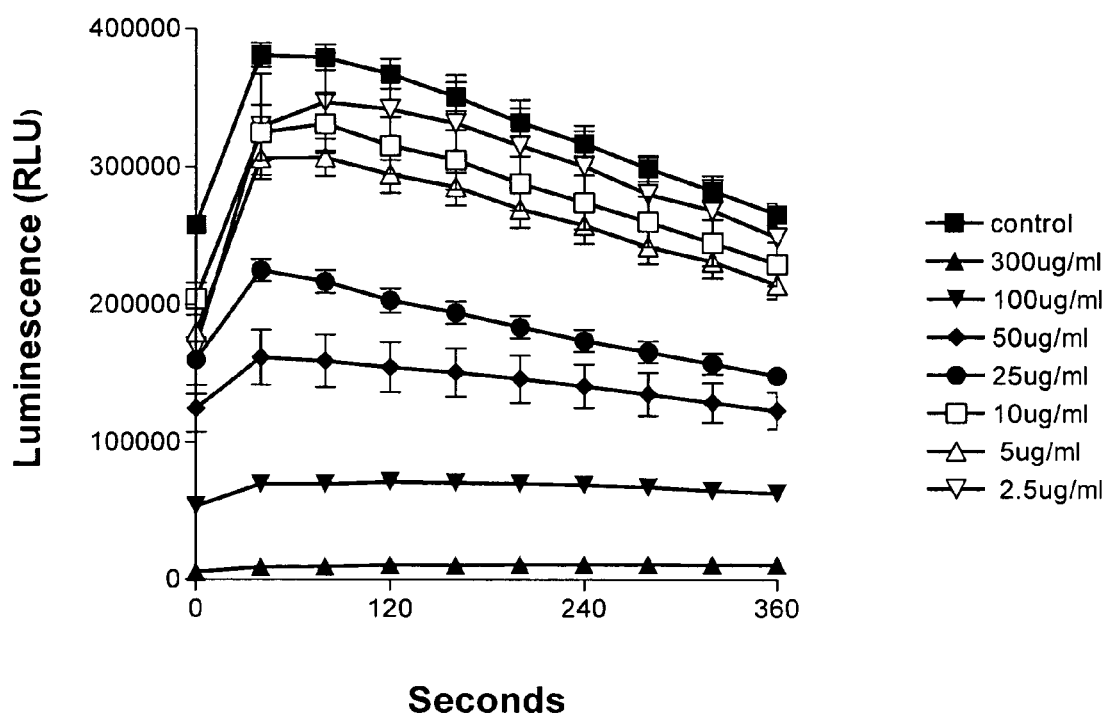
FIG. 5 shows the hydroxyl radical scavenging effect of a methylated derivative of peptide IIIM1 designated MeAla IIIM1, as a function of time and peptide concentration.

FIG. 5 shows the activity of MeAla IIIM1 peptide having the amino acid sequence Lys-Gly-His-Tyr-MeAla-Glu-Arg-Val-Gly (SEQ ID NO: 9) in scavenging free hydroxyl radicals as a function of time and as a function of the concentration of the peptide.

Figure 6:
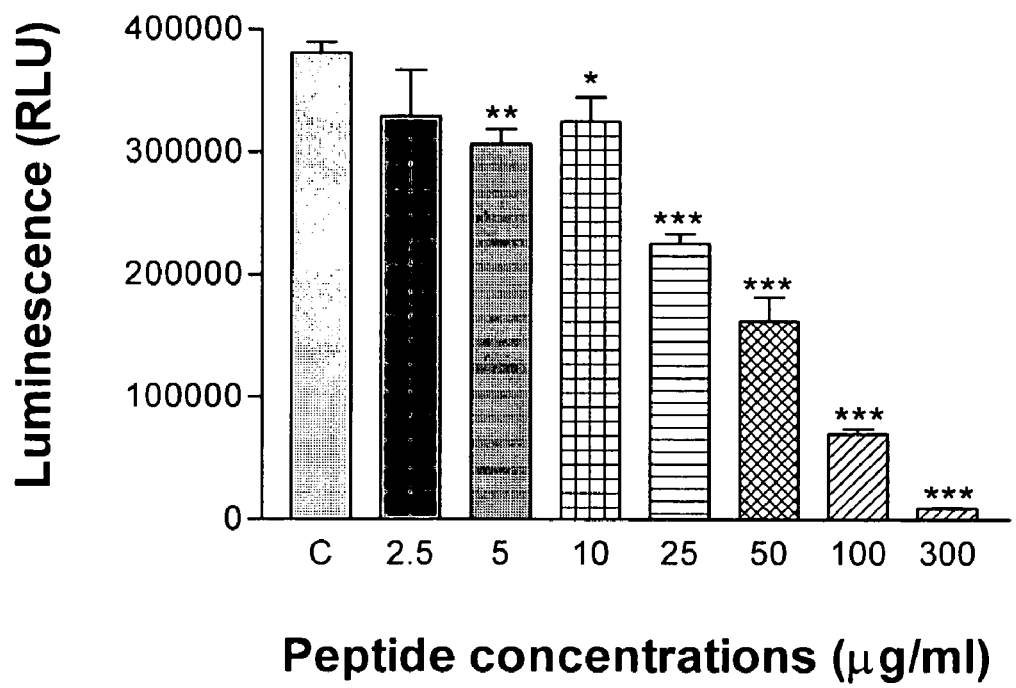
FIG. 6 shows the hydroxyl radical scavenging effect of a methylated derivative of peptide IIIM1 designated MeAla IIIM1, as a function of peptide concentration.

FIG. 6 shows the activity of MeAla IIIM1 peptide in scavenging free hydroxyl radicals as a function of the concentration of the peptide. Values presented were obtained after 40 sec of incubation.

Example 8

Scavenging of Hydroxyl Radicals by IIIM1 Peptide $CoCl_2$ (2 μl of 1 mM), $Na_2SeO_3$ (2 μl of 100 mM), luminol (2 μl of 10 μM) and IIIM1 (2 μl) were incubated in Hank's balanced salt solution (HBSS) (200 μl) (final concentrations of the peptide in the reaction mixture are indicated in the figure). The reaction started by the addition of 5 μl of 7.5 mg/ml Glucose Oxidase. The reaction was performed in 96 well plate. Luminescence was measured by Tecan SpecrtoFluoroPlus (Tecan GmbH, Austria).

Figure 7:
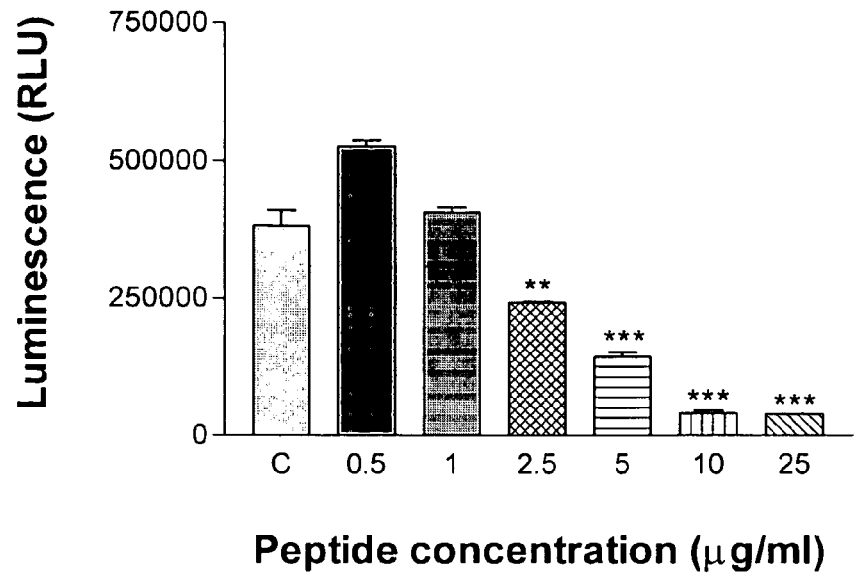
FIG. 7 shows the hydroxyl radical scavenging effect of IIIM1, as a function of peptide concentration.

FIG. 7 shows the activity of the IIIM1 peptide in scavenging free hydroxyl radicals as a function of the concentration of the peptide.

Example 9

Scavenging of Hydroxyl Radicals by MeAla IIIU3 Peptide $CoCl_2$ (2 μl of 1 mM), $Na_2SeO_3$ (2 μl of 100 mM), luminol (2 μl of 10 μM) and MeAla IIIU3 having the amino acid sequence H-Lys-Ala-Asn-Tyr-MeAla-Glu-Arg-Val-Gly-OH (SEQ ID NO: 32) (2 μl) were incubated in Hank's balanced salt solution (HBSS) (200 μl) (final concentrations in the reaction mixture are indicated in the figure). The reaction started by the addition of 5 μl of 7.5 mg/ml Glucose Oxidase. The reaction was performed in 96 well plate. Luminescence was measured by Tecan SpecrtoFluoroPlus (Tecan GmbH, Austria).

Figure 8:
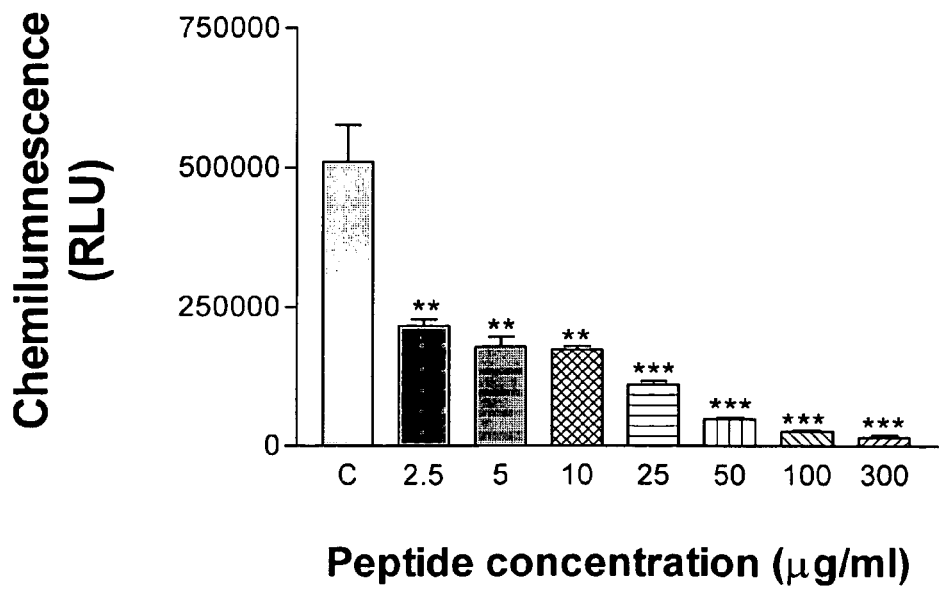
FIG. 8 shows the hydroxyl radical scavenging effect of a methylated derivative of peptide IIIM1 designated MeAla IIIU3, as a function of peptide concentration.

FIG. 8 shows the activity of MeAla IIIU3 peptide in scavenging free hydroxyl radicals as a function of the concentration of the peptide.

Example 10

Effect of IIIM1 Peptide on Oxidative Burst in Mouse Neutrophils

Mice were injected ip with 1.5 ml thioglycolate (29.8 g/l). Peritoneal neutrophils were obtained and incubated ($2.5 \times 10^6$ cells/ml) in HBSS with 2 μl of 1 mM $CoCl_2$, 2 μl 1100 mM $Na_2SeO_3$, 2 μl of 10 mM luminol. The reaction started by the addition of 5 μl of 100 μM phorbol myristate acetate (PMA) (final concentration of 2.5 μM) and 1 minute later IIIM1 was added. Luminescence measurement was started after PMA addition.

Figure 9:
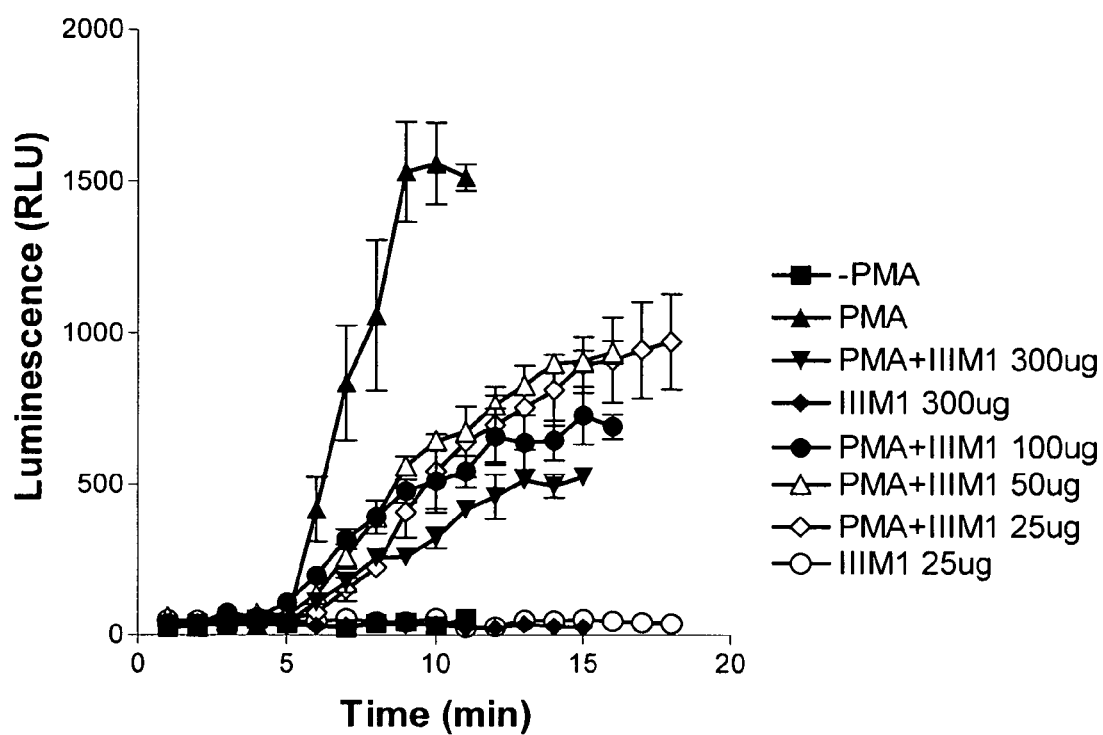
FIG. 9 shows the effect of peptide IIIM1 on oxidative burst in mouse peritoneal neutrophils, as a function of time.

FIG. 9 shows the protective effect of IIIM1 peptide on the oxidative burst in mouse peritoneal neutrophils as a function of time and IIIM1 concentration.

Figure 10:
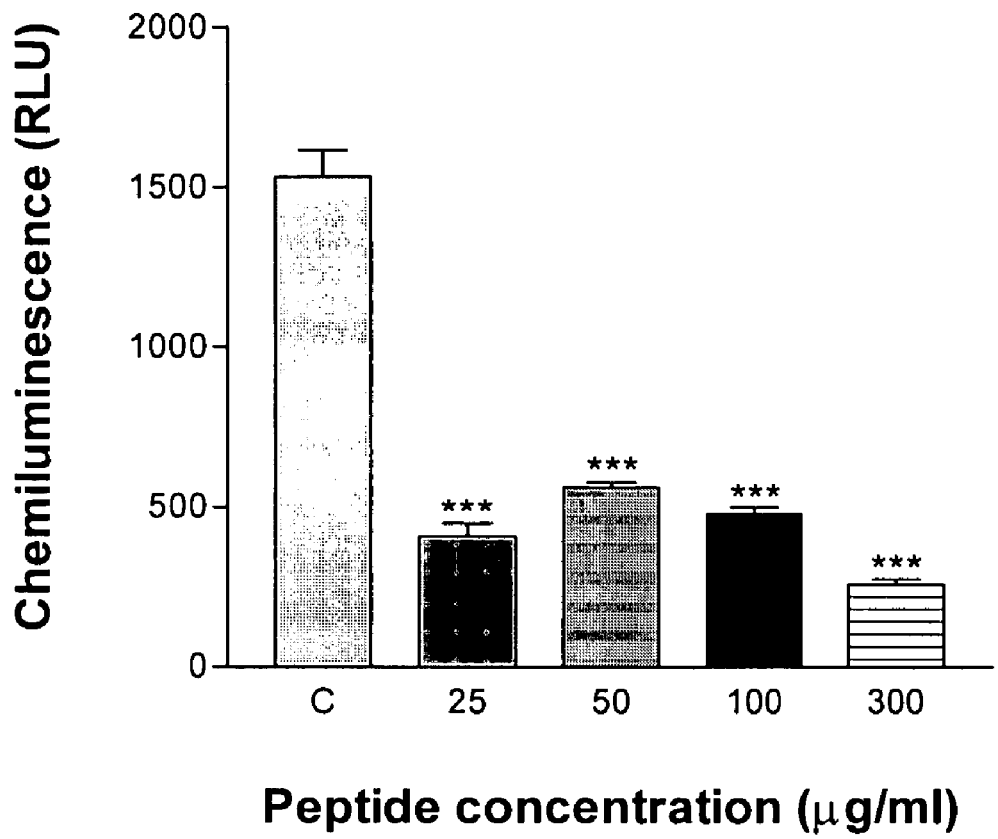
FIG. 10 shows the effect of peptide IIIM1 on oxidative burst in mouse peritoneal neutrophils, as a function of peptide concentration.

FIG. 10 shows the protective effect of IIIM1 peptide on the oxidative burst in mouse peritoneal neutrophils as a function of IIIM1 concentration 10 minutes after PMA addition.

Example 11

Metal Chelating Properties of IIIM1 Peptide

Incubation mixture contained 1 mg/ml of IIIM1 peptide, 10 μM or 30 μM $CoCl_2$ in a final volume of 100 μl. After 3 minutes at room temperature, the reaction was separated by HPLC equipped with Luna C18 5 µm column (4 mm×25 cm) using gradient system of 0.1% trifluoroacetic acid (TFA) (solvent A) and 100% acetonitrile (AcN) (solvent B) as follows: 0 min-B0 %; 35 min-B20%; 40 min-B40%. Two relevant peaks were eluted from the column: a first peak was eluted at 18.2 min and a second peak was eluted at 19.1 min (Table 3). Mass spectrometry (MS) of the first and second eluted peaks showed mass corresponding to IIIM1 and cobalt-IIIM1 complex, respectively. The cobalt-IIIM1 peak did not appear when cobalt was omitted from the reaction mixture. None of the peaks appeared when IIIM1 was omitted from the reaction mixture while cobalt chloride was present. No binding of cobalt was observed, i.e., the 19.1 min peak did not appear, when the Glu was substituted by Gln moiety (KGHYAQRVG), indicating the role of the negative charge of the Glu residue in metal binding. The results are presented in Table 3.

TABLE 3

Elution profile of a mixture of cobalt chloride and IIIM1.

| | Retention time | Peptide content | Cobalt content |
|---|---|---|---|
| Peak I | 18.2 | IIIM1 | <0.5 µg/l |
| Peak II | 19.1 | IIIM1 | 7.5 µg/l |

Example 12

Effect of III and IIIH Peptides on SM-Induced Skin Lesions in Guinea Pigs

Figure 11A:
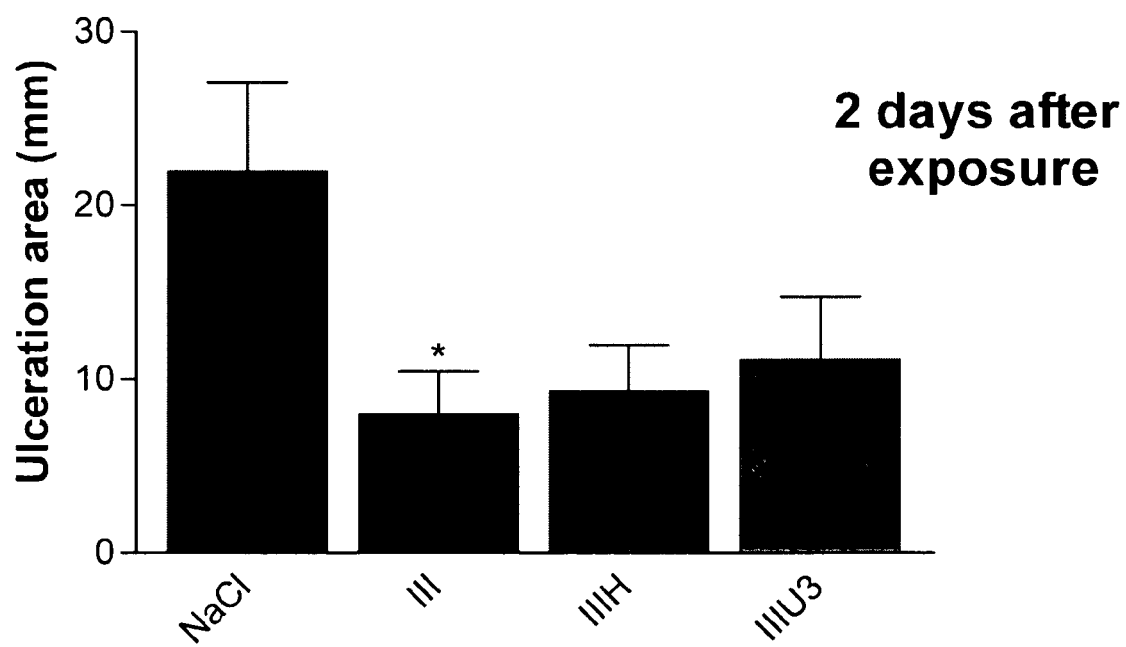
FIGS. 11A-C show the protective effect of peptides III, IIIH, and IIIU3 on sulfur mustard (SM)-induced skin lesions in guinea pigs.
Figure 11B:
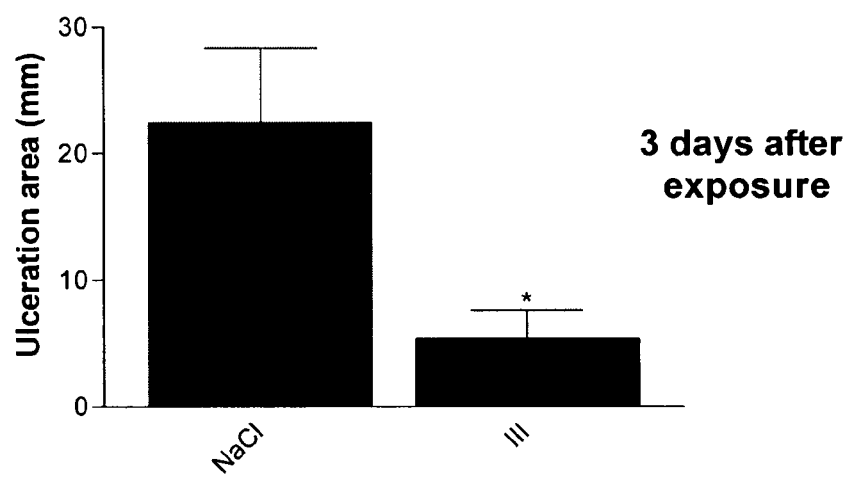
Figure 11C:
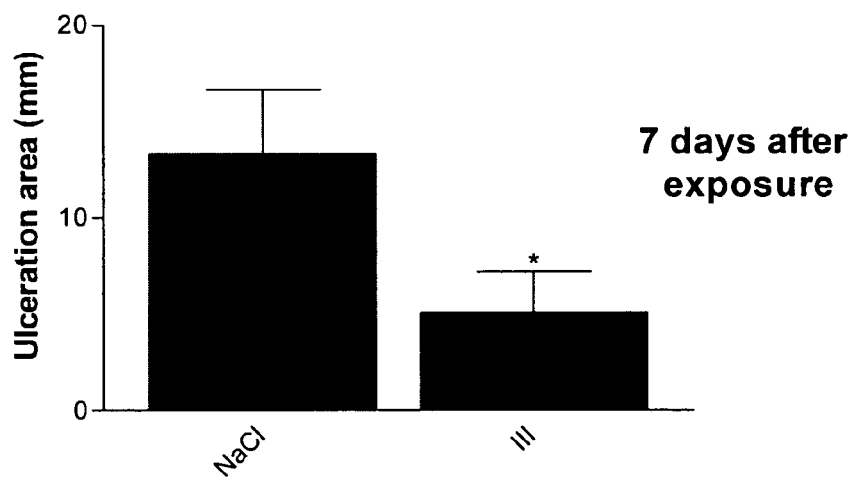

Male guinea pigs were intracadially injected with either peptide III (SEQ ID NO:2), IIIH (SEQ ID NO:31) or IIIU3 (SEQ ID NO:29; 1 mg of each peptide/kg) or the vehicle (0.9% NaCl) either 7 days (single treatment; FIG. 11A) or 7, 5, 3 days and 20 min (total of 4 injections; FIG. 11B-C) prior to exposure to sulfur mustard (SM). The backs of the animals were shaved 24 hours prior to the exposure, each back was divided into six sites, each site was exposed to 1 µl (1.27 mg) of SM. The size of ulceration area of each exposure site was measured and expressed as squared mm. Results are the mean±SE of 18 sites in the control group and 18 sites in the peptide-treated groups.

As shown in FIG. 11A-C, pretreatments of guinea pigs with peptide III resulted in statistically significant protection (*p<0.05, Mann-Whitney test) against SM-induced skin lesions. Peptides IIIH and IIIU3 showed protective effect against SM-induced skin lesions, though it was less prominent.

Example 13

Effect of Peptide IIIM1 on Arthritic Mice

Collagen of bovine tracheal cartilage (1.8 mg) was incubated overnight in 0.01 M acetic acid (0.9 ml) at 4° C. The resulting solution was emulsified with equal volume (0.9 ml) of Complete Freund's Adjuvant. Fifty microliters of the emulsion were injected intradermally in the tail base of a mouse. The immunization was repeated 25 days later. The joints started to swell 5 days after the second immunization. On the same day, IIIM1 peptide was injected intracardially (1 mg/kg in 0.25 ml saline). IIIM1 peptide injection was repeated 7, 11 and 14 days after the first peptide injection. Degree of joint swelling was calculated as the difference in joint thickness between the indicated time intervals and prior immunization. Results are the mean±SE of 18 joints of each experimental group using the Mann Whitney test for evaluation of the differences between the peptide-treated and control groups.

Figure 12:
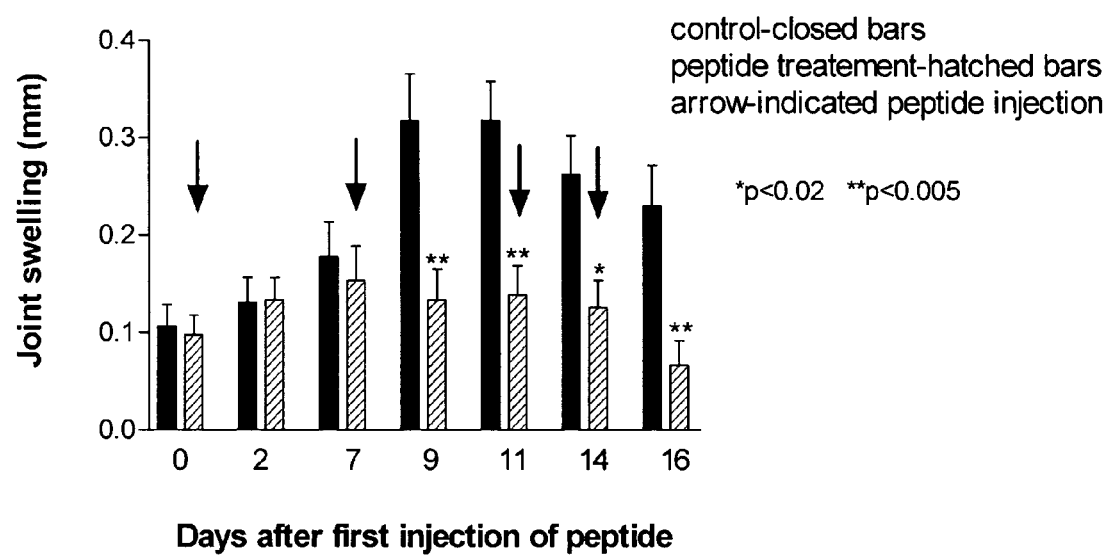
FIG. 12 shows the effect of peptide IIIM1 on arthritic mice. The degree of joint swelling was calculated as the difference in joint thickness between the time intervals indicated in the figure and prior to immunization.

As shown in FIG. 12, IIIM1 peptide was very potent in reducing joint swelling.

Example 14

Effect of IIIM1 and IIIH Peptides on Experimental Autoimmune Encephalitis in Female Mice—a Model for Multiple Sclerosis Female C57BL mice were intracardially injected with 1 mg/kg IIIM1 peptide (n=6) or IIIH peptide (n=5) or the vehicle NaCl 0.9% (n=6) (volume of injection—0.25 ml/animal) under light pentobarbital (15 mg/kg) anesthesia. Immediately thereafter myelin oligodendritic glycoprotein (MOG) 35-55, emulsified with Complete Freund's Adjuvant, was subcutaneously administered into 4 sites on the back, adjacent to each of the forelimbs and hindlimbs, each injection was at volume of 50 µl. Each animal was i.p. injected with pertusis toxin in PBS (200 ng/mouse). The pertusis toxin injection was repeated after 2 days. The animals were evaluated for neurological score from 0 (no effect) to 4 (severe neurological symptoms including paralysis). Results are the mean±SE of neurological score (sum of all scores divided by the number of animals in each experimental groups) at each of the indicated time intervals after immunization.

Figure 13:
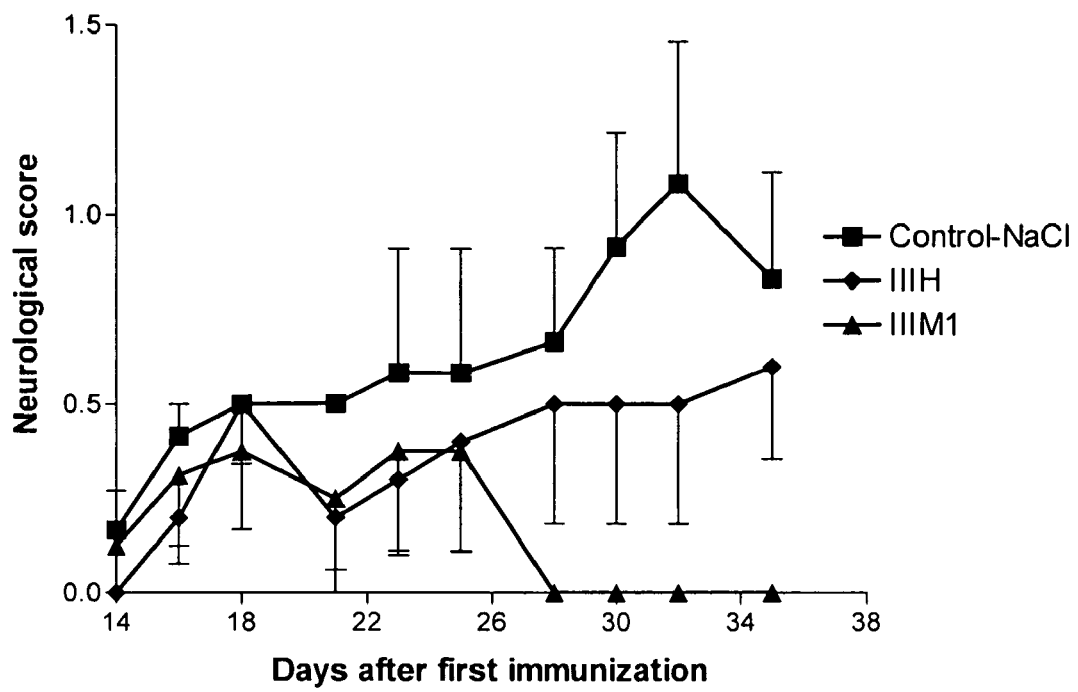
FIG. 13 shows the effect of peptide IIIM1 and a derivative thereof designated IIIH on experimental autoimmune encephalitis in female mice—a model for multiple sclerosis.

FIG. 13 shows the anti-multiple sclerosis effect of IIIM1 peptide and, to a lesser extent, of IIIH peptide.

Example 15

Effect of IIIM1 Peptide on Experimental Autoimmune Encephalitis in Male Mice—a Model for Multiple Sclerosis Male C57BL mice were intracardially injected with 1 mg/kg IIIM1 peptide (n=7) or the vehicle NaCl 0.9% (n=7) (volume of injection—0.25 ml/animal) under light pentobarbital (15 mg/kg) anesthesia. Immediately thereafter, MOG 35-55 emulsified with Complete Freund's Adjuvant was subcutaneously administered into 4 sites on the back, adjacent to each of the forelimbs and hindlimbs, each injection was at volume of 50 µl. Each animal was i.p. injected with pertusis toxin in PBS (200 ng/mouse). The pertusis toxin injection was repeated after 2 days. The animals were evaluated for neurological score from 0 (no effect) to 4 (severe neurological symptoms including paralysis). Results are the mean±SE of neurological score (sum of all scores divided by the number of animals in each of the experimental groups) at each of the indicated time intervals after immunization.

Figure 14:
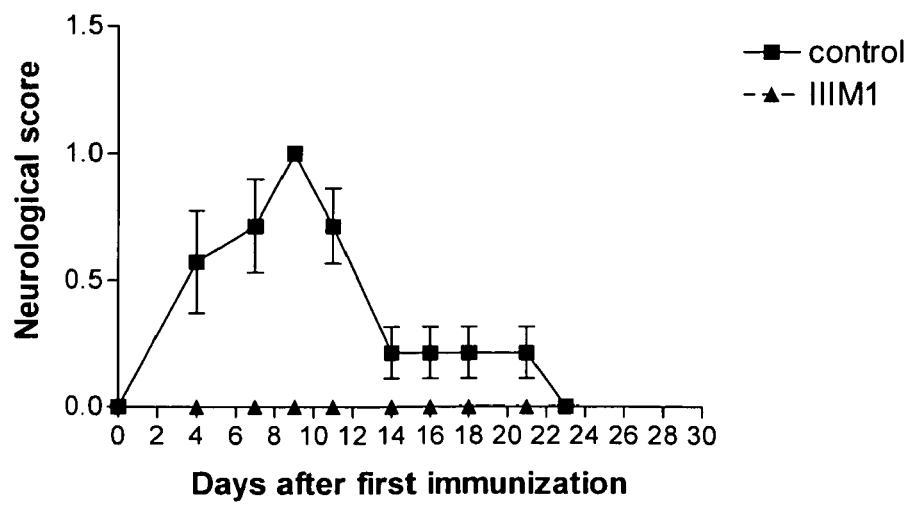
FIG. 14 shows the effect of peptide IIIM1 on experimental autoimmune encephalitis in male mice—a model for multiple sclerosis.

FIG. 14 shows the anti-multiple sclerosis effect of peptide IIIM1.

Example 16

Effect of IIIM1 Peptide on Carrageenan-Induced Inflammation in Mice

Peptide IIIM1 or its vehicle—saline, was injected 7, 5, 3 days and 20 min prior to carrageenan treatment. Carrageenan (50 µl of 3 mg/ml) was injected into the subplantar area of both limbs of each animal. The diameter of the subplantar area was measured every 60 min by a micrometer. The degree of swelling was assessed by the difference between thicknesses measured after and prior to carrageenan injection. Each group (peptide and control) contained 8 mice, namely, 16 limbs.

Figure 15:
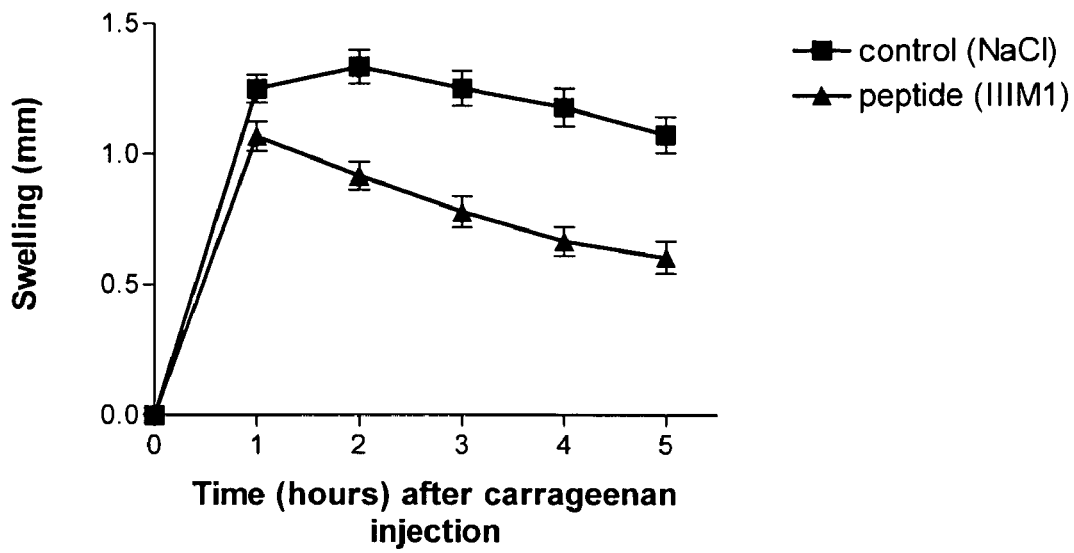
FIG. 15 shows the effect of peptide IIIM1 on carrageenan-induced inflammation in male mice, as a function of time.

FIG. 15 clearly shows the anti-inflammatory effect of IIIM1 peptide.

Example 17

Effect of IIIH and IIIM1 Peptides on Carrageen-Induced Inflammation in Male Rats Peptides or their vehicle—saline, were injected 7, 5, 3 days and 20 min prior to carrageenan treatment (volume of injection 0.25 ml). Carrageenan (100 μl of 1%) was injected into the subplantar area of both limbs of each animal. The diameter of the subplantar area was measured every 60 min by a micrometer. The degree of swelling was assessed by the difference between thicknesses measured after and prior to carrageenan injection. Each group (IIIM1 (n=10), IIIH (n=10) and control—0.9% NaCl (n=8)) was treated as described.

Figure 16:
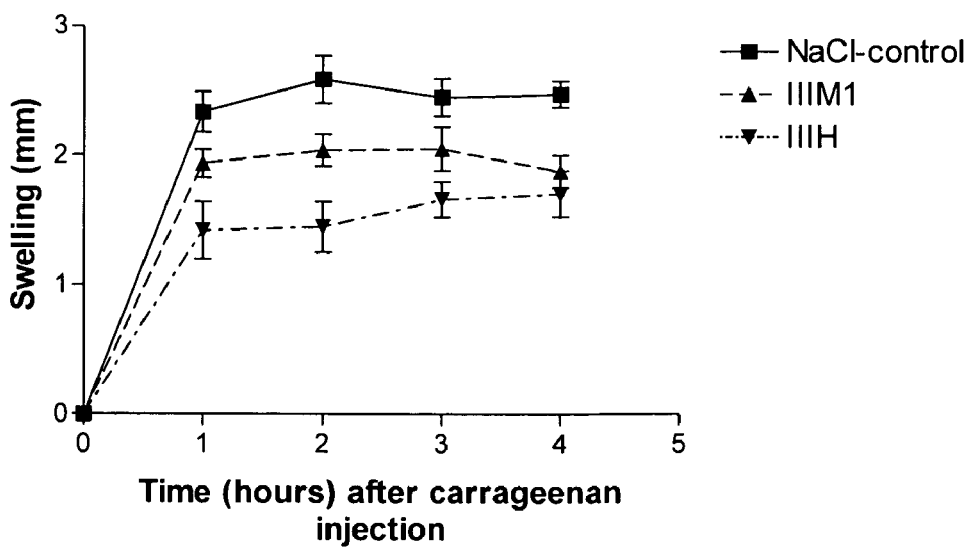
FIG. 16 shows the effect of peptide IIIM1 and a derivative thereof designated IIIH on carrageenan-induced inflammation in male rats, as a function of time.

FIG. 16 clearly demonstrates the anti-inflammatory effect of IIIH peptide and IIIM1 peptide in male rats.

Example 18

Lysophosphatidic Acid (LPA)-Induced Luminescence in MIIIM1 Peptide-Transfected and Control Cells HaCaT cells, an immortalized non-tumorigenic human keratinocyte cell line, were transfected with MIIIM1 peptide having the amino acid sequence of IIIM1 and an additional methionine at the amino terminus to give the following sequence: H-Met-Lys-Gly-His-Tyr-Ala-Glu-Arg-Val-Gly-OH (SEQ ID NO: 82).

Transfection Protocol

Construction of the plasmid: cDNA having the following sequence 5' ATG GCC AAC GCG CTC GGC GTA GTG GCC CTT 3' (SEQ ID NO: 84) was inserted into the pTet plasmid (Gene Bio-application Ltd., Israel) under the transcriptional control of the tet promoter to yield pTet-peptide. Down stream of the sequence, polyadenylation sequence from simian virus 40 was inserted. The plasmid contained a gene for neomycin resistance. pTet plasmid was used as a control plasmid. In addition, the plasmid pCMV-tTa (Gene Bio-application Ltd., Israel), which contained the gene for the tetracycline transactivator under the transcriptional control of the CMV promoter was used.

Transfection of cells: One day before transfection, cells were seeded in a 24 well plate at a concentration of $2 \times 10^5$ cells/well in a volume of 500 μl in order to reach 90-95% confluence on the day of transfection. The following DNA-lipofectamine (Invitrogen, CA, USA) complexes were prepared as follows: 2 μl of lipofectamine was mixed with 50 μl of the appropriate serum free medium and incubated for 5 minutes at room temperature; 0.8 μg of each of the plasmids: pTet-peptide, pTet, or pCMV-tTA were mixed with 50 μl of the appropriate serum free medium and combined with the lipofectamine complex. After gentle mixing, the complex was incubated for 20 minutes at room temperature to allow the DNA-lipofectamine complex to form. To each well were added the pTet-peptide-lipofectamine complex, pTet-lipofectamine complex and the pCMV-tTa-lipofectamine complex. The cells were incubated at 37° C. in a humidified incubator supplemented with 94% air/6% $CO_2$. Two days after transfection, the cells were removed to a 25-diameter flask with fresh medium. Twenty-four hours later, 200 μg/ml of G418 (Gibco-BRL) and 1 μg/ml Doxycycline were added to the medium. The G418 concentration was increased in the following two weeks and reached a final concentration of 1000 μg/ml.

Cell Culture

Two types of HaCaT cells were used: a) the peptide-transfected cells, which contained the plasmid comprising the cDNA encoding the peptide; the cells expressed the peptide, b) control cells that were transfected with the plasmid without the peptide polynucleotide; the cells did not express the peptide.

Each of the HaCaT cell lines was grown in Dulbecco's modified Eagle's medium/F-12 containing 10% fetal calf serum, 4 mM Glutamine, 100 units/μl penicillin, 100 μg/ml streptomycin and 250 ng/ml amphotericin B at 37° C. in a humidified incubator supplemented with 94% air/6% $CO_2$. Cells were grown in a 25 diameter flask in a volume of 3 ml. Splitting was performed every 3-4 days by removal of the medium and addition of trypsin. Once the cells were trypsinized, conditioning with the same volume of medium was performed followed by centrifugation at 4000 rpm for 7 minutes. The trypsin-medium was removed, the cells were resuspended and transferred to a fresh medium so the final concentration of cells was diluted to $\frac{1}{10}$ of the initial value. After splitting, the cells were grown in serum-free medium for 24 hours.

Experimental Approach

Exposure of HaCaT cells to lysophosphatidic acid (LPA) resulted in production of hydrogen peroxide that could be monitored by conversion to hydroxyl radicals by horseradish peroxidase. The formed radical could be monitored by luminescence in the presence of luminol.

Luminescence Assay

The reaction mixture contained 0.2 ml cells ($10^6$/ml) suspended in Hank's balanced salt solution (HBSS), luminol (200 μM), horseradish peroxidase (1.0 unit/ml), and fatty acid free bovine serum albumin (0.2%). The reaction was started by lysophosphatidic acid (LPA) at the indicated concentrations. The reaction was performed in a 96-well plate, using Tecan spectrofluoro Plus for luminescence measurement. Each point represents 3 different measurements taken at the peak response of luminescence.

Cytotoxicity Assay

The cells were pre-incubated with the tested peptide for 4 hours then exposed to SM (1 μM) or hydrogen peroxide (1 mM) for 24 hours. Cell Viability was determined by the MTT assay, based on production of blue crystals of formazan. The intensity of the blue color (absorbance at 405 nm determined by ELISA reader) is proportional to the number of viable cells.

Figure 17:
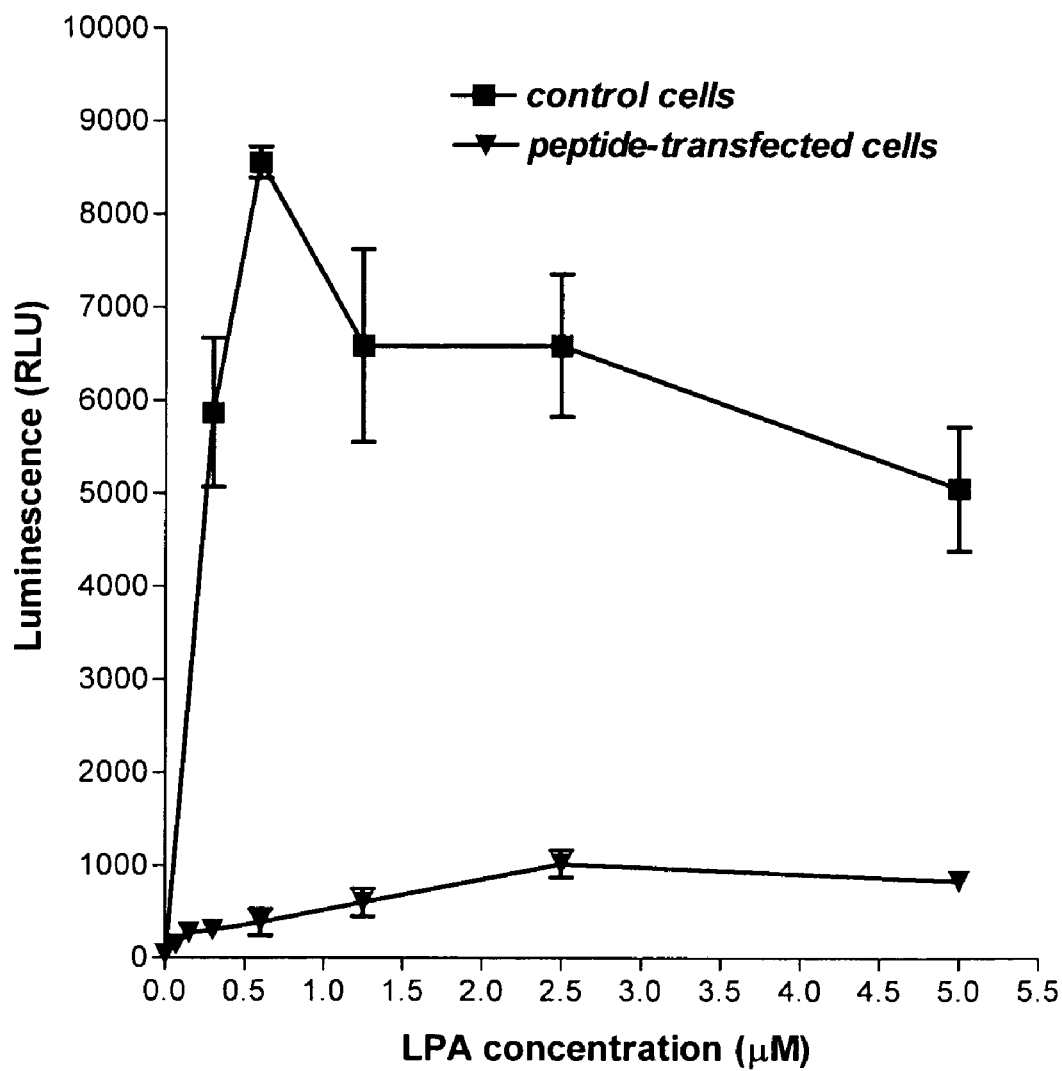
FIG. 17 shows the lysophosphatidic acid (LPA)-induced luminescence in peptide MIIIM1-transfected cells and control cells.

FIG. 17 clearly shows that the peptide-transfected cells exhibited significantly lower luminescence than the control cells, probably due to their high content of the peptide, which scavenged the radicals formed by the LPA-induced hydrogen peroxide.

Example 19

Effect of Hydrogen Peroxide on Cell Viability of MIIIM1 Peptide-Transfected Cells and Control HaCaT Cells The cells were prepared and maintained as described in Example 18 herein above. Cells ($0.5 \times 10^6$) were exposed to 500 μM hydrogen peroxide. MTT (Sigma USA) viability test was carried out after 24 hours by Tecan SpecrtoFluoroPlus (Tecan GmbH, Austria).

Figure 18:
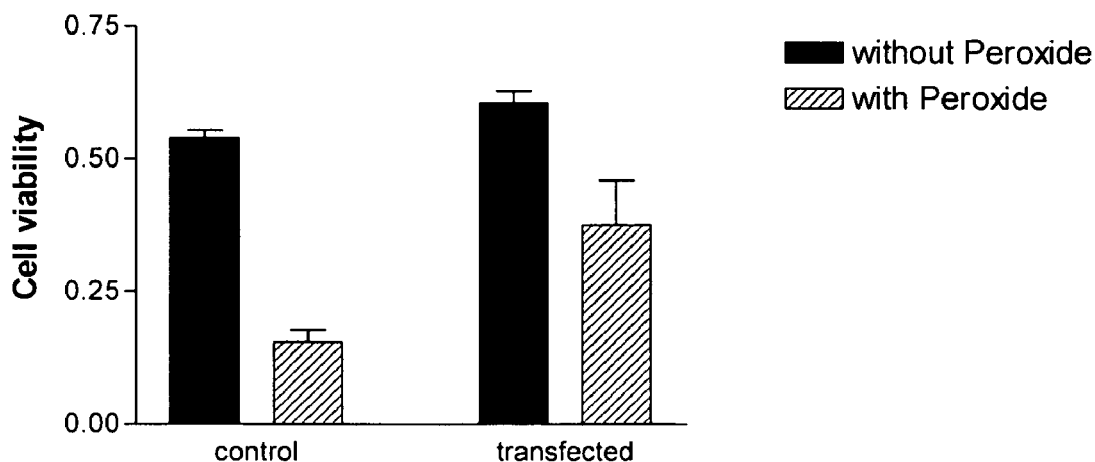
FIG. 18 shows the effect of hydrogen peroxide on cell viability of peptide MIIIM1-transfected cells and control HaCaT cells.

FIG. 18 shows that the control cells were vulnerable to hydrogen peroxide, namely, viability of the control cells was reduced by 71%. However, the MIIIM1 peptide-transfected cells were shown to be more resistant to hydrogen peroxide and showed reduction of viability of only 38% upon exposure to hydrogen peroxide.

Example 20

Effect of Sulfur Mustard (SM) on Cell Viability of MIIIM1 Peptide-Transfected Cells and Control HaCaT Cells The cells were prepared and maintained as described in Example 18. Cells ($0.5 \times 10^6$) were exposed to 1 µM SM. The bars represent peptide-transfected cells without peptide or with exposure to SM (peptide+SM) and control cells without (control) or with exposure to SM (control+SM). MTT viability test was carried out after 24 hours.

Figure 19:
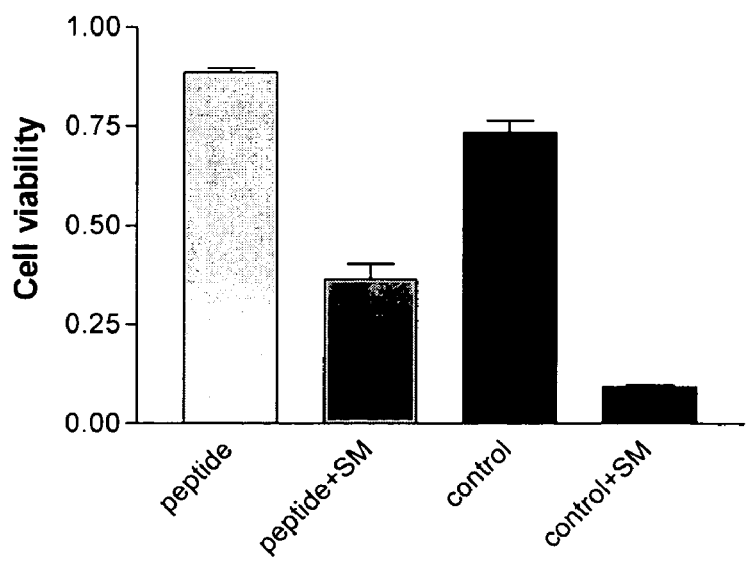
FIG. 19 shows the effect of sulfur mustard (SM) on cell viability of peptide MIIIM1-transfected cells and control HaCaT cells.

FIG. 19 shows that the control cells are more vulnerable to SM, namely, viability of control cells was reduced by 87% whereas the peptide-transfected cells were more resistant and showed reduction of only 59% upon exposure to SM.

Example 21

Effect of IIIM1 on SM-Induced Cytotoxicity in HaCaT Cells

HaCaT cells were pre-incubated with the tested peptide for 4 hours then exposed to SM (1 µM) for 24 hours. Cell Viability was determined by the MTT assay, based on production of blue crystals of formazan. The intensity of the blue color (absorbance at 405 nm determined by ELISA reader) is proportional to the number of viable cells.

Figure 20:
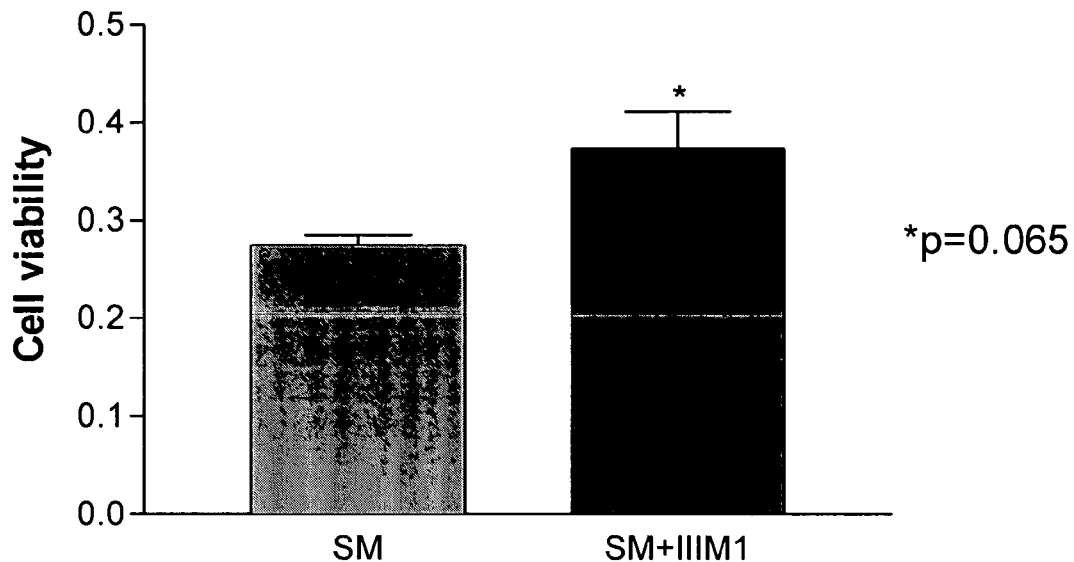
FIG. 20 shows the effect of IIIM1 peptide on SM-induced cytotoxicity in HaCaT cells.

As shown in FIG. 20, the IIIM1 peptide (30 µg/ml) increased the number of viable cells exposed to SM. Thus, the IIIM1 peptide is capable of reducing the cytotoxic effect of SM in HaCaT cells.

Example 22

Effect of IIIM1 Peptide Fragments on $H_2O_2$-Induced Cytotoxicity in HaCaT Cells HaCaT cells were pre-incubated with KGHY (10 µg/ml) or AERVG (10 µg/ml) or a mixture of KGHY (10 µg/ml) and AERVG (10 µg/ml) for 4 hours. Thereafter, hydrogen peroxide was added (1 mM) to the medium, which contained 10% heat-inactivated serum, and the cells were incubated for additional 24 hours. Cell Viability was determined by the MTT assay, based on production of blue crystals of formazan. The intensity of the blue color (absorbance at 405 nm determined by ELISA reader) is proportional to the number of viable cells.

Figure 21:
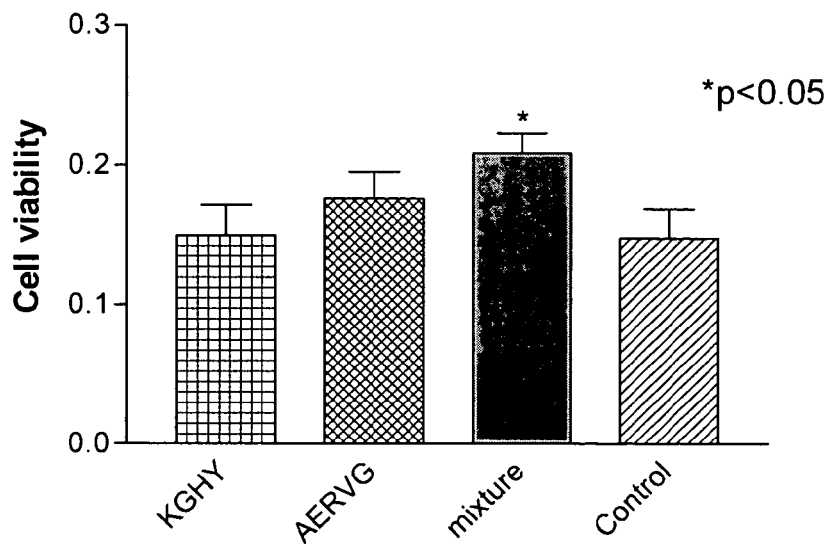
FIG. 21 shows the effect of IIIM1 peptide fragments on $H_2O_2$-induced cytotoxicity in HaCaT cells.

FIG. 21 shows that a mixture of IIIM1 fragments, namely KGHY and AERVG increased the number of viable cells exposed to $H_2O_2$. In other words, a mixture of fragments of IIIM1 reduced the cytotoxic effect of $H_2O_2$ in HaCaT cells. The fragment AERVG alone also exhibited a beneficial effect, though it was lower than that obtained by the mixture.

Example 23

Effect of a IIIM1 Peptide Fragment on $H_2O_2$-Induced Cytotoxicity in HaCaT Cells HaCaT cells were pre-incubated for 4 hours with the indicated concentrations of a IIIM1 peptide fragment designated fragment 5. Thereafter, hydrogen peroxide (final concentration of 1 mM) was added to the medium (which contained 10% heat-inactivated serum). Twenty four hours later, cell viability was determined by MTT test.

Figure 22:
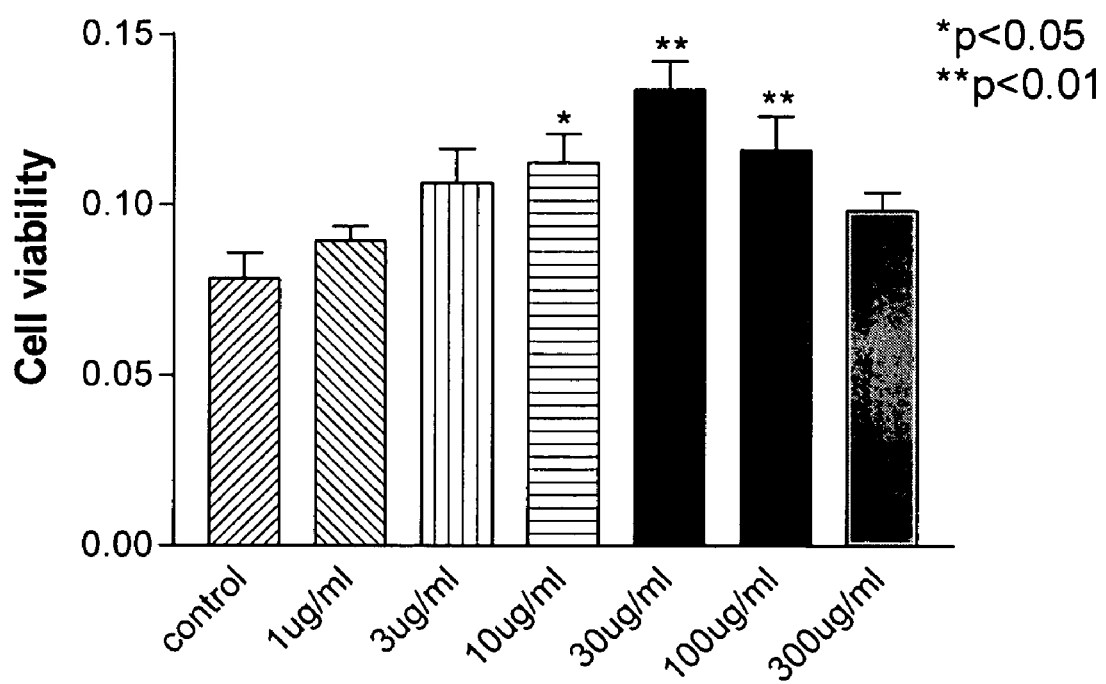
FIG. 22 shows the effect of a IIIM1 peptide fragment designated Fragment 5 on $H_2O_2$-induced cytotoxicity in HaCaT cells.

As shown in FIG. 22, concentrations of 10, 30 and 100 µg/ml fragment 5 increased significantly the number of viable cells exposed to $H_2O_2$.

Example 24

Effect of Oral Administration of IIIM1 or IIIM1C Peptides on Experimental Autoimmune Encephalitis Female C57BL/6 mice (20-23 g) were injected subcutaneously into 4 sites on the back, adjacent each of the forelimbs and hindlimbs (total volume 200 µl), with 200 µg myelin oligodendrocyte glycoprotein (MOG) 35-55 emulsified with 100 µl complete Freund's adjuvant, 800 µg *Mycobacterium tuberculosis* H37RA (Difco, Detroit, Mich.) and 80 µl phosphate buffered saline. Thereafter, each animal was i.p. injected with pertusis toxin (PTX; 200 ng/mouse) and an additional PTX injection was repeated two days later. The IIIM1 peptide dissolved in saline was orally administered on the 7 day (day of onset of neurological symptoms), 9, 12, 14, 16, and 19 days after MOG administration (marked by arrows) at the indicated doses. The animals were evaluated for neurological score as follows: 0=normal; 1=limp tail or mild hindlimb weakness; 2=moderate hindlimb weakness or mild ataxia; 3=moderate to severe hindlimb weakness; 4=severe hindlimb weakness or mild forelimb weakness or moderate ataxia; 5=paraplegia with no more than moderate forelimb weakness; and 6=paraplegia with severe forelimb weakness or severe ataxia or moribund condition. *p<0.02, **p<0.01 in comparison to control (NaCl); n=11 animals for each group except for control (n=12).

Figure 23:
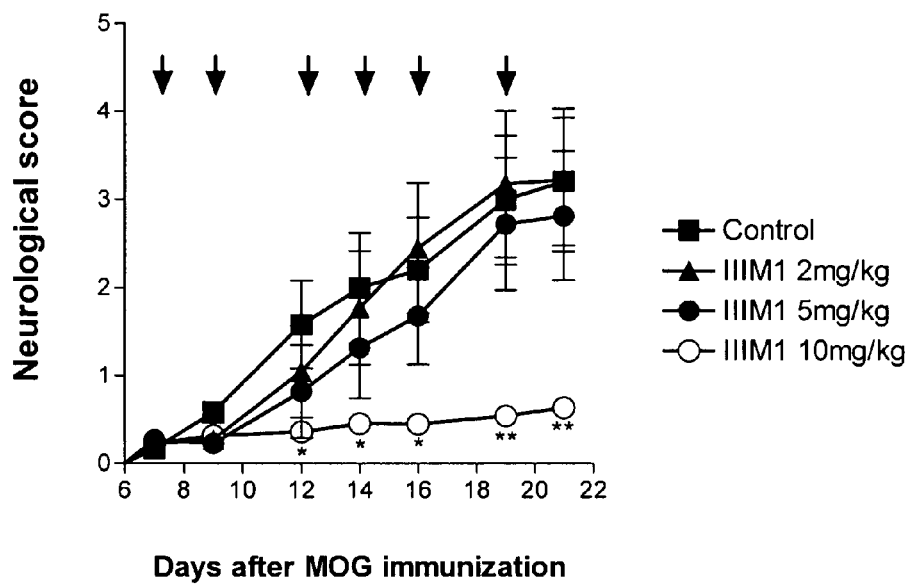
FIG. 23 shows the effect of oral administration of increasing doses of IIIM1 peptide on experimental autoimmune encephalitis in mice.

FIG. 23 shows that IIIM1 peptide orally administered to mice at a dose of 10 mg/kg body weight efficiently eliminates the neurological symptoms in EAE mice.

To detect the effect of IIIM1C, the experiment was performed as above except that the IIIM1C peptide having the amino acid sequence KGHYAERVGC (SEQ ID NO: 90) or IIIM1 peptide were orally administered on the 9 day (day of onset of neurological symptoms), 11, 14, 18, 21, 23, 25 and 28 days after MOG administration (marked by arrows) at a dose of 10 mg/kg for each administration. Neurological effects were scored and quantified as detailed herein above. *p<0.05, **p<0.01 in comparison to control (NaCl); n=10 animals for NaCl and IIIM1C groups; n=9 animals for IIIM1.

Figure 24:
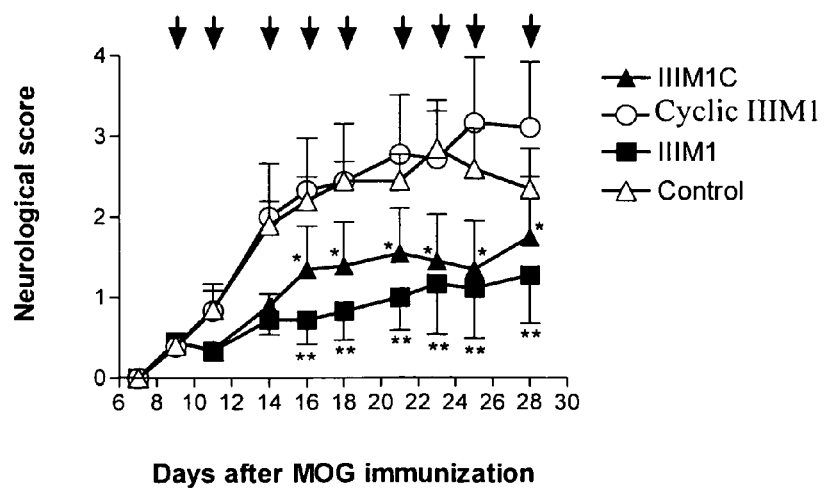
FIG. 24 shows the effect of oral administration of IIIM1, IIIM1C, or a cyclic analog of IIIM1 peptide on experimental autoimmune encephalitis in mice.

FIG. 24 shows that IIIM1 or IIIM1C when administered orally to EAE mice reduced the neurological symptoms associated with the disease. The cyclic analog of IIIM1, cycloaminohexyl (K-G) IIIM1, was ineffective in reducing the neurological symptoms in EAE mice.

Example 25

Effect of i.p. Administration of IIIM1C or IIIM1 on EAE Model

Female C57BL/6 mice (20-23 g) were injected subcutaneously into 4 sites on the back, adjacent each of the forelimbs and hindlimbs (total volume 200 µl), with 200 µg myelin oligodendrocyte glycoprotein (MOG) 35-55 emulsified with 100 µl complete Freund's adjuvant, 800 µg *Mycobacterium tuberculosis* H37RA (Difco, Detroit, Mich.) and 80 µl phosphate buffered saline. Thereafter, each animal was i.p. injected with pertusis toxin (PTX; 200 ng/mouse) and an additional PTX injection was repeated two days later. IIIM1C (KGHYAERVGC) dissolved in saline, was i.p. injected (1 mg/kg for each administration) at onset of neurological symptoms 9 (day of onset) 11, 14, 16, 18, 21, 23, 25, 28 days (marked with arrows) after MOG injection. Neurological effects were scored and quantified. *p<0.01 in comparison to control; n=10 animals for each group.

Figure 25:
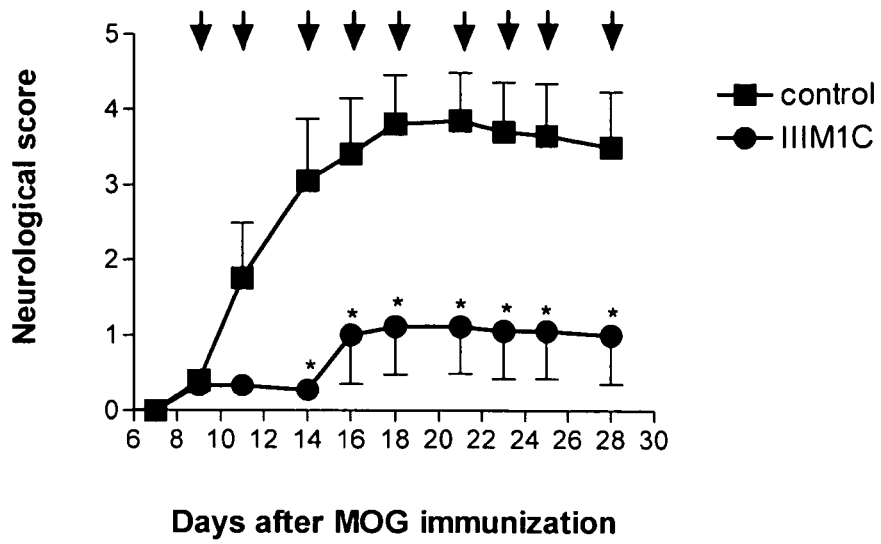
FIG. 25 shows the effect of intraperitoneal (i.p.) administration of IIIM1C peptide on experimental autoimmune encephalitis in mice.
Figure 26:
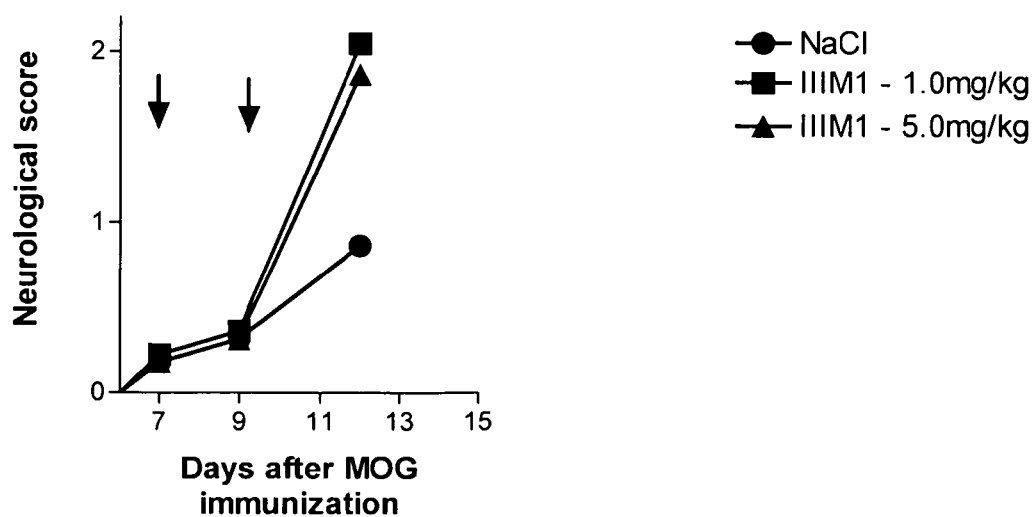
FIG. 26 shows the effect of i.p. administration of IIIM1 peptide on experimental autoimmune encephalitis in mice.

FIG. 25 shows that the neurological score was significantly improved after multiple i.p. administrations of IIIM1C To examine the i.p. administration of IIIM1 on EAE mice, the experiment was performed as described herein above for IIIM1C except that the animals were injected i.p. only twice. As shown in FIG. 26, after the second injection the IIIM1-treated animals showed severe neurological symptoms, more than those of the controls. Therefore, the experiment was terminated.

Example 26

Hydroxy Radical Scavenging Effect of IIIM1C

Horseradish peroxidase (5 µl of 100 µg/ml), luminol (2 µl of 10 µM) and IIIM1C (2 µl) were incubated in Hank's balanced salt solution (HBSS) (200 µl) (final concentrations of the peptide in the reaction mixture are indicated in the figure). The reaction started by the addition of 5 µl of 7.5 mg/ml Glucose Oxidase. The reaction was performed in 96 well plate. Luminescence was measured by Tecan SpecrtoFuoroPlus (Tecan GmbH, Austria).

Figure 27:
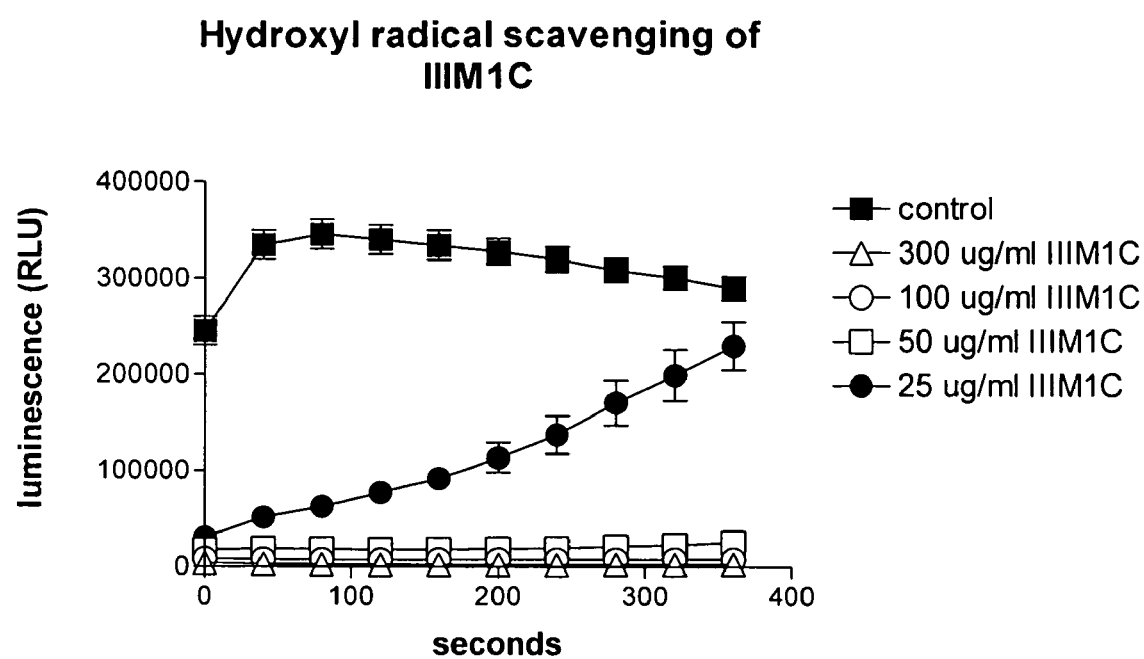
FIG. 27 shows the effect of IIIM1C peptide on hydroxy radical scavenging.

FIG. 27 shows the activity of the IIIM1C peptide in scavenging free hydroxyl radicals as a function of the concentration of the peptide.

Example 27

Effect of IIIM1 on Peritonitis

Mice (C57BL/6) were injected i.v. with IIIM1 (1 mg/kg) or phosphate buffered saline (control). Peritonitis was induced in both groups by i.p. administration of thioglycolate. Three days later mice were sacrificed and peritoneal lavage was carried out to obtain peritoneal macrophages. Total number of isolated cells was quantified using trypan blue staining. n=6 animals for both groups; *p<0.05.

Figure 28:
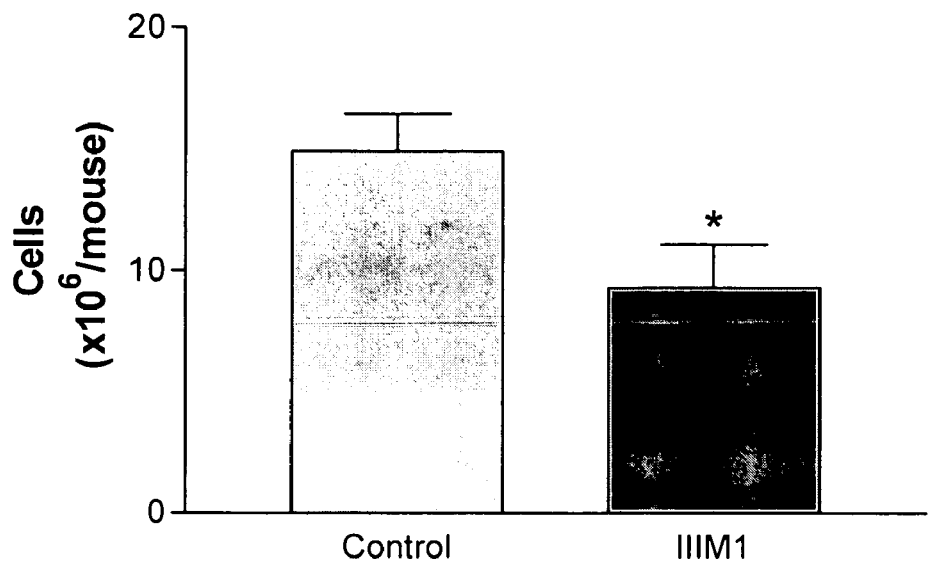
FIG. 28 shows the effect of IIIM1 peptide on peritonitis in mice.

As shown in FIG. 28, IIIM1 can reduce the cell number in the peritoneal lavage.

SJL mice were immunized with proteolytic protein (PLP; 139-151). IIIM1 (10 mg/kg) was orally administered 3 times a week starting on day of immunization. Ten days after immunization drain lymph nodes were harvested and cells were counted. n=8 animals for each group; ***p=0.0006.

Figure 29:
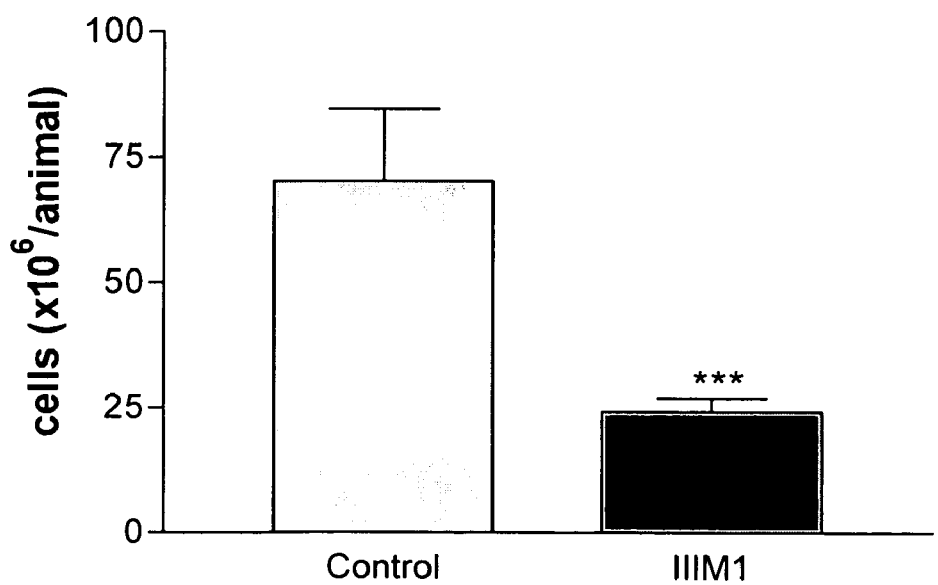
FIG. 29 shows the effect of IIIM1 peptide on cell number in drain lymph nodes in mice.

As shown in FIG. 29, IIIM1 significantly reduced the number of cells in drain lymph nodes.

Example 28

Effect of IIIM1 on Glucose-Induced Edema

Male mice were injected intradermally with 64 mg glucose oxidase (GO) with or without 25 mg IIIM1 in a total volume of 50 ml of saline. Diameter of edema was measured once every 2 hours using a ruler.

Figure 30:
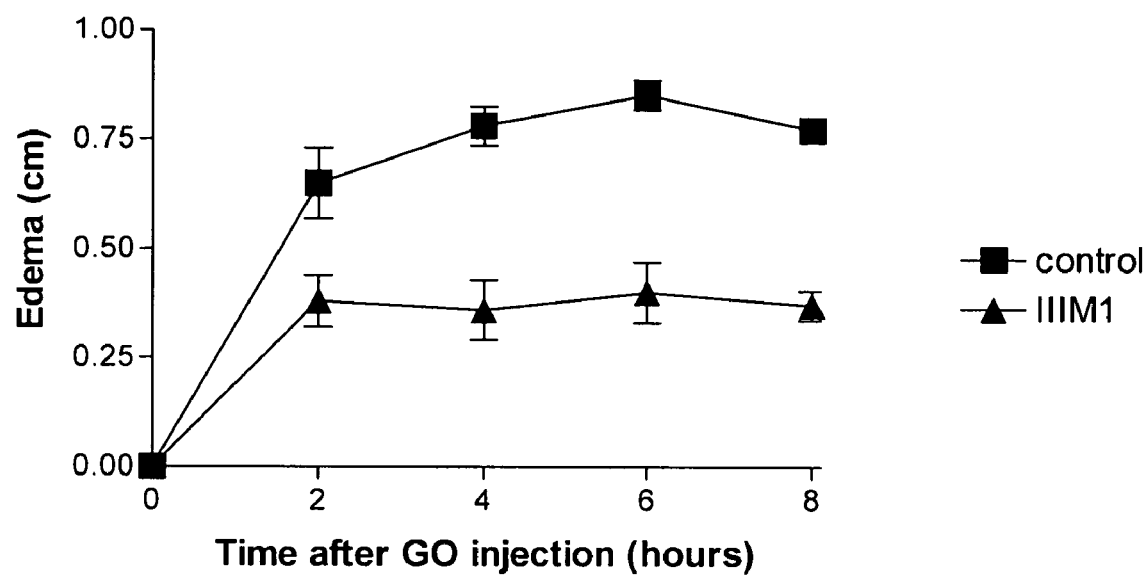
FIG. 30 shows the effect of IIIM1 peptide on glucose oxidase-induced edema in mice.

As shown in FIG. 30, peptide IIIM1 was highly efficient in reducing the diameter of edema.

Example 29

Effect of IIIM1 on the Manifestation of Parkinson's Disease in a Mice Model

Animals

Peptide treatment: IIIM1 (10 mg/kg/administration) was injected orally 8, 6, 4 and 1 days prior to methylphenyl tetrahydropyridine (MPTP) exposure, and 1 and 3 days post MPTP exposure. Control animals received four injections of physiological saline. MPTP model is typically used as an animal model for Parkinson's disease.

MPTP exposure: The mice received four intraperitoneal (i.p.) injections of MPTP HCl (20 mg/kg) (Sigma, St. Louis, Mo., USA) at 2-h intervals, with a total dose of 80 mg/kg. Control animals received four injections of physiological saline.

Experimental groups: Mice were divided into 4 groups (each n=7): pure control-received saline only; IIIM1 control-received IIIM1 only; IIIM1 MPTP-received IIIM1 and MPTP; MPTP-received MPTP only. The appropriate groups received the matched saline injections, namely, pure control group was given both oral and i.p. saline injections, IIIM1 control received i.p injections, and MPTP group received oral saline injections.

Behavioral Tests

Motor coordination test: In the pole test, which measures motor coordination, the mouse was placed head upward near the top of a vertical rough-surfaced pole (diameter 8 mm, height 45 cm). The time taken to turn completely downward (time to turn; T-turn) and the time until the mouse reached the floor (locomotion activity time; T-LA) were recorded.

The catalepsy test: Both forepaws of the mouse were placed on a horizontal bar (diameter 0.2 cm), which was elevated 15 cm from the floor. The time during which the animals maintained this position before lifting their hindpaws onto the bar was recorded.

Open field test: The mice were placed on an area of 48×48 cm, divided into squares of 24×24 cm. Times of crossing the boarders of the squares was recorded during 3 min for each mouse.

Dopamine Determination

The brains were removed and the striatum was dissected on an ice-cold glass Petri dish. The tissue samples were weighed immediately, frozen, and stored at 80° C. until assay. The brain tissues were sonicated in ice-cold 0.2 M perchloric acid containing 100 ng/ml isoproterenol as internal standard. The homogenates were centrifuged at 3000 rpm for 15 min at 4° C. The supernatant was filtered and aliquots were collected for the measurement of the concentrations of dopamine using high-performance liquid chromatography with an electrochemical detector.

Figure 31:
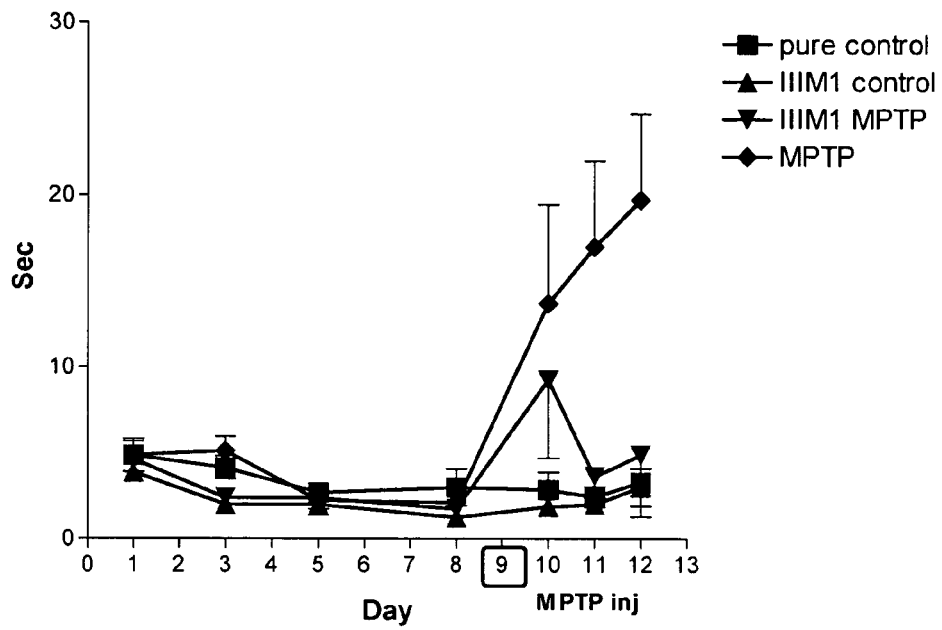
FIG. 31 shows the effect of IIIM1 peptide on the turning time downward in methylphenyl tetrahydropyridine (MPTP)-treated mice.
Figure 32:
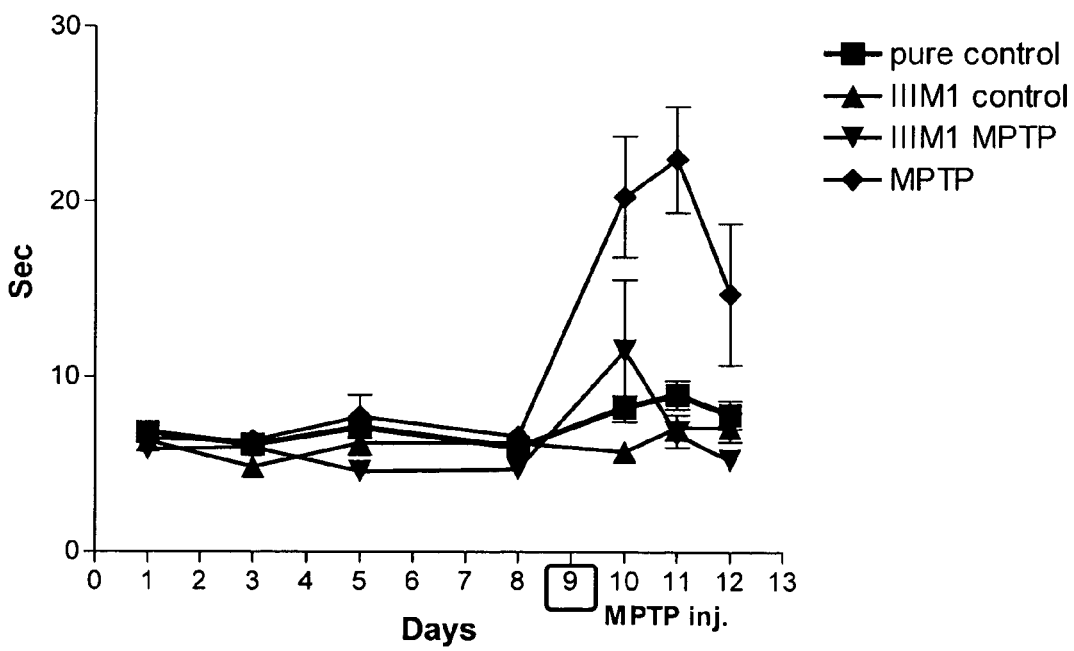
FIG. 32 shows the effect of IIIM1 peptide on locomotion activity time in MPTP-treated mice.
Figure 33:
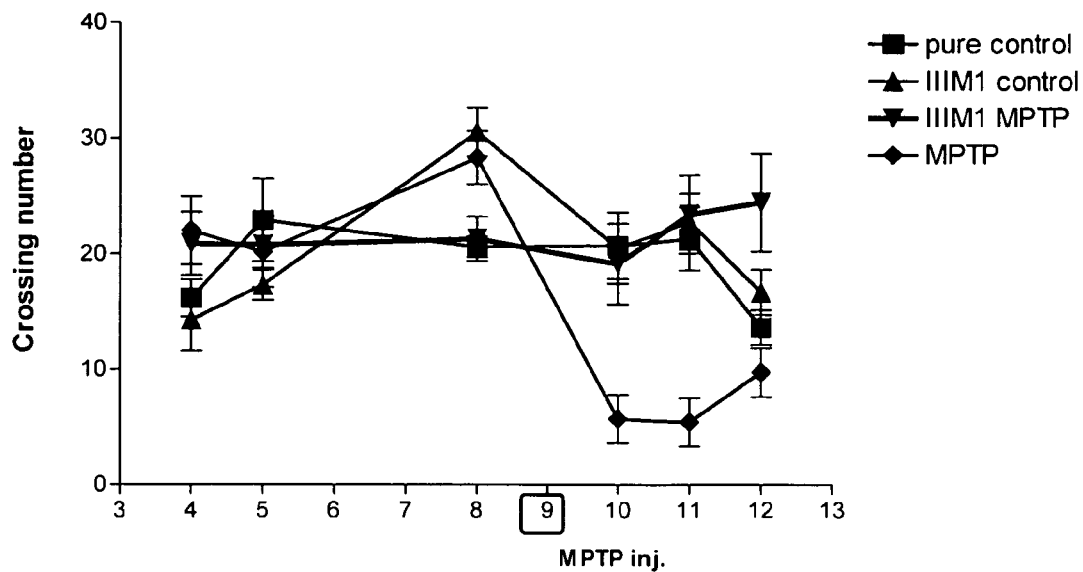
FIG. 33 shows the effect of IIIM1 peptide on the time required to cross an area in MPTP-treated mice.
Figure 34:
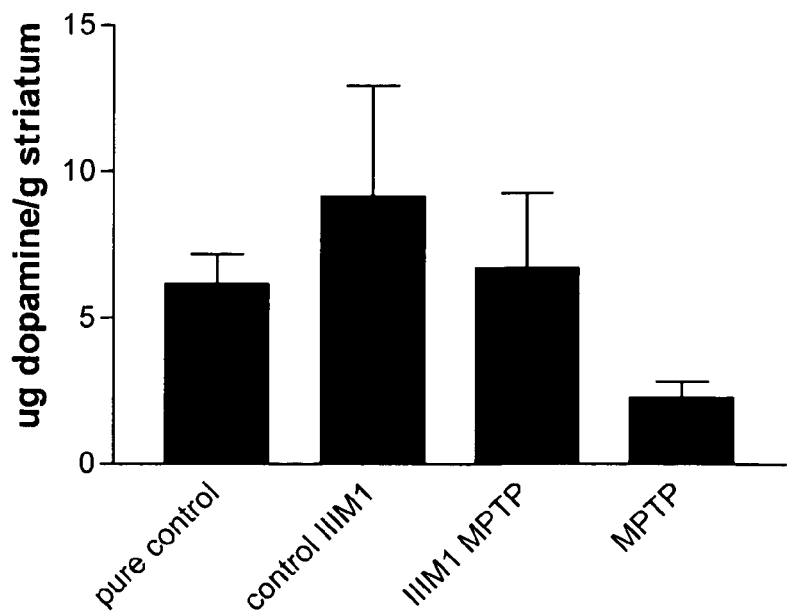
FIG. 34 shows the effect of IIIM1 peptide on dopamine levels in the striatum of MPTP-treated mice.

FIGS. 31-33 show the efficacy of IIIM1 peptide to inhibit the behavioral manifestations of Parkinson's disease in MPTP-treated mice. FIG. 34 shows the efficacy of IIIM1 peptide to prevent the reduction of dopamine levels in mouse striatum as a result of MPTP treatment.

Example 30

Effect of IIIM1 on LPS-Induced Mortality in Mice

Figure 35:
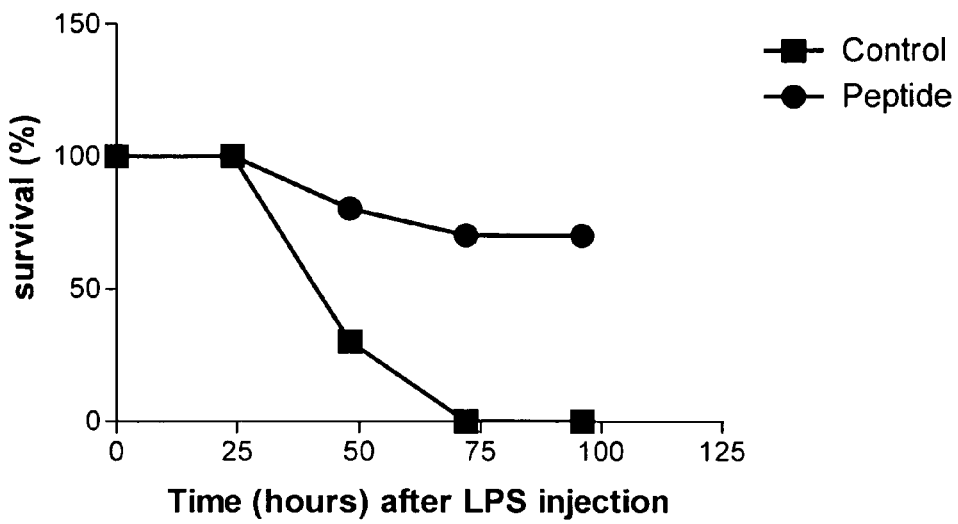
FIG. 35 shows the effect of IIIM1 peptide on the mortality of lipopolysaccharide (LPS)-treated mice.
Figure 36:
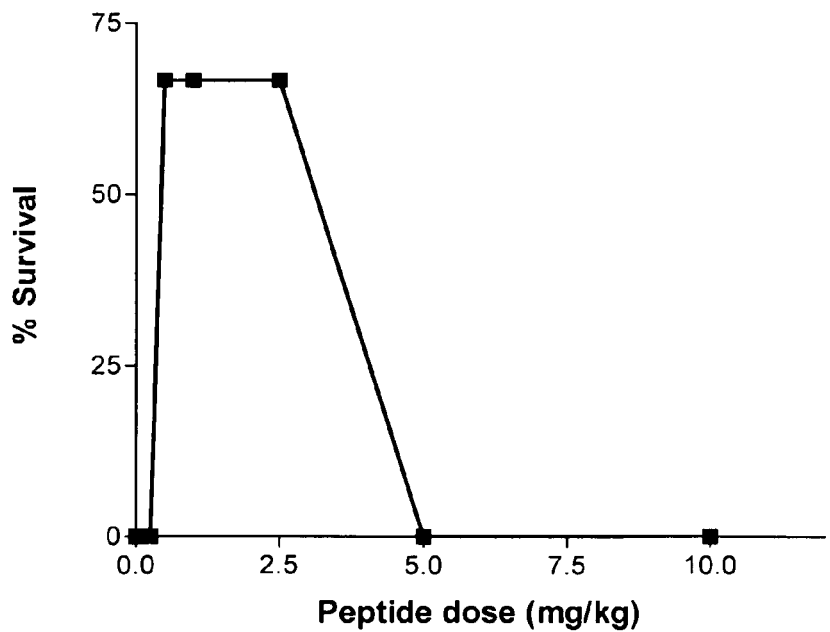
FIG. 36 shows the effect of different IIIM1 peptide doses on LPS-induced mortality in mice.
Figure 37:
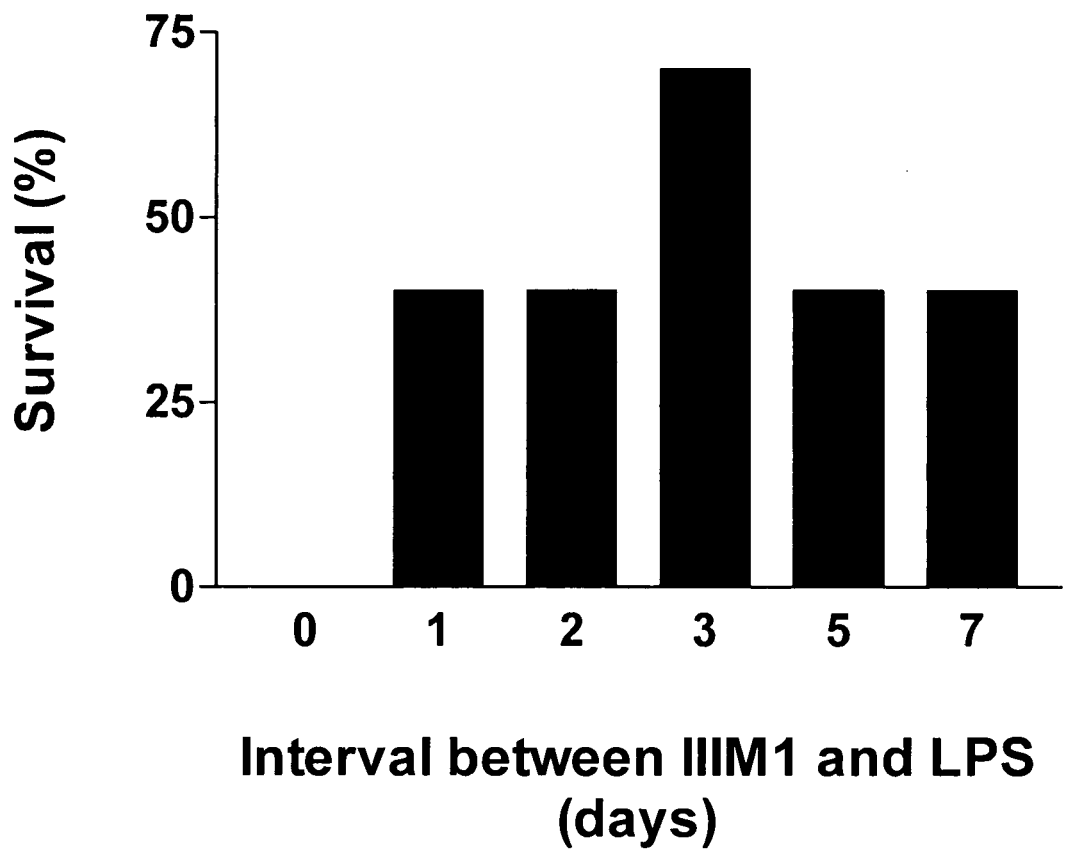
FIG. 37 shows the effect of different time intervals between peptide administration and LPS injection on mortality in mice.
Figure 38A:
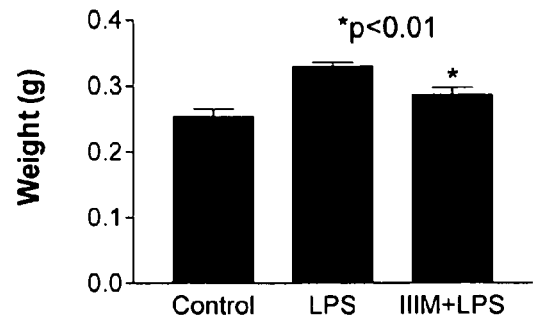
FIG. 38A-D show the effect of IIIM1 peptide on the weight of kidney, spleen, liver, and lung in LPS-treated mice.
Figure 38B:
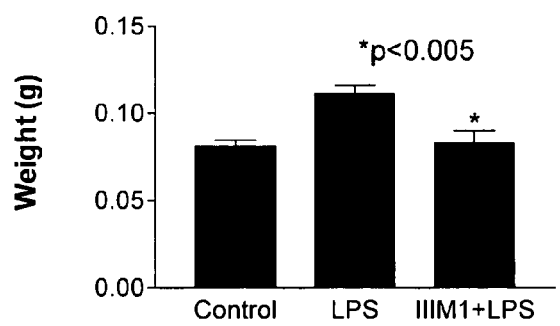
Figure 38C:
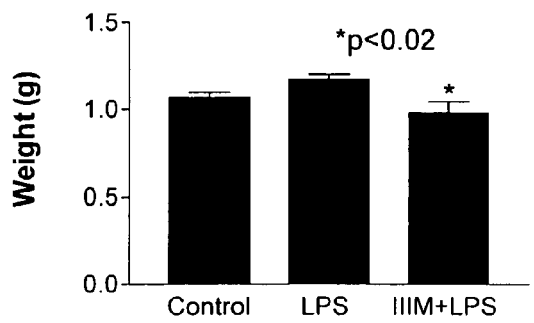
Figure 38D:
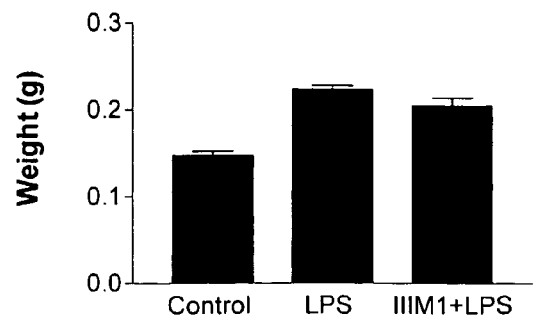

Lipopolysaccharide (LPS)-induced mortality is known to be an animal model for sepsis. To test the effect of IIIM1 on LPS-induced mortality in mice, mice were i.v. administered (single treatment) with IIIM1 (1 mg/kg) or saline (control) 3 days prior to LPS injection (1.2 mg/mouse, i.p.). As shown in FIG. 35, IIIM1 peptide was shown to reduce LPS-induced mortality in mice. The IIIM1 doses which demonstrate pronounced reduction in LPS-induced mortality were found to be from 0.5 to 2.5 mg/kg of mouse body weight (FIG. 36). As shown in FIG. 37, 3-hr interval between IIIM1 administration and LPS injection achieved the higher survival values. IIIM1 was also found to reduce the weight gain of kidney, spleen, liver and lung in LPS-treated mice (FIGS. 38A-D).

Example 31

Figure 39A:
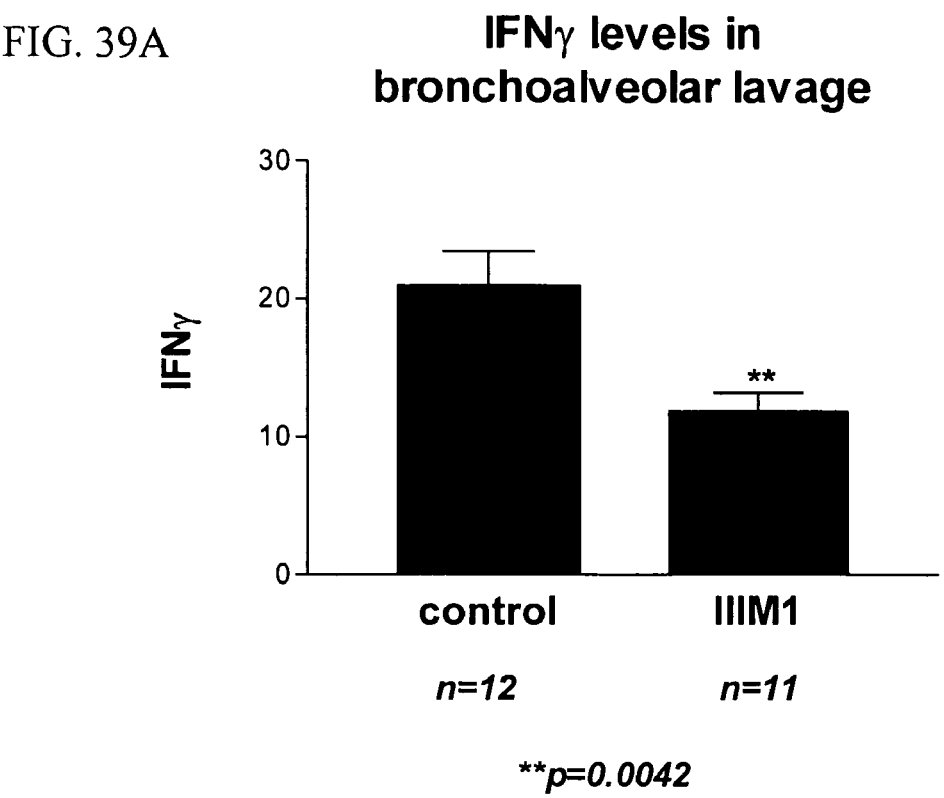
FIG. 39A-B show the effect of IIIM1 peptide on cytokine levels in bronchoalveolar lavage of sulfur mustard-treated mice.
Figure 39B:
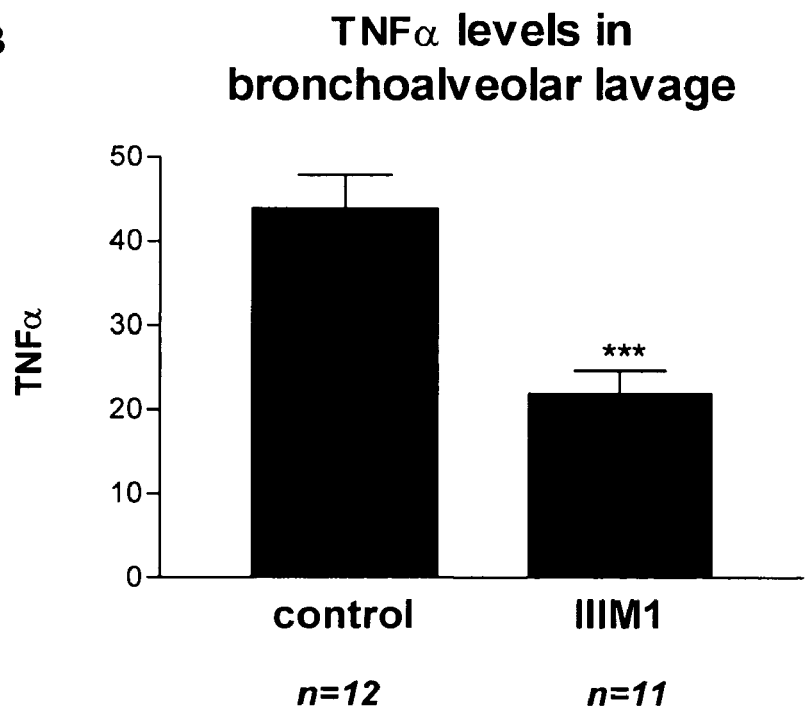

Effect of IIIM1 on Cytokine Levels in Bronchoalveolar Lavage of Sulfur Mustard-Treated Mice Mice were administered i.p. with IIIM1 peptide (1 mg/kg) or saline. Six days later, the mice were exposed to diluted sulfur mustard (SM; 0.006 mg) by tracheal instillation. The animals were sacrificed after 24 hours. Bronchoalveolar lavage (BAL) was prepared and the fluid obtained was assayed for cytokine levels (ng/ml). As shown in FIGS. 39A-B, IIIM1 peptide reduced significantly the level of INFγ and TNFα in bronchoalveolar lavage Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification. In addition, citation or identification of any reference in this application shall not be construed as an admission that such reference is available as prior art to the present invention.

What is claimed is:

1. A nine amino acid peptide consisting of the amino acid sequence as set forth in any one of SEQ ID NOS: 7-30 and in any one of SEQ ID NOS:32-42, wherein the peptide has at least one activity selected from the group consisting of anti-inflammatory activity, free radical scavenging activity, metal chelating activity, metalloproteinase inhibitory activity, and T cell inhibitory activity.

2. A peptide of five to eight amino acid residues consisting of the amino acid sequence as set forth in any one of SEQ ID NOS: 44-47, 49, 50, 52-54, 61-62, 64, and 65, wherein the peptide has at least one activity selected from the group consisting of anti-inflammatory activity, free radical scavenging activity, metal chelating activity, metalloproteinase inhibitory activity, and T cell inhibitory activity.

3. A peptide having ten to sixteen amino acid residues having an amino acid sequence as set forth in any one of SEQ ID NOS: 67-83, wherein the peptide has at least one activity selected from the group consisting of anti-inflammatory activity, free radical scavenging activity, metal chelating activity, metalloproteinase inhibitory activity, and T cell inhibitory activity.

4. A peptide having the amino acid sequence KGHYAERVGC set forth in SEQ ID NO:90 or a peptide derivative thereof, wherein the peptide derivative is selected from the group consisting of an N-acetylated peptide, C-amidated peptide, and an N-acetylated and C-amidated peptide, the peptide or peptide derivative has at least one activity selected from the group consisting of anti-inflammatory activity, free radical scavenging activity, metal chelating activity, metalloproteinase inhibitory activity, and T-cell inhibitory activity.

5. The peptide according to claim 4 having the amino acid sequence set forth in SEQ ID NO:90.

6. A pharmaceutical composition comprising as an active ingredient a peptide according to claim 1 and a pharmaceutically acceptable earner.

7. A pharmaceutical composition comprising as an active ingredient a peptide according to claim 4 and a pharmaceutically acceptable carrier.

8. The pharmaceutical composition according to claim 7, wherein the peptide has the amino acid sequence as set forth in SEQ ID NO:90.

9. A pharmaceutical composition comprising as an active ingredient a peptide according to claim 2 and a pharmaceutically acceptable carrier.

10. A pharmaceutical composition comprising as an active ingredient a peptide according to claim 3 and a pharmaceutically acceptable carrier.

* * * * *

```
                        SEQUENCE LISTING

<160> NUMBER OF SEQ ID NOS: 90

<210> SEQ ID NO 1
<211> LENGTH: 9
<212> TYPE: PRT
<213> ORGANISM: Artificial sequence
<220> FEATURE:
<223> OTHER INFORMATION: Synthetic peptide

<400> SEQUENCE: 1

Lys Gly His Tyr Ala Glu Arg Val Gly
1               5

<210> SEQ ID NO 2
<211> LENGTH: 9
<212> TYPE: PRT
<213> ORGANISM: Artificial sequence
<220> FEATURE:
<223> OTHER INFORMATION: Synthetic peptide

<400> SEQUENCE: 2

Lys Gly Asn Tyr Ala Glu Arg Ile Ala
1               5

<210> SEQ ID NO 3
<211> LENGTH: 9
<212> TYPE: PRT
<213> ORGANISM: Artificial sequence
<220> FEATURE:
<223> OTHER INFORMATION: consensus
<220> FEATURE:
<221> NAME/KEY: misc_feature
<222> LOCATION: (1)..(1)
<223> OTHER INFORMATION: Absent, Lys, carbobenzoxy-Lys, acetyl-Lys GLn
      or Arg
<220> FEATURE:
<221> NAME/KEY: misc_feature
<222> LOCATION: (2)..(2)
<223> OTHER INFORMATION: Absent, Gly, Ala, Thr or Sar
<220> FEATURE:
<221> NAME/KEY: misc_feature
<222> LOCATION: (3)..(3)
<223> OTHER INFORMATION: Absent, His, MeHis,Thr,  Asn or Benzyl-His
<220> FEATURE:
<221> NAME/KEY: misc_feature
<222> LOCATION: (4)..(4)
<223> OTHER INFORMATION: Absent, Tyr, MeTyr, Ser or Tyr-O-Benzyl
<220> FEATURE:
<221> NAME/KEY: misc_feature
<222> LOCATION: (5)..(5)
<223> OTHER INFORMATION: Absent, Ala, MeAla Gly, His or Ser
```

```
<220> FEATURE:
<221> NAME/KEY: misc_feature
<222> LOCATION: (6)..(6)
<223> OTHER INFORMATION: Absent, Glu, Gly,  Gln, Glu-O-Benzyl or MeGlu
<220> FEATURE:
<221> NAME/KEY: misc_feature
<222> LOCATION: (7)..(7)
<223> OTHER INFORMATION: Absent, Arg, Arg-Tosyl, Lys or MeArg
<220> FEATURE:
<221> NAME/KEY: misc_feature
<222> LOCATION: (8)..(8)
<223> OTHER INFORMATION: Absent, Leu, Ile, Val or MeVal
<220> FEATURE:
<221> NAME/KEY: misc_feature
<222> LOCATION: (9)..(9)
<223> OTHER INFORMATION: Absent, Ala, Gly, Gly-amide or Sar

<400> SEQUENCE: 3

Xaa Xaa Xaa Xaa Xaa Xaa Xaa Xaa Xaa
1               5

<210> SEQ ID NO 4
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (9)..(9)
<223> OTHER INFORMATION: Gly-amide

<400> SEQUENCE: 4

Lys Gly His Tyr Ala Glu Arg Val Xaa
1               5

<210> SEQ ID NO 5
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: acetyl-Lys

<400> SEQUENCE: 5

Xaa Gly His Tyr Ala Glu Arg Val Gly
1               5

<210> SEQ ID NO 6
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: acetyl-Lys
<220> FEATURE:
<221> NAME/KEY: misc_feature
<222> LOCATION: (9)..(9)
<223> OTHER INFORMATION: Gly-amide

<400> SEQUENCE: 6

Xaa Gly His Tyr Ala Glu Arg Val Xaa
1               5
```

```
<210> SEQ ID NO 7
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: carbobenzoxy-Lys

<400> SEQUENCE: 7

Xaa Gly His Tyr Ala Glu Arg Val Gly
1               5

<210> SEQ ID NO 8
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: MeHis
<220> FEATURE:
<221> NAME/KEY: misc_feature
<222> LOCATION: (4)..(4)
<223> OTHER INFORMATION: MeTyr

<400> SEQUENCE: 8

Lys Gly Xaa Xaa Ala Glu Arg Val Gly
1               5

<210> SEQ ID NO 9
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (5)..(5)
<223> OTHER INFORMATION: MeAla

<400> SEQUENCE: 9

Lys Gly His Tyr Xaa Glu Arg Val Gly
1               5

<210> SEQ ID NO 10
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: MeTyr

<400> SEQUENCE: 10

Lys Gly His Xaa Ala Glu Arg Val Gly
1               5

<210> SEQ ID NO 11
<211> LENGTH: 9
<212> TYPE: PRT
<213> ORGANISM: Artificial sequence
<220> FEATURE:
<223> OTHER INFORMATION: Synthetic peptide
```

```
<220> FEATURE:
<221> NAME/KEY: misc_feature
<222> LOCATION: (7)..(7)
<223> OTHER INFORMATION: MeArg

<400> SEQUENCE: 11

Lys Gly His Tyr Ala Glu Xaa Val Gly
1               5

<210> SEQ ID NO 12
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (6)..(6)
<223> OTHER INFORMATION: MeGlu

<400> SEQUENCE: 12

Lys Gly His Tyr Ala Xaa Arg Val Gly
1               5

<210> SEQ ID NO 13
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (8)..(8)
<223> OTHER INFORMATION: MeVal

<400> SEQUENCE: 13

Lys Gly His Tyr Ala Glu Arg Xaa Gly
1               5

<210> SEQ ID NO 14
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Sar

<400> SEQUENCE: 14

Lys Xaa His Tyr Ala Glu Arg Val Gly
1               5

<210> SEQ ID NO 15
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (9)..(9)
<223> OTHER INFORMATION: Sar

<400> SEQUENCE: 15

Lys Gly His Tyr Ala Glu Arg Val Xaa
1               5
```

<210> SEQ ID NO 16
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Sar
<220> FEATURE:
<221> NAME/KEY: misc_feature
<222> LOCATION: (9)..(9)
<223> OTHER INFORMATION: Sar

<400> SEQUENCE: 16

Lys Xaa His Tyr Ala Glu Arg Val Xaa
1               5

<210> SEQ ID NO 17
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: MeTyr
<220> FEATURE:
<221> NAME/KEY: misc_feature
<222> LOCATION: (9)..(9)
<223> OTHER INFORMATION: Gly-amide

<400> SEQUENCE: 17

Lys Gly His Xaa Ala Glu Arg Val Xaa
1               5

<210> SEQ ID NO 18
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: MeHis
<220> FEATURE:
<221> NAME/KEY: misc_feature
<222> LOCATION: (9)..(9)
<223> OTHER INFORMATION: Gly-amide

<400> SEQUENCE: 18

Lys Gly Xaa Tyr Ala Glu Arg Val Xaa
1               5

<210> SEQ ID NO 19
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Sar
<220> FEATURE:
<221> NAME/KEY: misc_feature
<222> LOCATION: (9)..(9)
<223> OTHER INFORMATION: Gly-amide

<400> SEQUENCE: 19

Lys Xaa His Tyr Ala Glu Arg Val Xaa
1               5

<210> SEQ ID NO 20
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Sar
<220> FEATURE:
<221> NAME/KEY: misc_feature
<222> LOCATION: (3)..(3)
<223> OTHER INFORMATION: MeHis
<220> FEATURE:
<221> NAME/KEY: misc_feature
<222> LOCATION: (4)..(4)
<223> OTHER INFORMATION: MeTyr

<400> SEQUENCE: 20

Lys Xaa Xaa Xaa Ala Glu Arg Val Gly
1               5

<210> SEQ ID NO 21
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Sar
<220> FEATURE:
<221> NAME/KEY: misc_feature
<222> LOCATION: (3)..(3)
<223> OTHER INFORMATION: MeHis

<400> SEQUENCE: 21

Lys Xaa Xaa Tyr Ala Glu Arg Val Gly
1               5

<210> SEQ ID NO 22
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Sar
<220> FEATURE:
<221> NAME/KEY: misc_feature
<222> LOCATION: (4)..(4)
<223> OTHER INFORMATION: MeTyr

<400> SEQUENCE: 22

Lys Xaa His Xaa Ala Glu Arg Val Gly
1               5

<210> SEQ ID NO 23
<211> LENGTH: 9
<212> TYPE: PRT
<213> ORGANISM: Artificial sequence
<220> FEATURE:
<223> OTHER INFORMATION: Synthetic peptide

```
<220> FEATURE:
<221> NAME/KEY: misc_feature
<222> LOCATION: (2)..(2)
<223> OTHER INFORMATION: Sar
<220> FEATURE:
<221> NAME/KEY: misc_feature
<222> LOCATION: (8)..(8)
<223> OTHER INFORMATION: MeVal

<400> SEQUENCE: 23

Lys Xaa His Tyr Ala Glu Arg Xaa Gly
1               5

<210> SEQ ID NO 24
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (8)..(8)
<223> OTHER INFORMATION: MeVal
<220> FEATURE:
<221> NAME/KEY: misc_feature
<222> LOCATION: (9)..(9)
<223> OTHER INFORMATION: Sar

<400> SEQUENCE: 24

Lys Gly His Tyr Ala Glu Arg Xaa Xaa
1               5

<210> SEQ ID NO 25
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Sar
<220> FEATURE:
<221> NAME/KEY: misc_feature
<222> LOCATION: (8)..(8)
<223> OTHER INFORMATION: MeVal
<220> FEATURE:
<221> NAME/KEY: misc_feature
<222> LOCATION: (9)..(9)
<223> OTHER INFORMATION: Sar

<400> SEQUENCE: 25

Lys Xaa His Tyr Ala Glu Arg Xaa Xaa
1               5

<210> SEQ ID NO 26
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Sar
<220> FEATURE:
<221> NAME/KEY: misc_feature
<222> LOCATION: (5)..(5)
<223> OTHER INFORMATION: MeAla
```

```
<400> SEQUENCE: 26

Lys Xaa His Tyr Xaa Glu Arg Val Gly
1               5

<210> SEQ ID NO 27
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Sar
<220> FEATURE:
<221> NAME/KEY: misc_feature
<222> LOCATION: (4)..(4)
<223> OTHER INFORMATION: MeTyr
<220> FEATURE:
<221> NAME/KEY: misc_feature
<222> LOCATION: (9)..(9)
<223> OTHER INFORMATION: Gly-amide

<400> SEQUENCE: 27

Lys Xaa His Xaa Ala Glu Arg Val Xaa
1               5

<210> SEQ ID NO 28
<211> LENGTH: 9
<212> TYPE: PRT
<213> ORGANISM: Artificial sequence
<220> FEATURE:
<223> OTHER INFORMATION: Synthetic peptide

<400> SEQUENCE: 28

Lys Ala His Tyr Ala Glu Arg Val Gly
1               5

<210> SEQ ID NO 29
<211> LENGTH: 9
<212> TYPE: PRT
<213> ORGANISM: Artificial sequence
<220> FEATURE:
<223> OTHER INFORMATION: Synthetic peptide

<400> SEQUENCE: 29

Lys Ala Asn Tyr Ala Glu Arg Val Gly
1               5

<210> SEQ ID NO 30
<211> LENGTH: 9
<212> TYPE: PRT
<213> ORGANISM: Artificial sequence
<220> FEATURE:
<223> OTHER INFORMATION: Synthetic peptide

<400> SEQUENCE: 30

Lys Gly His Tyr Ser Glu Arg Val Gly
1               5

<210> SEQ ID NO 31
<211> LENGTH: 9
<212> TYPE: PRT
<213> ORGANISM: Artificial sequence
<220> FEATURE:
<223> OTHER INFORMATION: Synthetic peptide
```

```
<400> SEQUENCE: 31

Lys Gly Asn Tyr Ala Glu Arg Val Gly
1               5

<210> SEQ ID NO 32
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (5)..(5)
<223> OTHER INFORMATION: MeAla

<400> SEQUENCE: 32

Lys Ala Asn Tyr Xaa Glu Arg Val Gly
1               5

<210> SEQ ID NO 33
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (5)..(5)
<223> OTHER INFORMATION: MeAla

<400> SEQUENCE: 33

Lys Ala His Tyr Xaa Glu Arg Val Gly
1               5

<210> SEQ ID NO 34
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Tyr-O-Benzyl

<400> SEQUENCE: 34

Lys Gly His Xaa Ala Glu Arg Val Gly
1               5

<210> SEQ ID NO 35
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (6)..(6)
<223> OTHER INFORMATION: Glu-O-Benzyl

<400> SEQUENCE: 35

Lys Gly His Tyr Ala Xaa Arg Val Gly
1               5

<210> SEQ ID NO 36
<211> LENGTH: 9
<212> TYPE: PRT
<213> ORGANISM: Artificial sequence
```

```
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Benzyl-His

<400> SEQUENCE: 36

Lys Gly Xaa Tyr Ala Glu Arg Val Gly
1               5

<210> SEQ ID NO 37
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (7)..(7)
<223> OTHER INFORMATION: Arg-Tosyl

<400> SEQUENCE: 37

Lys Gly His Tyr Ala Glu Xaa Val Gly
1               5

<210> SEQ ID NO 38
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: acetyl-Lys
<220> FEATURE:
<221> NAME/KEY: misc_feature
<222> LOCATION: (3)..(3)
<223> OTHER INFORMATION: Benzyl-His
<220> FEATURE:
<221> NAME/KEY: misc_feature
<222> LOCATION: (4)..(4)
<223> OTHER INFORMATION: Tyr-O-Benzyl
<220> FEATURE:
<221> NAME/KEY: misc_feature
<222> LOCATION: (6)..(6)
<223> OTHER INFORMATION: Glu-O-Benzyl
<220> FEATURE:
<221> NAME/KEY: misc_feature
<222> LOCATION: (7)..(7)
<223> OTHER INFORMATION: Arg-Tosyl
<220> FEATURE:
<221> NAME/KEY: misc_feature
<222> LOCATION: (9)..(9)
<223> OTHER INFORMATION: Gly-amide

<400> SEQUENCE: 38

Xaa Gly Xaa Xaa Ala Xaa Xaa Val Xaa
1               5

<210> SEQ ID NO 39
<211> LENGTH: 9
<212> TYPE: PRT
<213> ORGANISM: Artificial sequence
<220> FEATURE:
<223> OTHER INFORMATION: Synthetic peptide

<400> SEQUENCE: 39

Lys Gly His Tyr Ala Glu Lys Val Gly
1               5
```

```
<210> SEQ ID NO 40
<211> LENGTH: 9
<212> TYPE: PRT
<213> ORGANISM: Artificial sequence
<220> FEATURE:
<223> OTHER INFORMATION: Synthetic peptide

<400> SEQUENCE: 40

Lys Gly His Tyr Ala Gln Lys Val Gly
1               5

<210> SEQ ID NO 41
<211> LENGTH: 9
<212> TYPE: PRT
<213> ORGANISM: Artificial sequence
<220> FEATURE:
<223> OTHER INFORMATION: Synthetic peptide

<400> SEQUENCE: 41

Gln Gly Asn Tyr Ala Glu Arg Ile Gly
1               5

<210> SEQ ID NO 42
<211> LENGTH: 9
<212> TYPE: PRT
<213> ORGANISM: Artificial sequence
<220> FEATURE:
<223> OTHER INFORMATION: Synthetic peptide

<400> SEQUENCE: 42

Arg Thr Thr Ser His Gly Arg Val Gly
1               5

<210> SEQ ID NO 43
<211> LENGTH: 4
<212> TYPE: PRT
<213> ORGANISM: Artificial sequence
<220> FEATURE:
<223> OTHER INFORMATION: Synthetic peptide

<400> SEQUENCE: 43

Tyr Ala Glu Arg
1

<210> SEQ ID NO 44
<211> LENGTH: 7
<212> TYPE: PRT
<213> ORGANISM: Artificial sequence
<220> FEATURE:
<223> OTHER INFORMATION: Synthetic peptide

<400> SEQUENCE: 44

His Tyr Ala Glu Arg Val Gly
1               5

<210> SEQ ID NO 45
<211> LENGTH: 6
<212> TYPE: PRT
<213> ORGANISM: Artificial sequence
<220> FEATURE:
<223> OTHER INFORMATION: Synthetic peptide

<400> SEQUENCE: 45

Tyr Ala Glu Arg Val Gly
1               5
```

```
<210> SEQ ID NO 46
<211> LENGTH: 5
<212> TYPE: PRT
<213> ORGANISM: Artificial sequence
<220> FEATURE:
<223> OTHER INFORMATION: Synthetic peptide

<400> SEQUENCE: 46

Gly His Tyr Ala Glu
1               5

<210> SEQ ID NO 47
<211> LENGTH: 8
<212> TYPE: PRT
<213> ORGANISM: Artificial sequence
<220> FEATURE:
<223> OTHER INFORMATION: Synthetic peptide

<400> SEQUENCE: 47

Gly His Tyr Ala Glu Arg Val Gly
1               5

<210> SEQ ID NO 48
<211> LENGTH: 4
<212> TYPE: PRT
<213> ORGANISM: Artificial sequence
<220> FEATURE:
<223> OTHER INFORMATION: Synthetic peptide

<400> SEQUENCE: 48

Ala Glu Arg Val
1

<210> SEQ ID NO 49
<211> LENGTH: 7
<212> TYPE: PRT
<213> ORGANISM: Artificial sequence
<220> FEATURE:
<223> OTHER INFORMATION: Synthetic peptide

<400> SEQUENCE: 49

Lys Gly His Tyr Ala Glu Arg
1               5

<210> SEQ ID NO 50
<211> LENGTH: 8
<212> TYPE: PRT
<213> ORGANISM: Artificial sequence
<220> FEATURE:
<223> OTHER INFORMATION: Synthetic peptide

<400> SEQUENCE: 50

Lys Gly His Tyr Ala Glu Arg Val
1               5

<210> SEQ ID NO 51
<211> LENGTH: 3
<212> TYPE: PRT
<213> ORGANISM: Artificial sequence
<220> FEATURE:
<223> OTHER INFORMATION: Synthetic peptide

<400> SEQUENCE: 51

Glu Arg Val
1
```

```
<210> SEQ ID NO 52
<211> LENGTH: 5
<212> TYPE: PRT
<213> ORGANISM: Artificial sequence
<220> FEATURE:
<223> OTHER INFORMATION: Synthetic peptide

<400> SEQUENCE: 52

Lys Gly His Tyr Ala
1               5

<210> SEQ ID NO 53
<211> LENGTH: 5
<212> TYPE: PRT
<213> ORGANISM: Artificial sequence
<220> FEATURE:
<223> OTHER INFORMATION: Synthetic peptide

<400> SEQUENCE: 53

Ala Glu Arg Val Gly
1               5

<210> SEQ ID NO 54
<211> LENGTH: 5
<212> TYPE: PRT
<213> ORGANISM: Artificial sequence
<220> FEATURE:
<223> OTHER INFORMATION: Synthetic peptide

<400> SEQUENCE: 54

Tyr Ala Glu Arg Val
1               5

<210> SEQ ID NO 55
<211> LENGTH: 4
<212> TYPE: PRT
<213> ORGANISM: Artificial sequence
<220> FEATURE:
<223> OTHER INFORMATION: Synthetic peptide

<400> SEQUENCE: 55

Glu Arg Val Gly
1

<210> SEQ ID NO 56
<211> LENGTH: 3
<212> TYPE: PRT
<213> ORGANISM: Artificial sequence
<220> FEATURE:
<223> OTHER INFORMATION: Synthetic peptide

<400> SEQUENCE: 56

Arg Val Gly
1

<210> SEQ ID NO 57
<211> LENGTH: 2
<212> TYPE: PRT
<213> ORGANISM: Artificial sequence
<220> FEATURE:
<223> OTHER INFORMATION: Synthetic peptide

<400> SEQUENCE: 57

Gly His
1
```

```
<210> SEQ ID NO 58
<211> LENGTH: 2
<212> TYPE: PRT
<213> ORGANISM: Artificial sequence
<220> FEATURE:
<223> OTHER INFORMATION: Synthetic peptide

<400> SEQUENCE: 58

Val Gly
1

<210> SEQ ID NO 59
<211> LENGTH: 2
<212> TYPE: PRT
<213> ORGANISM: Artificial sequence
<220> FEATURE:
<223> OTHER INFORMATION: Synthetic peptide

<400> SEQUENCE: 59

Tyr Ala
1

<210> SEQ ID NO 60
<211> LENGTH: 4
<212> TYPE: PRT
<213> ORGANISM: Artificial sequence
<220> FEATURE:
<223> OTHER INFORMATION: Synthetic peptide

<400> SEQUENCE: 60

Lys Gly His Tyr
1

<210> SEQ ID NO 61
<211> LENGTH: 5
<212> TYPE: PRT
<213> ORGANISM: Artificial sequence
<220> FEATURE:
<223> OTHER INFORMATION: Synthetic peptide

<400> SEQUENCE: 61

Lys Gly His Tyr Ala
1               5

<210> SEQ ID NO 62
<211> LENGTH: 7
<212> TYPE: PRT
<213> ORGANISM: Artificial sequence
<220> FEATURE:
<223> OTHER INFORMATION: Synthetic peptide

<400> SEQUENCE: 62

Gly His Tyr Ala Glu Arg Val
1               5

<210> SEQ ID NO 63
<211> LENGTH: 2
<212> TYPE: PRT
<213> ORGANISM: Artificial sequence
<220> FEATURE:
<223> OTHER INFORMATION: Synthetic peptide

<400> SEQUENCE: 63

Lys Gly
1
```

```
<210> SEQ ID NO 64
<211> LENGTH: 7
<212> TYPE: PRT
<213> ORGANISM: Artificial sequence
<220> FEATURE:
<223> OTHER INFORMATION: Synthetic peptide

<400> SEQUENCE: 64

Lys Ala Asn Tyr Ala Glu Arg
1               5

<210> SEQ ID NO 65
<211> LENGTH: 8
<212> TYPE: PRT
<213> ORGANISM: Artificial sequence
<220> FEATURE:
<223> OTHER INFORMATION: Synthetic peptide

<400> SEQUENCE: 65

Lys Gly His Tyr Ala Glu Val Gly
1               5

<210> SEQ ID NO 66
<211> LENGTH: 11
<212> TYPE: PRT
<213> ORGANISM: Artificial sequence
<220> FEATURE:
<223> OTHER INFORMATION: consensus
<220> FEATURE:
<221> NAME/KEY: misc_feature
<222> LOCATION: (1)..(1)
<223> OTHER INFORMATION: Absent or selected from the group consisting of
      Met, Arg, Leu-Arg, Leu-Leu-Arg, and Arg-Leu-Leu-Arg
<220> FEATURE:
<221> NAME/KEY: misc_feature
<222> LOCATION: (2)..(2)
<223> OTHER INFORMATION: Lys, carbobenzoxy-Lys, acetyl-Lys, Gln or Arg
<220> FEATURE:
<221> NAME/KEY: misc_feature
<222> LOCATION: (3)..(3)
<223> OTHER INFORMATION: Gly, Ala, Sar or Thr
<220> FEATURE:
<221> NAME/KEY: misc_feature
<222> LOCATION: (4)..(4)
<223> OTHER INFORMATION: His, MeHis, Benzyl-His, Asn or Thr
<220> FEATURE:
<221> NAME/KEY: misc_feature
<222> LOCATION: (5)..(5)
<223> OTHER INFORMATION: Tyr, MeTyr, Tyr-O-Benzyl or Ser
<220> FEATURE:
<221> NAME/KEY: misc_feature
<222> LOCATION: (6)..(6)
<223> OTHER INFORMATION: Ala, MeAla, Gly, Ser or His
<220> FEATURE:
<221> NAME/KEY: misc_feature
<222> LOCATION: (7)..(7)
<223> OTHER INFORMATION: Glu, Glu-O-Benzyl, MeGlu, Gly or Gln
<220> FEATURE:
<221> NAME/KEY: misc_feature
<222> LOCATION: (8)..(8)
<223> OTHER INFORMATION: Arg, Arg-Tosyl, MeArg or Lys
<220> FEATURE:
<221> NAME/KEY: misc_feature
<222> LOCATION: (9)..(9)
<223> OTHER INFORMATION: Val, MeVal, Leu or Ile
<220> FEATURE:
<221> NAME/KEY: misc_feature
<222> LOCATION: (10)..(10)
<223> OTHER INFORMATION: Gly, Gly-amide, Ala or Sar
<220> FEATURE:
<221> NAME/KEY: misc_feature
<222> LOCATION: (11)..(11)
<223> OTHER INFORMATION: Absent or selected from the group consisting of
      Ala, Ala-Gly, and Ala-Gly-Ala
```

```
<400> SEQUENCE: 66

Xaa Xaa Xaa Xaa Xaa Xaa Xaa Xaa Xaa Xaa Xaa
1               5                   10

<210> SEQ ID NO 67
<211> LENGTH: 10
<212> TYPE: PRT
<213> ORGANISM: Artificial sequence
<220> FEATURE:
<223> OTHER INFORMATION: Synthetic peptide

<400> SEQUENCE: 67

Arg Lys Gly His Tyr Ala Glu Arg Val Gly
1               5                   10

<210> SEQ ID NO 68
<211> LENGTH: 10
<212> TYPE: PRT
<213> ORGANISM: Artificial sequence
<220> FEATURE:
<223> OTHER INFORMATION: Synthetic peptide

<400> SEQUENCE: 68

Lys Gly His Tyr Ala Glu Arg Val Gly Ala
1               5                   10

<210> SEQ ID NO 69
<211> LENGTH: 11
<212> TYPE: PRT
<213> ORGANISM: Artificial sequence
<220> FEATURE:
<223> OTHER INFORMATION: Synthetic peptide

<400> SEQUENCE: 69

Arg Lys Gly His Tyr Ala Glu Arg Val Gly Ala
1               5                   10

<210> SEQ ID NO 70
<211> LENGTH: 11
<212> TYPE: PRT
<213> ORGANISM: Artificial sequence
<220> FEATURE:
<223> OTHER INFORMATION: Synthetic peptide

<400> SEQUENCE: 70

Leu Arg Lys Gly His Tyr Ala Glu Arg Val Gly
1               5                   10

<210> SEQ ID NO 71
<211> LENGTH: 11
<212> TYPE: PRT
<213> ORGANISM: Artificial sequence
<220> FEATURE:
<223> OTHER INFORMATION: Synthetic peptide

<400> SEQUENCE: 71

Lys Gly His Tyr Ala Glu Arg Val Gly Ala Gly
1               5                   10

<210> SEQ ID NO 72
<211> LENGTH: 12
<212> TYPE: PRT
<213> ORGANISM: Artificial sequence
<220> FEATURE:
<223> OTHER INFORMATION: Synthetic peptide
```

```
<400> SEQUENCE: 72

Leu Arg Lys Gly His Tyr Ala Glu Arg Val Gly Ala
1               5                   10

<210> SEQ ID NO 73
<211> LENGTH: 13
<212> TYPE: PRT
<213> ORGANISM: Artificial sequence
<220> FEATURE:
<223> OTHER INFORMATION: Synthetic peptide

<400> SEQUENCE: 73

Leu Arg Lys Gly His Tyr Ala Glu Arg Val Gly Ala Gly
1               5                   10

<210> SEQ ID NO 74
<211> LENGTH: 12
<212> TYPE: PRT
<213> ORGANISM: Artificial sequence
<220> FEATURE:
<223> OTHER INFORMATION: Synthetic peptide

<400> SEQUENCE: 74

Leu Leu Arg Lys Gly His Tyr Ala Glu Arg Val Gly
1               5                   10

<210> SEQ ID NO 75
<211> LENGTH: 13
<212> TYPE: PRT
<213> ORGANISM: Artificial sequence
<220> FEATURE:
<223> OTHER INFORMATION: Synthetic peptide

<400> SEQUENCE: 75

Leu Leu Arg Lys Gly His Tyr Ala Glu Arg Val Gly Ala
1               5                   10

<210> SEQ ID NO 76
<211> LENGTH: 14
<212> TYPE: PRT
<213> ORGANISM: Artificial sequence
<220> FEATURE:
<223> OTHER INFORMATION: Synthetic peptide

<400> SEQUENCE: 76

Leu Leu Arg Lys Gly His Tyr Ala Glu Arg Val Gly Ala Gly
1               5                   10

<210> SEQ ID NO 77
<211> LENGTH: 15
<212> TYPE: PRT
<213> ORGANISM: Artificial sequence
<220> FEATURE:
<223> OTHER INFORMATION: Synthetic peptide

<400> SEQUENCE: 77

Leu Leu Arg Lys Gly His Tyr Ala Glu Arg Val Gly Ala Gly Ala
1               5                   10                  15

<210> SEQ ID NO 78
<211> LENGTH: 12
<212> TYPE: PRT
<213> ORGANISM: Artificial sequence
<220> FEATURE:
<223> OTHER INFORMATION: Synthetic peptide
```

-continued

```
<400> SEQUENCE: 78

Lys Gly His Tyr Ala Glu Arg Val Gly Ala Gly Ala
1               5                   10

<210> SEQ ID NO 79
<211> LENGTH: 13
<212> TYPE: PRT
<213> ORGANISM: Artificial sequence
<220> FEATURE:
<223> OTHER INFORMATION: Synthetic peptide

<400> SEQUENCE: 79

Arg Leu Leu Arg Lys Gly His Tyr Ala Glu Arg Val Gly
1               5                   10

<210> SEQ ID NO 80
<211> LENGTH: 14
<212> TYPE: PRT
<213> ORGANISM: Artificial sequence
<220> FEATURE:
<223> OTHER INFORMATION: Synthetic peptide

<400> SEQUENCE: 80

Arg Leu Leu Arg Lys Gly His Tyr Ala Glu Arg Val Gly Ala
1               5                   10

<210> SEQ ID NO 81
<211> LENGTH: 15
<212> TYPE: PRT
<213> ORGANISM: Artificial sequence
<220> FEATURE:
<223> OTHER INFORMATION: Synthetic peptide

<400> SEQUENCE: 81

Arg Leu Leu Arg Lys Gly His Tyr Ala Glu Arg Val Gly Ala Gly
1               5                   10                  15

<210> SEQ ID NO 82
<211> LENGTH: 10
<212> TYPE: PRT
<213> ORGANISM: Artificial sequence
<220> FEATURE:
<223> OTHER INFORMATION: Synthetic peptide

<400> SEQUENCE: 82

Met Lys Gly His Tyr Ala Glu Arg Val Gly
1               5                   10

<210> SEQ ID NO 83
<211> LENGTH: 10
<212> TYPE: PRT
<213> ORGANISM: Artificial sequence
<220> FEATURE:
<223> OTHER INFORMATION: Synthetic peptide

<400> SEQUENCE: 83

Arg Lys Ala Asn Tyr Ala Glu Arg Val Gly
1               5                   10

<210> SEQ ID NO 84
<211> LENGTH: 30
<212> TYPE: DNA
<213> ORGANISM: Artificial sequence
<220> FEATURE:
<223> OTHER INFORMATION: Single strand DNA oligonucleotide
```

```
<400> SEQUENCE: 84
atggccaacg cgctcggcgt agtggccctt                                        30

<210> SEQ ID NO 85
<211> LENGTH: 9
<212> TYPE: PRT
<213> ORGANISM: Artificial sequence
<220> FEATURE:
<223> OTHER INFORMATION: Synthetic peptide

<400> SEQUENCE: 85

Lys Gly Asn Tyr Ser Glu Arg Val Gly
1               5

<210> SEQ ID NO 86
<211> LENGTH: 9
<212> TYPE: PRT
<213> ORGANISM: Artificial sequence
<220> FEATURE:
<223> OTHER INFORMATION: Synthetic peptide

<400> SEQUENCE: 86

Lys Gly Asn Tyr Ala Glu Arg Val Gly
1               5

<210> SEQ ID NO 87
<211> LENGTH: 9
<212> TYPE: PRT
<213> ORGANISM: Artificial sequence
<220> FEATURE:
<223> OTHER INFORMATION: Synthetic peptide

<400> SEQUENCE: 87

Lys Ala His Tyr Ser Glu Arg Val Gly
1               5

<210> SEQ ID NO 88
<211> LENGTH: 11
<212> TYPE: PRT
<213> ORGANISM: Artificial sequence
<220> FEATURE:
<223> OTHER INFORMATION: Synthetic peptide

<400> SEQUENCE: 88

Lys Ser Arg Thr Thr Ser His Gly Arg Val Gly
1               5                   10

<210> SEQ ID NO 89
<211> LENGTH: 15
<212> TYPE: PRT
<213> ORGANISM: Artificial sequence
<220> FEATURE:
<223> OTHER INFORMATION: Synthetic peptide

<400> SEQUENCE: 89

Leu Arg Lys Gly Asn Tyr Ala Glu Arg Val Gly Ala Gly Ala Pro
1               5                   10                  15

<210> SEQ ID NO 90
<211> LENGTH: 10
<212> TYPE: PRT
<213> ORGANISM: Artificial sequence
<220> FEATURE:
<223> OTHER INFORMATION: Synthetic peptide
```

```
-continued

<400> SEQUENCE: 90

Lys Gly His Tyr Ala Glu Arg Val Gly Cys
1               5                   10
```